United States Patent
Barta et al.

(10) Patent No.: US 7,659,394 B2
(45) Date of Patent: Feb. 9, 2010

(54) SUBSTITUTED MORPHOLINE COMPOUNDS FOR THE TREATMENT OF CENTRAL NERVOUS SYSTEM DISORDERS

(75) Inventors: Nancy S. Barta, Brighton, MI (US); Shelly Ann Glase, Ann Arbor, MI (US); David L. Gray, Dexter, MI (US); Gregory A. Reichard, Ann Arbor, MI (US); Lloyd Jerome Simons, Stockbridge, MI (US); Wenijan Xu, Ann Arbor, MI (US)

(73) Assignee: Pfizer Inc, New York, NY (US)

( * ) Notice: Subject to any disclaimer, the term of this patent is extended or adjusted under 35 U.S.C. 154(b) by 168 days.

(21) Appl. No.: 11/119,210

(22) Filed: Apr. 29, 2005

(65) Prior Publication Data

US 2005/0245519 A1    Nov. 3, 2005

Related U.S. Application Data

(60) Provisional application No. 60/567,244, filed on Apr. 30, 2004.

(51) Int. Cl.
C07D 295/04    (2006.01)
C07D 213/10    (2006.01)

(52) U.S. Cl. ..................................................... 544/124
(58) Field of Classification Search .................. 544/124
See application file for complete search history.

(56) References Cited

U.S. PATENT DOCUMENTS

| | | | |
|---|---|---|---|
| 4,116,665 A | | 9/1978 | Krumkalns et al. |
| 4,229,449 A | * | 10/1980 | Melloni et al. ............ 514/239.2 |
| 4,271,160 A | | 6/1981 | Melloni et al. |
| 4,782,054 A | | 11/1988 | Regnier et al. |
| 4,851,423 A | | 7/1989 | Girijavaliabhan et al. |
| 4,855,143 A | * | 8/1989 | Lowey ....................... 424/468 |
| 5,068,433 A | | 11/1991 | Melloni et al. |
| 5,272,167 A | | 12/1993 | Girijavallabhan et al. |
| 5,391,735 A | | 2/1995 | Melloni et al. |
| 5,441,985 A | | 8/1995 | Foreman |
| 5,459,144 A | | 10/1995 | Grijavallabhan et al. |
| 5,750,532 A | | 5/1998 | Girijavallabhan et al. |
| 5,945,117 A | | 8/1999 | El-Rashidy et al. |
| 6,335,338 B1 | * | 1/2002 | Bhatnagar et al. ........ 514/239.2 |
| 6,376,711 B1 | | 4/2002 | Henegar et al. |
| 6,423,708 B1 | | 7/2002 | Gibbs et al. |
| 6,465,458 B1 | | 10/2002 | Wong et al. |
| 6,528,529 B1 | | 3/2003 | Brann et al. |
| 6,610,690 B2 | | 8/2003 | Wong et al. |
| 6,635,675 B2 | | 10/2003 | Kranzler et al. |
| 6,656,935 B2 | | 12/2003 | Yamada et al. |
| 6,797,709 B2 | | 9/2004 | Yamada et al. |
| 6,831,175 B2 | | 12/2004 | Li et al. |
| 2002/0161002 A1 | | 10/2002 | Epstein et al. |
| 2003/0040464 A1 | | 2/2003 | Wong et al. |
| 2003/0144285 A1 | | 7/2003 | Brann et al. |
| 2003/0187026 A1 | | 10/2003 | Li et al. |
| 2003/0199511 A1 | | 10/2003 | Li et al. |
| 2003/0203055 A1 | | 10/2003 | Rao et al. |
| 2003/0229085 A1 | | 12/2003 | Blume et al. |
| 2003/0229095 A1 | | 12/2003 | Yamada et al. |
| 2004/0019116 A1 | | 1/2004 | Kranzler et al. |
| 2004/0034019 A1 | | 2/2004 | Tomlinson et al. |
| 2004/0034101 A1 | | 2/2004 | Rao et al. |
| 2004/0058925 A1 | | 3/2004 | Wong et al. |
| 2004/0142930 A1 | | 7/2004 | Yamada et al. |
| 2004/0147614 A1 | | 7/2004 | Wong et al. |
| 2004/0186148 A1 | | 9/2004 | Shankar et al. |
| 2005/0009927 A1 | | 1/2005 | Marek et al. |
| 2005/0059654 A1 | | 3/2005 | Arneric et al. |
| 2005/0245519 A1 | | 11/2005 | Barta et al. |

FOREIGN PATENT DOCUMENTS

BE    865.656    5/1978

(Continued)

OTHER PUBLICATIONS

J. G. Topliss, "A Manual Method for Applying the Hansch Approach to Drug Design", Journal of Medicinal Chemistry, 1977, vol. 20, No. 4, 463-469.*

(Continued)

*Primary Examiner*—Rebecca L Anderson
*Assistant Examiner*—Robert Havlin
(74) *Attorney, Agent, or Firm*—Gregg C. Benson; James T. Jones

(57) ABSTRACT

This invention relates to compounds of the formulae I

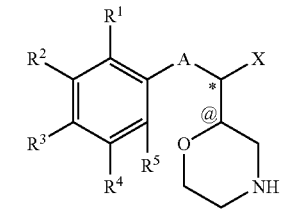

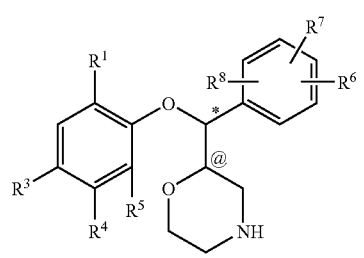

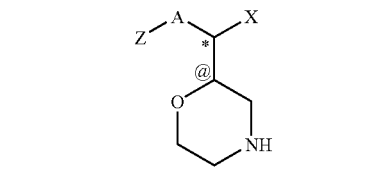

wherein $R^1$-$R^8$, A, X, and Z are defined as in the specification, pharmaceutical compositions containing them and their use in the treatment of central nervous system disorders.

10 Claims, No Drawings

FOREIGN PATENT DOCUMENTS

| | | |
|---|---|---|
| BE | 873.596 | 7/1979 |
| DE | 29 01 032.0 A1 | 1/1979 |
| DE | 2056 589.3 | 11/1979 |
| EP | 0 109 751 A1 | 5/1984 |
| EP | 0427605 | 5/1991 |
| EP | 0 286 495 B1 | 5/1993 |
| EP | 0 274 867 B1 | 4/1994 |
| EP | 1140788 B1 | 12/1999 |
| EP | 1308443 A2 | 12/1999 |
| FR | 2 442 839 | 6/1980 |
| GB | 1138405 | 1/1969 |
| GB | 1 295 447 | 11/1969 |
| GB | 1260886 | 1/1972 |
| GB | 1 310 235 | 3/1973 |
| GB | 2 167 407 A | 5/1986 |
| JP | 2004-189738 A | 7/2004 |
| WO | WO9111172 | 8/1991 |
| WO | WO9402518 | 2/1994 |
| WO | WO9608487 | 3/1996 |
| WO | WO 96/31487 A1 | 10/1996 |
| WO | WO 96/34851 A1 | 11/1996 |
| WO | WO 97/19059 A1 | 5/1997 |
| WO | WO 98/14433 A1 | 4/1998 |
| WO | WO9830560 | 7/1998 |
| WO | WO9855148 | 12/1998 |
| WO | WO 99/50247 A1 | 10/1999 |
| WO | WO 99/50262 A1 | 10/1999 |
| WO | WO 00/09491 A1 | 2/2000 |
| WO | WO 00/39072 A1 | 7/2000 |
| WO | WO0039072 | 7/2000 |
| WO | WO0059477 | 10/2000 |
| WO | WO 01/05763 A3 | 1/2001 |
| WO | WO0101973 | 1/2001 |
| WO | WO 01/44258 A1 | 6/2001 |
| WO | WO 01/53263 A1 | 7/2001 |
| WO | WO 01/83460 A1 | 11/2001 |
| WO | WO 02/36125 A1 | 5/2002 |
| WO | WO 03/037338 A2 | 5/2003 |
| WO | WO 03/051366 A3 | 6/2003 |
| WO | WO 03/059873 A1 | 7/2003 |
| WO | WO 2004/005255 A1 | 1/2004 |
| WO | WO2004058353 | 1/2004 |
| WO | WO 2004/013356 A1 | 2/2004 |
| WO | WO 2004/017977 A3 | 3/2004 |
| WO | WO 2004/018441 A1 | 3/2004 |
| WO | WO 2004/018840 A1 | 3/2004 |
| WO | WO 2004018440 | 3/2004 |
| WO | WO2004/048860 | 7/2004 |
| WO | WO 2004/058353 A2 | 7/2004 |
| WO | WO 2004/058353 A3 | 7/2004 |
| WO | WO 2005/000309 A2 | 1/2005 |
| WO | WO 2005/000309 A3 | 1/2005 |
| WO | WO 2005/020975 A2 | 3/2005 |
| WO | WO 2005/020975 A3 | 3/2005 |
| WO | WO 2005/020976 A2 | 3/2005 |
| WO | WO 2005/020976 A3 | 3/2005 |
| WO | WO 2005/021095 A2 | 3/2005 |
| WO | WO 2005/021095 A3 | 3/2005 |
| WO | WO 2005/023802 A1 | 3/2005 |
| WO | WO 2005/066144 A1 | 7/2005 |
| WO | WO 2005/076412 A2 | 8/2005 |
| WO | WO 2005/105100 A1 | 11/2005 |

OTHER PUBLICATIONS

J. A. H. Lainton, et al., "Design and Synthesis of A Diverse Morpholine Template Library", J. Comb. Chem., 2003, 5, 400-407.*

Patani et al. (Chem. Rev., 1996, 96, 3147-3176.*

T. Spencer, et al., "Adults with Attention-Deficit/hyperactivity Disorder: A Controversial Diagnosis," J Clin Psychiatry, 1998, pp. 59-68, Suppl. 7.

J. B. Schweitzer, et al., "Advance in the Pathophysiology and Treatement of Psychiatric Disorders: Implications for Internal Medicine," Medical Clinics of North America, May 2001, pp. 757-777 vol. 85 No. 3.

D. P. Cantwell, "Attention Deficit Disorder: A Review of the Past 10 Years", J Am Acad Child Adolesc Psychiatry, Aug. 1996, pp. 978-987, vol. 35, No. 8.

J. Elia, et al., "Treatment of Attention Deficit Hyperactivity", Eng. J. Med, Mar. 1999, pp. 780-788, vol. 340, No. 10.

E. E. Nolan, et al., "Teacher Reports of DSM-IV ADHD, ODD, and CD Symptoms in Schoolchildren," J Am Acad Child Adolesc Psychiatry, Feb. 2001, pp. 241249, vol. 40, No. 2.

M. Dulcan, et al., "Practice Parameters for the Assessment and Treatment of Children, Adolescents, and Adults with Attention-Deficit/Hyperactivity Disorder," Oct. 1997, pp. 85-121, vol. 36, Suppl. 10.

Cantwell, D., et al., "Attention Deficit Disorder: A Review of the Past 10 Years", J Am Acad Child Adolesc Psychiatry, Aug. 1996, pp. 978-987, vol. 35, No. 8.

Cryan, J., et al., "Noradrenergic lesions differentially alter the antidepressant-like effects of reboxetine in a modified forced swim test" Euro J Pharm, 2002, pp. 197-205, vol. 436, No. 3.

Dulcan, M., et al., "Practice Parameters for the Assessment and Treatment of Children, Adolescents, and Adults with Attention-Deficit/Hyperactivity Disorder," Oct. 1997, pp. 85-12, vol. 36, Suppl. 10.

Elia, J., et al., "Treatment of Attention Deficit Hyperactivity", Eng. J. Med, Mar. 1999, pp. 780-788, vol. 340, No. 10.

Harkin, A., et al., "The Effect of Reboxetine in Some Preclinical Tests Predictive of Antidepressant Activity", J. Psychopharmacology, 1997, pp. A39, vol. 11, No. 3, Suppl.

Melloni, P.; et al., "Configurational Studies On 2-Alpha-(2-Ethoxyphenoxy) Benzylmorpholine FCE 20124", Tetrahedron, 1985, pp. 1393-1399, vol. 41, No. 7.

Melloni, P., et al., "Potential Antidepressant Agents. Alpha-Aryloxy-Benzyl Derivatives Of Ethanolamine And Morpholine", Eur. J. Med. Chem. Chim. Ther., 1984, pp. 235-242, vol. 19, No. 3.

Nolan, E., et al., "Teacher Reports of DSM-IV ADHD, ODD, and CD Symptoms in Schoolchildren," J Am Acad Child Adolesc Psychiatry, Feb. 2001, pp. 241-249, vol. 40, No. 2.

Schou, M., et al., "Preparation and PET Evaluation Of [18F]FMPBM-D2- A Promising Brain Norepinephrine Transporter (Net) Radioligand", J. Label Compd. Radiopharm., 2003, pp. S59, vol. 46.

Schweitzer, J., et al., "Advance in the Pathophysiology and Treatment of Psychiatric Disorders: Implications for Internal Medicine," Medical Clinics of North America, May 2001, pp. 757-777, vol. 85, No. 3.

Spencer, T., et al., "Adults with Attention-Deficit/hyperactivity Disorder: A Controversial Diagnosis," J Clin Psychiatry, 1998, pp. 59-68, Suppl. 7.

Boursier-Neyret, C., et al., "Determination of S12024 enentlomers 1n human plasma by liquid chromatography after chiral pre-column derivatization", J Pharm & Biomed Anal, 1993, vol. 11, No. 11/12, pp. 1161-1166.

Corral, C., et al., "Synthesis and Preliminary Pharmacological Evaluation of Thiophene Analogues of Vlloxazine as potential Ant1 depressant Drugs", Bioorg & Med Chem, 1999, vol. 7, pp. 1349-1359.

O'Neil, Maryadeke J.,Sr. Editor: The Merck Index; 2001: 1456; 8210: Merck Research Laboratories; Whitehouse Station. N.J.

Haleblain, John K. Characterization of Habits and Crystalline Modification of Solids and their Pharmaceutical Applications, Journal of Pharmaceutical Sciences, vol. 64 No. 8, Aug. 1975, pp. 1269-1288.

Ferres, H,"Pro-Drugs of Beta-Lactam Antibiotics," Drugs of Today, vol. 19, No. 9, 1983 pp. 499-538.

Prabhakaran, J., et al. Chiral Synthesis of (2S, 3S)-2-(2-Morphotin-2-yi-2-phenylmethoxy)phenol, Chirality, 2004, vol. 16, 168-173.

Sluka, K. Stimulation of Deep Somatic Tissue with Capsaicin Produces Long-Lasting Mechanical Allodynia and Heat Hypoalgesia that Depends on Early Activation of the cAMP Pathway.. J. Neuroscience, 2002, vol. 22, pp. 5687-5693.

Wienkers, et al.,"Cytochrome P-450-Mediated Metabolism of the Individual Enantiomers of the Antidepressant Agent Reboxetine in Human Liver Microsomes", Drug Metabolism and Disposition, 1999. V. 27, No. 11, p. 1334-1340.

Park et al., "Metabolism of Fluorine Containing Drugs", Annu. Rev. Pharmacol. Toxicol. 2001. 41:443-70.

Bastin et al., "Salt selection and optimization procedures for pharmaceutical new chemical entities", Organic Process Research and Development, 2004, 4, 427-435.

Wermuth, Camille G., "Molecular Variations Based on Isosteric Replacements", *The Practice of Medicinal Chemistry*, pp. 203-237, 1996.

* cited by examiner

SUBSTITUTED MORPHOLINE COMPOUNDS FOR THE TREATMENT OF CENTRAL NERVOUS SYSTEM DISORDERS

This application is a United States utility application, which claims the benefit of priority to U.S. Provisional Application No. 60/567,244, filed Apr. 30, 2004.

This invention relates to materials and methods of preventing or treating central nervous system disorder or condition and in particular a method of treating or preventing attention deficit hyperactivity disorder ("ADHD") by administering a compound that inhibits the reuptake of norepinephrine. Such compounds are also referred to in the literature as selective norepinephrine reuptake inhibitors (NRIs).

BACKGROUND OF THE INVENTION

Attention deficit hyperactivity disorder (ADHD) has an estimated incidence in school age children of 3-5%, and is characterized by the core symptoms of hyperactivity, impulsivity, and/or inattention. The attentional symptoms of ADHD can be successfully treated with psychomotor stimulants such as methylphenidate (Ritalin). Clonidine, an $\alpha_2$-adrenoceptor agonist, treats the aggressive and oppositional symptoms. There is a potential for significant side effects with both methylphenidate and clonidine, making it important to identify other drugs that have similar or better efficacy with reduced side effects and abuse liability.

ADHD is one of the most common childhood psychiatric disorders and appears to be a common, often under recognized, psychiatric disease in adults as well (T. Spencer, et al., *J Clin Psychiatry*, 1998, 59 (Suppl. 7), 759-768). This disorder, which begins in childhood, may be followed by a lifelong expression of symptoms (e.g., inattention and/or impulsivity) (J B. Schweitzer, et al., *Med Clin North Am*, May 2001, 85:3, 757-777). ADHD may change its manifestations as it develops from preschool through adult life (D P. Cantwell, *J Am Acad Child Adolesc Psychiatry*, August 1996, 35 (8), 978-987; J. Elia, et al. *N Eng J Med*, March 1999, 340 (10), 780-788; E E. Nolan, et al., *J Am Acad Child Adolesc Psychaitry*, February 2001, 40 (2), 241-249).

The diagnosis of ADHD is based on clinical evaluation (M. Dulcan, et al. M, *J Am Acad Child Adolesc Psychaitry*, October 1997, 36 (10 Suppl), 85S-121S; *National Institutes of Health*, 1998). "The essential feature of ADHD is a persistent pattern of inattention and/or hyperactivity-impulsivity that is more frequent and severe than is typically observed in individuals at a comparative level of development" (Diagnostic and Statistical Manual of Mental Disorders (DSM-IV), American Psychiatric Association, Washington, D.C., 1994). In order to be diagnosed with ADHD, patients must demonstrate symptoms of ADHD that cause impairment before the age of seven years, and symptoms must have been ongoing for longer than six months in at least two settings (e.g., school [or work] and home). (See DSM-IV).

Several NRI compounds are known. Atomoxetine, an NRI, is now commercially available (Strattera®, Eli Lilly) and is beginning to be used extensively for the clinical treatment of ADHD in both children and adults. Atomoxetine represents a non-stimulant treatment for ADHD. The number of treated ADHD patients is expected to increase as a result of the introduction of atomoxetine and enhanced educational initiatives. Accordingly, there is an ongoing need for ADHD treatments that provide more efficacy than those treatments currently available.

SUMMARY OF THE INVENTION

The present invention relates to compounds of the formula I

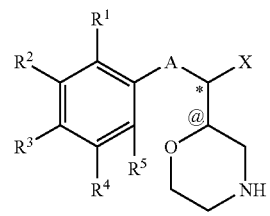

and pharmaceutically acceptable salts or derivatives thereof, wherein:

A is O or S;

X is aryl, a heterocycle, benzofused bicyclic, —$C_1$-$C_{10}$alkyl, —$C_2$-$C_8$alkenyl, —$C_5$-$C_8$cycloalkenyl, —$(CH_2)_n C_3$-$C_9$ cycloalkyl, fused cycloalkyl, H, $SCF_3$, hydroxy —$C_1$-$C_6$ alkyl, —$C_1$-$C_6$alkoxy, —$C_1$-$C_6$alkoxy$C_1$-$C_6$alkoxy, —$(CH_2)_n S$—$C_1$-$C_6$alkyl, —$(CH_2)_n SO_2$—$C_1$-$C_6$alkyl; wherein each group is optionally substituted by one or more substituents independently selected from —$C_1$-$C_6$ alkyl, —$C_3$-$C_8$cycloalkyl, —$C_1$-$C_6$ alkoxy, aryl, heterocycle, OH, halo, $CF_3$, —$CHF_2$, —$CH_2F$, —$OCF_3$, —$OCHF_2$, —$OCH_2F$, —$O(CH_2)_n CF_3$, —CN, —$CONH_2$, —CON(H)$C_1$-$C_6$alkyl, —CON($C_1$-$C_6$alkyl)$_2$, hydroxy-$C_1$-$C_6$alkyl, —$C_1$-$C_4$alkoxy, —$SCF_3$, $SO_2$, —$C_1$-$C_4$alkyl-S—$C_1$-$C_4$alkyl, —$C_1$-$C_4$alkyl-S—, —$C_1$-$C_4$alkylNR'R", NR'R", with the proviso that when X is phenyl, substituted phenyl, $C_1$-$C_4$ unsubstituted alkyl, halo-substituted $C_1$-$C_4$ alkyl, unsubstituted $C_3$-$C_8$ cycloalkyl, or halo-substituted $C_3$-$C_8$ cycloalkyl, then * and @ are either (R,S) or (S,R);

$R^1$-$R^5$ are independently selected from is H, —$C_1$-$C_6$ alkyl, aryl, —$C_3$-$C_8$cycloalkyl, —$C_1$-$C_6$ alkenyl, —$C_5$-$C_8$ cycloalkenyl, —$(CH_2)_n C_3$-$C_8$cycloalkyl, —$C_1$-$C_6$ alkoxy, —O-aryl, heterocycle, $SO_2$, OH, halo, —$CF_3$, —$CHF_2$, —$CH_2F$, —$OCF_3$, —$OCHF_2$, —$OCH_2F$, —$O(CH_2)_n CF_3$, —CN, —$CONH_2$, —CON(H)$C_1$-$C_6$alkyl, —CON($C_1$-$C_6$alkyl)$_2$, hydroxy-$C_1$-$C_6$alkyl, —$C_1$-$C_4$alkoxy$C_1$-$C_6$alkyl, —$SCF_3$, —$C_1$-$C_6$alkyl-$SO_2$, —$C_1$-$C_4$alkyl-S—$C_1$-$C_4$alkyl, —$C_1$-$C_4$alkyl-S—, $C_1$-$C_4$alkylNR'R", and NR'R", and when two of the groups $R^1$-$R^5$ are attached to the ring can form a benzofused bicyclic ring comprising a phenyl group fused to a 5 or 6 membered carbocyclic ring or a phenyl group fused to a 5 or 6 membered heterocyclic group containing at least one of N, O, or S heteroatom and wherein each of the groups —$C_1$-$C_6$ alkyl, aryl, —$C_3$-$C_8$cycloalkyl, —$C_2$-$C_8$alkenyl, —$C_5$-$C_8$cycloalkenyl, —$C_1$-$C_6$ alkoxy, heterocycle may be optionally substituted by one or more of the following groups: aryl, heterocycle, OH, halo, —$CF_3$, —$CHF_2$, —$CH_2F$, —$OCF_3$, —$OCHF_2$, —$OCH_2F$, —$O(CH_2)_n CF_3$, —CN, —$CONH_2$, —CON(H)$C_1$-$C_6$alkyl, —CON($C_1$-$C_6$alkyl)$_2$, hydroxy —$C_1$-$C_6$alkyl, $C_1$-$C_6$alkoxy, $C_1$-$C_6$alkyl, —$SCF_3$, —$C_1$-$C_6$alkyl$SO_2$, —$C_1$-$C_4$alkyl-S—$C_1$-$C_4$alkyl, —$C_1$-$C_4$alkyl-S—, —$C_1$-$C_4$alkylNR'R", and NR'R";

R' and R" are independently $C_1$-$C_6$alkyl or H;

n is 1 to 5;

* denotes a first chiral center; and

@ denotes a second chiral center.

An additional aspect of this invention relates to compounds of the formula I wherein $R^1$ is $C_1$-$C_6$alkyl, halogen, OH, —CN, —S$C_1$-$C_6$alkyl, —$CH_2$O$C_1$-$C_6$alkyl, $C_3$-$C_6$cycloalkyl, $C_1$-$C_6$alkoxy, phenyl, substituted phenyl, or pyridyl.

A further aspect of the invention relates to compounds wherein $R^1$ is —$C_1$-$C_6$alkoxy, F, —$C_1$-$C_6$alkyl, or —CN. Other aspects relate to compounds wherein $R^3$, $R^4$, and $R^5$ are not all substituted at the same time.

Yet a further aspect of the invention relates to compounds wherein at least two of $R^3$, $R^4$, and $R^5$ are hydrogen.

Yet a further aspect of the invention relates to compounds wherein $R^3$, $R^4$, and $R^5$ are independently selected from H, F, Cl, and —O$C_1$-$C_6$alkyl.

Yet a further aspect of the invention relates to compounds wherein X is a heterocycle.

Yet a further aspect of the invention relates to compounds wherein the heterocyle is pyridyl, thiazolyl, pyrazole, oxazole, benzofuran, or dihydrobenzofuran.

Yet a further aspect of the invention relates to compounds wherein the pyridyl is a 2-pyridyl group.

Yet a further aspect of the invention relates to compounds wherein $R^2$ is hydrogen.

Yet a further aspect of the invention relates to compounds wherein the conformation of both @ and * is S,S.

A further aspect of the invention relates to compounds of the formula II

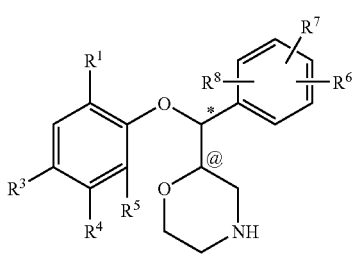

II and pharmaceutically acceptable salts or derivatives thereof, wherein:

$R^1$ and $R^6$, $R^7$ and $R^8$ are independently selected from H, —$C_1$-$C_6$ alkyl, aryl, —$C_3$-$C_8$cycloalkyl, —$C_2$-$C_6$ alkenyl, —$C_5$-$C_8$ cycloalkenyl, —$(CH_2)_nC_3$-$C_9$ cycloalkyl, —$C_1$-$C_6$ alkoxy, —O-aryl, heterocycle, —$SO_2$, OH, halo, —$CF_3$, —$CHF_2$, —$CH_2F$, $OCF_3$, —$OCHF_2$, —$OCH_2F$, —$O(CH_2)_nCF_3$, —CN, —$CONH_2$, —CON(H)$C_1$-$C_6$alkyl, —CON($C_1$-$C_6$alkyl)$_2$, hydroxy-$C_1$-$C_6$alkyl, —$C_1$-$C_4$alkoxy$C_1$-$C_6$alkyl, —$SCF_3$, —$C_1$-$C_6$alkyl-$SO_2$, —$C_1$-$C_4$alkyl-S—$C_1$-$C_4$alkyl, —$C_1$-$C_4$alkyl-S—, —$C_1$-$C_4$alkylNR'R", and NR'R", and wherein each of the groups —$C_1$-$C_6$ alkyl, aryl, —$C_3$-$C_8$cycloalkyl, —$C_2$-$C_8$alkenyl, —$C_5$-$C_8$cycloalkenyl, —$C_1$-$C_6$ alkoxy, aryl, heterocycle may be optionally substituted by one or more of the following groups: —$C_1$-$C_6$alkyl, aryl, heterocycle, OH, halo, —$CF_3$, —$CHF_2$, —$CH_2F$, —$OCF_3$, —$OCHF_2$, —$OCH_2F$, —$O(CH_2)_nCF_3$, —CN, —$CONH_2$, —CON(H)$C_1$-$C_6$alkyl, —CON($C_1$-$C_6$alkyl)$_2$, hydroxy —$C_1$-$C_6$alkyl, —$C_1$-$C_4$alkoxy$C_1$-$C_6$alkyl, —$C_1$-$C_6$alkoxy, —$SCF_3$, —$C_1$-$C_6$alkyl$SO_2$, —$C_1$-$C_4$alkyl-S—$C_1$-$C_4$alkyl, —$C_1$-$C_4$alkyl-S—, —$C_1$-$C_4$alkylNR'R", and NR'R";

R' and R" are independently —$C_1$-$C_6$alkyl or H;

n is 1 to 5;

$R^3$ is H or F;

$R^4$ is H or F, however, when $R^3$ is F, $R^4$ is not F;

$R^5$ is H, halogen, $C_1$-$C_6$alkyl, $C_1$-$C_6$alkoxy, —S—$C_1$-$C_6$alkyl, —$(CH_2)_n$—O—$(CH_2)_n$—, —$OCF_3$, or —$SCF_3$; and

* denotes a first chiral center; and

@ denotes a second chiral center with the proviso that when $R^1$ is methyl,

—O-methyl, —O-ethyl, Cl and $R^3$-$R^8$ is H, then * and @ are either (S,R) or (R,S) and further, when $R^1$ is —O— methyl and $R^6$-$R^8$ are H, —O-methyl, Cl or methyl then * and @ are either (S,R) or R,S).

An additional aspect of this invention relates to compounds of the formula I wherein $R^1$ is $C_1$-$C_6$alkyl, halogen, OH, —CN, —S$C_1$-$C_6$alkyl, —$CH_2$O$C_1$-$C_6$alkyl, —$C_3$-$C_8$cycloalkyl, —$C_1$-$C_6$alkoxy, pyridyl, phenyl, or substituted phenyl.

A further aspect of the invention relates to compounds wherein $R^1$ is —$C_1$-$C_6$alkoxy, F, —$C_1$-$C_6$alkyl, or —CN. Other aspects relate to compounds wherein $R^3$, $R^4$, and $R^5$ are not all substituted at the same time.

Yet a further aspect of the invention relates to compounds wherein at least two of $R^3$, $R^4$, and $R^5$ are hydrogen.

Yet a further aspect of the invention relates to compounds wherein the conformation of both @ and * is S,S.

A further aspect of the invention relates to compounds of the formula III

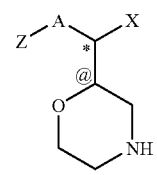

III and pharmaceutically and/or veterinarily acceptable salts or derivatives thereof, wherein:

A is O;

Z is non-phenyl heteraryl selected from pyridine, furan, thiophene, naphthalene, naphthyridine, pyrazole, pyrazine, pyrimidine, thiazole, oxazole, isoxazole, triazole, tetrazole; or a phenyl ring fused to a heterocycle containing N, O, or S; wherein each of the heteroaryls can be optionally substituted by one or more of the substituents independently selected from heterocycle, —$C_3$-$C_8$ cycloalkyl, phenyl, —$C_2$-$C_8$alkenyl, —$C_5$-$C_8$cycloalkenyl, —$(CH_2)_nC_3$-$C_8$ cycloalkyl, —$C_5$-$C_8$ fused cycloalkyl, aryl, H, —$SCF_3$, hydroxy-$C_1$-$C_6$ alkyl, —$C_1$-$C_6$ alkoxy, —O-aryl, —$(CH_2)_nS$—$C_1$-$C_6$alkyl, —$C_1$-$C_6$alkyl-$SO_2$, —$(CH_2)_n$$SO_2$—$C_1$-$C_6$alkyl, —$C_1$-$C_6$alkyl-S—, —$C_1$-$C_4$alkylNR'R", or NR'R", wherein any of the previous groups is optionally substituted by one or more substituents independently selected from —$C_1$-$C_6$ alkyl, —$C_3$-$C_8$cycloalkyl, —$C_1$-$C_6$ alkoxy, substituted or unsubstituted aryl, heterocycle, OH, halo, —$CF_3$, —$CHF_2$, —$CH_2F$, —$OCF_3$, —$OCHF_2$, —$OCH_2F$, —$O(CH_2)_nCF_3$, —CN, —CONH$_2$, —CON(H)C$_1$-C$_6$alkyl, —CON(C$_1$-C$_6$alkyl)$_2$, hydroxy-C$_1$-C$_6$alkyl, —SCF$_3$,
—C$_1$-C$_6$alkylSO$_2$, —C$_1$-C$_4$alkyl-S—C$_1$-C$_4$alkyl, —C$_1$-C$_4$alkyl-S—, —C$_1$-C$_4$, alkylNR'R", and NR'R";

X is heterocycle, aryl, C$_1$-C$_8$ alkyl, —C$_2$-C$_8$alkenyl, —C$_5$-C$_8$cycloalkenyl, benzofused bicyclic,
—C$_3$-C$_8$ cycloalkyl, —(CH$_2$)$_n$C$_3$-C$_8$ cycloalkyl, —C$_5$-C$_9$ fused cycloalkyl, H, —SCF$_3$, hydroxy-C$_1$-C$_6$ alkyl, —C$_1$-C$_6$alkoxy, —C$_1$-C$_6$alkyl, —(CH$_2$)$_n$S—C$_1$-C$_6$alkyl,
—(CH$_2$)$_n$SO$_2$—C$_1$-C$_6$alkyl, wherein each of the groups is optionally substituted by one or more substituents independently selected from —C$_1$-C$_6$ alkyl, C$_3$-C$_8$cycloalkyl, —C$_1$-C$_6$ alkoxy, aryl, heterocycle, OH, halo, —CF$_3$, —CHF$_2$, —CH$_2$F,
—OCF$_3$, —OCHF$_2$, —OCH$_2$F, —O(CH$_2$)$_n$CF$_3$, —CN, —CONH$_2$, —CON(H)C$_1$-C$_6$alkyl,
—CON(C$_1$-C$_6$alkyl)$_2$, hydroxy-C$_1$-C$_6$alkyl, —SCF$_3$, —C$_1$-C$_6$alkylSO$_2$, —C$_1$-C$_4$alkyl-S —C$_1$-C$_4$alkyl, —C$_1$-C$_4$alkyl-S—, —C$_1$-C$_4$alkylNR'R", and NR'R";
R' and R" are independently C$_1$-C$_6$alkyl or H;
n is 1 to 5;
* denotes a first chiral center; and
@ denotes a second chiral center.

A further aspect of the invention relates to compounds wherein Z is pyridyl.

Yet a further aspect of the invention relates to compounds wherein the conformation of both @ and * is S,S.

Compounds of the invention include the following compounds and their pharmaceutically acceptable salts, enantiomers and diastereomers:

2-[Phenyl-(2-trifluoromethoxy-phenoxy)-methyl]-morpholine;
2-[(2-Ethylsulfanyl-phenoxy)-phenyl-methyl]-morpholine;
2-[(2-Isobutyl-phenoxy)-phenyl-methyl]-morpholine;
2-[(2-Bromo-phenoxy)-phenyl-methyl]-morpholine;
2-[Phenyl-(2-vinyl-phenoxy)-methyl]-morpholine;
2-[(2-Chloro-phenoxy)-phenyl-methyl]-morpholine;
2-[(2-Methoxymethyl-phenoxy)-phenyl-methyl]-morpholine;
2-[Phenyl-(2-trifluoromethyl-phenoxy)-methyl]-morpholine;
2-[(2-Benzyl-phenoxy)-phenyl-methyl]-morpholine;
2-[Phenyl-(2-pyridin-4-yl-phenoxy)-methyl]-morpholine;
2-[(2-Cyclopropyl-phenoxy)-phenyl-methyl]-morpholine;
2-[(Naphthalen-1-yloxy)-phenyl-methyl]-morpholine;
2-[Phenyl-(2-pyridin-3-yl-phenoxy)-methyl]-morpholine;
2-[(2-Phenoxy-phenoxy)-phenyl-methyl]-morpholine;
2-(Morpholin-2-yl-phenyl-methoxy)-benzoic acid ethyl ester;
2-[(4'-Chloro-biphenyl-2-yloxy)-phenyl-methyl]-morpholine;
2-(2-Ethoxy-phenoxymethyl)-morpholine;
2-[(2-Fluoro-phenoxy)-phenyl-methyl]-morpholine;
2-[(2-Chloro-4-fluoro-phenoxy)-pyridin-3-yl-methyl]-morpholine;
2-[(2-Ethoxy-phenoxy)-pyridin-2-yl-methyl]-morpholine;
2-(Morpholin-2-yl-pyridin-2-yl-methoxy)-benzonitrile;
2-[(2-Fluorophenoxy)-pyridin-3-yl-methyl]-morpholine;
2-(Morpholin-2-yl-pyridin-3-yl-methoxy)-benzonitrile;
2-[(2-Ethoxy-phenoxy)-pyridin-3-yl-methyl]-morpholine;
2-[Pyridin-3-yl-(2-trifluoromethoxy-phenoxy)-methyl]-morpholine;
2-[(2-,4-Difluoro-phenoxy)-pyridin-3-yl-methyl]-morpholine;
2-[(1-Oxy-pyridin-2-yloxy)-phenyl-methyl]-morpholine;
2-[(2'-Chloro-biphenyl-2-yloxy)-phenyl-methyl]-morpholine;
(2-Fluoro-6-methoxy-phenoxy)-pyridin-3-yl-methyl]-morpholine;
2-[(2-Fluoro-6-methoxy-phenoxy)-pyridin-3-yl-methyl]-morpholine;
2-[2-(4-Fluoro-phenoxy)-pyridin-3-yloxymethyl]-morpholine;
2-{[2-(4-Fluoro-phenyl)-pyridin-3-yloxy]-phenyl-methyl}-morpholine;
2-[(2-Fluoro-phenoxy)-(4-fluoro-phenyl)-methyl]-morpholine;
2-[(2-Fluoro-phenoxy)-(4-fluoro-phenyl)-methyl]-morpholine;
2-[(2,6-Difluoro-phenoxy)-phenyl-methyl]-morpholine;
2-[2-Cyclohexyl-1-(2-ethoxy-phenoxy)-ethyl]-morpholine;
2-[1-(2-Ethoxy-phenoxy)-3-methyl-butyl]-morpholine;
2-[(2-Allyl-phenoxy)-phenyl-methyl]-morpholine;
2-[Phenyl-(pyridin-3-yloxy)-methyl]-morpholine;
2-[(2-Bromo-pyridin-3-yloxy)-phenyl-methyl]-morpholine;
2-[Phenyl-(2-p-tolyl-pyridin-3-yloxy)-methyl]-morpholine;
2-[(2-Chloro-phenoxy)-phenyl-methyl]-morpholine;
2-[(2-Isopropyl-phenoxy)-phenyl-methyl]-morpholine;
2-[(Benzofuran-6-yloxy)-phenyl-methyl]-morpholine;
2-[(2-Isopropoxy-phenoxy)-phenyl-methyl]-morpholine;
2-[(2-Bromo-phenoxy)-(4-fluoro-phenyl)-methyl]-morpholine;
2-[(Benzofuran-5-yloxy)-phenyl-methyl]-morpholine;
2-(Phenyl-o-tolyloxy-methyl)-morpholine;
2-(Morpholin-2-yl-phenyl-methoxy)-phenol;
2-[Cyclohexyl-(2-ethoxy-phenoxy)-methyl]-morpholine;
2-[Phenyl-(2-piperazin-1-yl-phenoxy)-methyl]-morpholine;
2-[(2-Methylsulfanyl-phenoxy)-phenyl-methyl]-morpholine;
2-[(2-Methanesulfonyl-phenoxy)-phenyl-methyl]-morpholine;
2-[(2-Cyclopentyl-phenoxy)-phenyl-methyl]-morpholine;
2-[(2-Cyclohexyl-phenoxy)-phenyl-methyl]-morpholine;
2-[(2-Difluoromethoxy-phenoxy)-phenyl-methyl]-morpholine;
2-{[2-(2-Fluoro-ethoxy)-phenoxy]-phenyl-methyl}-morpholine;
2-[(4-Fluoro-2-isobutyl-phenoxy)-phenyl-methyl]-morpholine;
2-[(2-Chloro-6-fluoro-phenoxy)-phenyl-methyl]-morpholine;
2-[(2-Cyclopropylmethyl-phenoxy)-phenyl-methyl]-morpholine;
2-[(2,6-Dichloro-phenoxy)-phenyl-methyl]-morpholine;
2-[(2-Ethoxymethyl-phenoxy)-phenyl-methyl]-morpholine;
Dimethyl-[2-(morpholin-2-yl-phenyl-methoxy)-phenyl]-amine;
2-{[2-(4-Fluoro-phenoxy)-pyridin-3-yloxy]-phenyl-methyl}-morpholine;
2-[(2,6-Difluoro-phenoxy)-(4-fluoro-phenyl)-methyl]-morpholine;

2-[(2-Bromo-phenoxy)-phenyl-methyl]-morpholine;
2-[(2,4-Difluoro-phenoxy)-phenyl-methyl]-morpholine;
2-[(4-Fluoro-phenoxy)-phenyl-methyl]-morpholine;
2-[(2-Ethoxy-phenoxy)-(3-fluoro-phenyl)-methyl]-morpholine;
2-[(2-Cyclopropyl-phenoxy)-phenyl-methyl]-morpholine;
2-(2-Phenoxy-phenoxymethyl)-morpholine;
2-(2'-Chloro-biphenyl-2-yloxymethyl)-morpholine;
2-(2'-Methoxy-biphenyl-2-yloxymethyl)-morpholine;
2-(5-Fluoro-4'-methyl-biphenyl-2-yloxymethyl)-morpholine;
2-(5,4'-Difluoro-biphenyl-2-yloxymethyl)-morpholine;
2-(2-Phenoxy-pyridin-3-yloxymethyl)-morpholine;
2-[3-(4-Fluoro-phenoxy)-pyrazin-2-yloxymethyl]-morpholine;
2-[2-(3,4-Difluoro-phenoxy)-pyridin-3-yloxymethyl]-morpholine;
2-(Phenoxy-phenyl-methyl)-morpholine;
2-[(4'-Fluoro-biphenyl-2-yloxy)-phenyl-methyl]-morpholine;
2-[(4'-Methyl-biphenyl-2-yloxy)-phenyl-methyl]-morpholine;
2-[(2-Benzyloxy-phenoxy)-phenyl-methyl]-morpholine;
2-[(2-Fluoro-phenoxy)-phenyl-methyl]-morpholine;
[2-(Morpholin-2-yl-phenyl-methoxy)-phenyl]-methanol;
2-[(2'-Fluoro-biphenyl-2-yloxy)-phenyl-methyl]-morpholine;
2-[(2,4-Difluoro-phenoxy)-pyridin-2-yl-methyl]-morpholine;
2-(2'-Methyl-biphenyl-2-yloxymethyl)-morpholine;
2-[2-(4-Fluoro-phenoxy)-pyridin-3-yloxymethyl]-morpholine;
2-[(2-Ethoxy-phenoxy)-pyridin-3-yl-methyl]-morpholine;
2-[(2-Ethoxy-phenoxy)-phenyl-methyl]-morpholine;
2-[(2-Ethoxy-phenoxy)-phenyl-methyl]-morpholine;
2-[morpholin-2-yl(phenyl)methoxy]benzonitrile;
2-[(2-chloro-5-fluorophenoxy) (phenyl)methyl]morpholine;
2-[(2-fluoro-6-methoxyphenoxy)(phenyl)methyl]morpholine;
2-[(2,5-difluorophenoxy)(phenyl)methyl]morpholine;
2-[phenyl(2-propylphenoxy)methyl]morpholine;
2-[(2-ethylphenoxy)(phenyl)methyl]morpholine;
2-[cyclopropyl(2,4-difluorophenoxy)methyl]morpholine;
2-[(2-ethoxyphenoxy)(1-oxidopyridin-2-yl)methyl]morpholine;
2-[1-(2,6-difluorophenoxy)-2-phenylethyl]morpholine;
2-[[2-(benzyloxy)phenoxy](pyridin-2-yl)methyl]morpholine;
2-[(2-isopropylphenoxy)(pyridin-2-yl)methyl]morpholine;
2-[1-(2-ethoxyphenoxy)butyl]morpholine;
2-[1-(2-ethoxyphenoxy)-3-methylbutyl]morpholine;
2-[(2,3-difluorophenoxy)(3-fluorophenyl)methyl]morpholine;
2-[(2-ethoxyphenoxy)(6-methylpyridin-2-yl)methyl]morpholine;
2-[(2-ethoxyphenoxy)(6-methoxypyridin-2-yl)methyl]morpholine;
2-{(6-methoxypyridin-2-yl)[2-(trifluoromethoxy)phenoxy]methyl}morpholine;
2-[(2,3-dihydro-1H-inden-4-yloxy)(pyridin-2-yl)methyl]morpholine;
2-[(2,6-difluorophenoxy)(4-fluorophenyl)methyl]morpholine;

2-[(2-bromophenoxy)(phenyl)methyl]morpholine;
2-[(2-chloro-6-fluorophenoxy)(phenyl)methyl]morpholine;
2-[(2-cyclopropylphenoxy)(phenyl)methyl]morpholine;
N,N,N-trimethyl-2-[morpholin-2-yl(phenyl)methoxy]benzenaminium;
2-[{[2-(4-fluorophenoxy)pyridin-3-yl]oxy}(phenyl)methyl]morpholine;
2-[(2-bromo-4-fluorophenoxy)(phenyl)methyl]morpholine;
2-[cyclopropyl(2-ethoxyphenoxy)methyl]morpholine;
2-[(2-cyclopropyl-4-fluorophenoxy) (phenyl)methyl]morpholine;
2-[[2-fluorophenoxy)](pyridin-2-yl)methyl]morpholine;
2-[(2-cyclopropyl-4,6-difluorophenoxy)(phenyl)methyl]morpholine;
2-[(2-ethoxyphenoxy)(4-methyl-1,3-oxazol-2-yl)methyl]morpholine;
2-[[(2-ethylpyridin-3-yl)oxy](phenyl)methyl]morpholine;
2-[morpholin-2-yl(pyridin-2-yl)methoxy]benzonitrile;
2-[(2-isopropoxyphenoxy)(pyridin-2-yl)methyl]morpholine;
2-[(2-propylphenoxy)(pyridin-2-yl)methyl]morpholine;
2-[(2-benzylphenoxy)(pyridin-2-yl)methyl]morpholine;
2-{pyridin-2-yl[2-(trifluoromethoxy)phenoxy]methyl}morpholine;
2-[(2-isopropyl-5-methylphenoxy)(pyridin-2-yl)methyl]morpholine;
2-[[(2-methylpyridin-3-yl)oxy](phenyl)methyl]morpholine;
2-[(2-cyclopentylphenoxy)(pyridin-2-yl)methyl]morpholine;
2-{pyridin-2-yl[2-(trifluoromethyl)phenoxy]methyl}morpholine;
2-[(2,6-difluorophenoxy)(4-methyl-1,3-oxazol-2-yl)methyl]morpholine;
2-{phenyl[(2-propylpyridin-3-yl)oxy]methyl}morpholine;
2-{1-[(2-ethoxypyridin-3-yl)oxy]propyl}morpholine;
2-[[(2-ethoxypyridin-3-yl)oxy](phenyl)methyl]morpholine;
2-[(2-ethoxyphenoxy)(3-methylpyridin-2-yl)methyl]morpholine;
2-{(3-methylpyridin-2-yl)[2-(trifluoromethoxy)phenoxy]methyl}morpholine;
2-[(2-isopropoxyphenoxy)(6-methoxypyridin-2-yl)methyl]morpholine;
2-[(4-ethylpyridin-2-yl)(2-fluoro-6-methoxyphenoxy)methyl]morpholine;
2-[(2-ethoxyphenoxy)(4-ethylpyridin-2-yl)methyl]morpholine;
2-[1-benzofuran-2-yl(2,6-difluorophenoxy)methyl]morpholine;
2-{1-[(2-ethoxypyridin-3-yl)oxy]ethyl}morpholine;
2-[[2-(3-fluoropropyl)phenoxy](phenyl)methyl]morpholine;
2-[cyclopent-1-en-1-yl(2,6-difluorophenoxy)methyl]morpholine;
2-[(2,6-dimethoxyphenoxy)(phenyl)methyl]morpholine;
2-{1-[(2-ethoxypyridin-3-yl)oxy]-3-methylbutyl}morpholine;
2-[[(2-cyclopropylpyridin-3-yl)oxy](phenyl)methyl]morpholine;
2-{1-[2-(4-fluorophenoxy)phenoxy]ethyl}morpholine;
2-[(2-chloro-5-fluorophenoxy)(pyridin-2-yl)methyl]morpholine;

2-[(biphenyl-2-yloxy)(pyridin-2-yl)methyl]morpholine;
2-[(2-cyclopropylphenoxy)(pyridin-2-yl)methyl]morpholine;
2-[(2-bromophenoxy)(pyridin-2-yl)methyl]morpholine;
2-[[2-(fluoromethyl)phenoxy](phenyl)methyl]morpholine;
2-[(2-ethoxy-6-fluorophenoxy)(phenyl)methyl]morpholine;
2-[(2-fluoro-6-methoxyphenoxy)(pyridin-2-yl)methyl]morpholine;
2-[(2-ethoxy-6-fluorophenoxy)(pyridin-2-yl)methyl]morpholine;
2-[(2,6-difluorophenoxy)(pyridin-2-yl)methyl]morpholine;
2-[[2-(3-fluoropropoxy)phenoxy](phenyl)methyl]morpholine;
2-{2-cyclohexyl-1-[(2-ethoxypyridin-3-yl)oxy]ethyl}morpholine;
2-[(2,6-difluorophenoxy)(2,3-dihydro-1-benzofuran-7-yl)methyl]morpholine;
2-[(2-cyclopropyl-5-fluorophenoxy)(pyridin-2-yl)methyl]morpholine;
2-[(2-fluoro-6-isopropoxyphenoxy)(phenyl)methyl]morpholine;
2-[[(2-methoxypyridin-3-yl)oxy](phenyl)methyl]morpholine;
2-[(5-fluoro-2-methoxyphenoxy)(phenyl)methyl]morpholine;
2-[(3-fluoro-2-methoxyphenoxy)(phenyl)methyl]morpholine;
2-[(2-ethoxy-5-fluorophenoxy)(phenyl)methyl]morpholine;
2-[(2-ethoxy-3-fluorophenoxy)(phenyl)methyl]morpholine;
2-[(2-fluoro-6-propoxyphenoxy)(phenyl)methyl]morpholine;
2-[(2-ethoxyphenoxy)(4-methyl-1,3-oxazol-2-yl)methyl]morpholine;
2-[(2,6-difluorophenoxy)(4-methyl-1,3-oxazol-2-yl)methyl]morpholine;
2-{(4-methyl-1,3-oxazol-2-yl)[2-(trifluoromethoxy)phenoxy]methyl}morpholine;
2-[(2,6-difluorophenoxy)(1,3-thiazol-2-yl)methyl]morpholine;
2-{1-[(2-ethoxypyridin-3-yl)oxy]pentyl}morpholine;
2-[(2-bromophenoxy)(4-methyl-1,3-oxazol-2-yl)methyl]morpholine;
2-[(2-fluoro-6-methylphenoxy)(phenyl)methyl]morpholine;
2-[[(2-isopropylpyridin-3-yl)oxy](phenyl)methyl]morpholine;
2-[(2-ethoxyphenoxy)(1,3-thiazol-2-yl)methyl]morpholine;
2-[(2-ethoxyphenoxy)(pyridin-2-yl)methyl]morpholine;
2-[[(2-isobutylpyridin-3-yl)oxy](phenyl)methyl]morpholine;
2-[(2-fluoro-6-isopropylphenoxy)(phenyl)methyl]morpholine;
2-[(2-cyclopropyl-6-fluorophenoxy)(phenyl)methyl]morpholine;
2-[(2-bromo-6-fluorophenoxy)(6-methoxypyridin-2-yl)methyl]morpholine;
2-[(2-bromo-6-fluorophenoxy)(pyridin-2-yl)methyl]morpholine;
2-[(2-bromophenoxy)(6-methoxypyridin-2-yl)methyl]morpholine;
2-[(2-fluoro-6-methoxyphenoxy)(6-methoxypyridin-2-yl)methyl]morpholine;
2-{1-[(2-ethoxypyridin-3-yl)oxy]-2-methylpropyl}morpholine;
2-[(2-cyclopropylphenoxy)(4-methyl-1,3-oxazol-2-yl)methyl]morpholine;
2-{1-[(2-ethoxypyridin-3-yl)oxy]butyl}morpholine;
2-[{[2-(cyclopropylmethoxy)pyridin-3-yl]oxy}(phenyl)methyl]morpholine;
2-[[2-fluoro-6-(trifluoromethyl)phenoxy](phenyl)methyl]morpholine;
2-[[2-fluoro-6-(trifluoromethoxy)phenoxy](phenyl)methyl]morpholine;
2-[(2-ethoxyphenoxy)(1,3-oxazol-2-yl)methyl]morpholine;
2-[(2,6-difluorophenoxy)(1,3-oxazol-2-yl)methyl]morpholine;
2-{1-[(2-ethoxypyridin-3-yl)oxy]-2-phenylethyl}morpholine;
2-[[4-fluoro-2-(methylthio)phenoxy](phenyl)methyl]morpholine;
2-[(2,6-difluorophenoxy)(6-methoxypyridin-2-yl)methyl]morpholine;
2,2'-[pyrazine-2,3-diylbis(oxymethylene)]dimorpholine;
2-[2-Ethoxy-pyridin-3-yloxymethyl]-morpholine; and
2-[(2-fluoro-6-methoxyphenoxy)(pyridin-3-yl)methyl]morpholine.

Compounds of the invention also include the following compounds and their pharmaceutically acceptable salts, enantiomers and diastereomers:

(S)-2-[(S)-Phenyl-(2-trifluoromethoxy-phenoxy)-methyl]-morpholine;
(S)-2-[(S)-(2-Ethylsulfanyl-phenoxy)-phenyl-methyl]-morpholine;
(S)-2-[(S)-(2-Isobutyl-phenoxy)-phenyl-methyl]-morpholine;
(S)-2-[(S)-(2-Bromo-phenoxy)-phenyl-methyl]-morpholine;
(S)-2-[(S)-Phenyl-(2-vinyl-phenoxy)-methyl]-morpholine;
(S)-2-[(S)-(2-Chloro-phenoxy)-phenyl-methyl]-morpholine;
(S)-2-[(S)-(2-Methoxymethyl-phenoxy)-phenyl-methyl]-morpholine;
(S)-2-[(S)-Phenyl-(2-trifluoromethyl-phenoxy)-methyl]-morpholine;
(S)-2-[(S)-(2-Benzyl-phenoxy)-phenyl-methyl]-morpholine;
(S)-2-[(S)-Phenyl-(2-pyridin-4-yl-phenoxy)-methyl]-morpholine;
(S)-2-[(S)-(2-Cyclopropyl-phenoxy)-phenyl-methyl]-morpholine;
(S)-2-[(S)-(Naphthalen-1-yloxy)-phenyl-methyl]-morpholine;
(S)-2-[(S)-Phenyl-(2-pyridin-3-yl-phenoxy)-methyl]-morpholine;
(S)-2-[(S)-(2-Phenoxy-phenoxy)-phenyl-methyl]-morpholine;
(2S,3S)-2-(Morpholin-2-yl-phenyl-methoxy)-benzoic acid ethyl ester;
(S)-2-[((S)-4'-Chloro-biphenyl-2-yloxy)-phenyl-methyl]-morpholine;
(S)-2-(2-Ethoxy-phenoxymethyl)-morpholine;
(R)-2-[(S)-(2-Fluoro-phenoxy)-phenyl-methyl]-morpholine;
(S)-2-[(R)-(2-Chloro-4-fluoro-phenoxy)-pyridin-3-yl-methyl]-morpholine;

(S)-2-[(R)-(2-Ethoxy-phenoxy)-pyridin-2-yl-methyl]-morpholine;
(S)-2-[(S)-(2-Ethoxy-phenoxy)-pyridin-2-yl-methyl]-morpholine;
(2S,3S)-2-(Morpholin-2-yl-pyridin-2-yl-methoxy)-benzonitrile;
(2S,3R)-2-(Morpholin-2-yl-pyridin-2-yl-methoxy)-benzonitrile;
(S)-2-[(S)-(2-Fluorophenoxy)-pyridin-3-yl-methyl]-morpholine;
(2S,3R)-2-(Morpholin-2-yl-pyridin-3-yl-methoxy)-benzonitrile;
(2R,3R)-2-[(2-Ethoxy-phenoxy)-pyridin-3-yl-methyl]-morpholine;
(2S,3R)-2-[(2-Ethoxy-phenoxy)-pyridin-3-yl-methyl]-morpholine;
(R)-2-[(S)-Pyridin-3-yl-(2-trifluoromethoxy-phenoxy)-methyl]-morpholine;
(R)-2-[(S)-(2-,4-Difluoro-phenoxy)-pyridin-3-yl-methyl]-morpholine;
(R)-2-[(R)-(2-,4-Difluoro-phenoxy)-pyridin-3-yl-methyl]-morpholine;
(S)-2-[((S)-1-Oxy-pyridin-2-yloxy)-phenyl-methyl]-morpholine;
(S)-2-[(S)-(2'-Chloro-biphenyl-2-yloxy)-phenyl-methyl]-morpholine;
(2R,3R)-(2-Fluoro-6-methoxy-phenoxy)-pyridin-3-yl-methyl]-morpholine;
(R)-2-[(S)-(2-Fluoro-6-methoxy-phenoxy)-pyridin-3-yl-methyl]-morpholine;
(S)-2-[2-(4-Fluoro-phenoxy)-pyridin-3-yloxymethyl]-morpholine;
(S)-2-{(S)-[2-(4-Fluoro-phenyl)-pyridin-3-yloxy]-phenyl-methyl}-morpholine;
(R)-2-[(S)-(2-Fluoro-phenoxy)-(4-fluoro-phenyl)-methyl]-morpholine;
(R)-2-[(S)-(2-Fluoro-phenoxy)-(4-fluoro-phenyl)-methyl]-morpholine;
(S)-2-[(S)-(2,6-Difluoro-phenoxy)-phenyl-methyl]-morpholine;
(S)-2-[(S)-2-Cyclohexyl-1-(2-ethoxy-phenoxy)-ethyl]-morpholine;
(2S,3-R)-2-[2-Cyclohexyl-1-(2-ethoxy-phenoxy)-ethyl]-morpholine;
(S)-2-[(S)-1-(2-Ethoxy-phenoxy)-3-methyl-butyl]-morpholine;
(S)-2-[(S)-(2-Allyl-phenoxy)-phenyl-methyl]-morpholine;
(S)-2-[(S)-Phenyl-(pyridin-3-yloxy)-methyl]-morpholine;
(S)-2-[(S)-(2-Bromo-pyridin-3-yloxy)-phenyl-methyl]-morpholine;
(S)-2-[(S)-Phenyl-(2-p-tolyl-pyridin-3-yloxy)-methyl]-morpholine;
(S)-2-[(S)-(2-Chloro-phenoxy)-phenyl-methyl]-morpholine;
(S)-2-[(S)-(2-Isopropyl-phenoxy)-phenyl-methyl]-morpholine;
(R)-2-[(S)-(Benzofuran-6-yloxy)-phenyl-methyl]-morpholine;
(S)-2-[(S)-(2-Isopropoxy-phenoxy)-phenyl-methyl]-morpholine;
(R)-2-[(S)-(2-Bromo-phenoxy)-(4-fluoro-phenyl)-methyl]-morpholine;
(S)-2-[(S)-(Benzofuran-5-yloxy)-phenyl-methyl]-morpholine;
(S)-2-((S)-Phenyl-o-tolyloxy-methyl)-morpholine;
(2S,3S)-2-(Morpholin-2-yl-phenyl-methoxy)-phenol;
(S)-2-[(S)-Cyclohexyl-(2-ethoxy-phenoxy)-methyl]-morpholine;
(S)-2-[(S)-Phenyl-(2-piperazin-1-yl-phenoxy)-methyl]-morpholine;
(S)-2-[(S)-(2-Methylsulfanyl-phenoxy)-phenyl-methyl]-morpholine;
(S)-2-[(S)-(2-Methanesulfonyl-phenoxy)-phenyl-methyl]-morpholine;
(S)-2-[(S)-(2-Cyclopentyl-phenoxy)-phenyl-methyl]-morpholine;
(S)-2-[(S)-(2-Cyclohexyl-phenoxy)-phenyl-methyl]-morpholine;
(S)-2-[(S)-(2-Difluoromethoxy-phenoxy)-phenyl-methyl]-morpholine;
(S)-2-{(S)-[2-(2-Fluoro-ethoxy)-phenoxy]-phenyl-methyl}-morpholine;
(S)-2-[(S)-(4-Fluoro-2-isobutyl-phenoxy)-phenyl-methyl]-morpholine;
(S)-2-[(S)-(2-Chloro-6-fluoro-phenoxy)-phenyl-methyl]-morpholine;
(S)-2-[(S)-(2-Cyclopropylmethyl-phenoxy)-phenyl-methyl]-morpholine;
(S)-2-[(S)-(2,6-Dichloro-phenoxy)-phenyl-methyl]-morpholine;
(S)-2-[(S)-(2-Ethoxymethyl-phenoxy)-phenyl-methyl]-morpholine;
(2S,3S)-Dimethyl-[2-(morpholin-2-yl-phenyl-methoxy)-phenyl]-amine;
(S)-2-{(S)-[2-(4-Fluoro-phenoxy)-pyridin-3-yloxy]-phenyl-methyl}-morpholine;
(R)-2-[(S)-(2,6-Difluoro-phenoxy)-(4-fluoro-phenyl)-methyl]-morpholine;
(R)-2-[(S)-(2-Bromo-phenoxy)-phenyl-methyl]-morpholine;
(S)-2-[(S)-(2,4-Difluoro-phenoxy)-phenyl-methyl]-morpholine;
(S)-2-[(S)-(4-Fluoro-phenoxy)-phenyl-methyl]-morpholine;
(R)-2-[(S)-(2-Ethoxy-phenoxy)-(3-fluoro-phenyl)-methyl]-morpholine;
(R)-2-[(S)-(2-Cyclopropyl-phenoxy)-phenyl-methyl]-morpholine;
(S)-2-(2-Phenoxy-phenoxymethyl)-morpholine;
(R)-2-(5-Fluoro-4'-methyl-biphenyl-2-yloxymethyl)-morpholine;
(S)-2-(5-Fluoro-4'-methyl-biphenyl-2-yloxymethyl)-morpholine;
(R)-2-(5,4'-Difluoro-biphenyl-2-yloxymethyl)-morpholine;
(S)-2-(5,4'-Difluoro-biphenyl-2-yloxymethyl)-morpholine;
(R)-2-(2-Phenoxy-pyridin-3-yloxymethyl)-morpholine;
(S)-2-[3-(4-Fluoro-phenoxy)-pyrazin-2-yloxymethyl]-morpholine;
(S)-2-[2-(3,4-Difluoro-phenoxy)-pyridin-3-yloxymethyl]-morpholine;
(S)-2-((S)-Phenoxy-phenyl-methyl)-morpholine;
(S)-2-[(S)-(4'-Fluoro-biphenyl-2-yloxy)-phenyl-methyl]-morpholine;
(S)-2-[(S)-(4'-Methyl-biphenyl-2-yloxy)-phenyl-methyl]-morpholine;
(S)-2-[(S)-(2-Benzyloxy-phenoxy)-phenyl-methyl]-morpholine;
(S)-2-[(S)-(2-Fluoro-phenoxy)-phenyl-methyl]-morpholine;

(2S,3S)-[2-(Morpholin-2-yl-phenyl-methoxy)-phenyl]-methanol;
(S)-2-[(S)-(2'-Fluoro-biphenyl-2-yloxy)-phenyl-methyl]-morpholine;
(2R,3R)-2-[(2,4-Difluoro-phenoxy)-pyridin-2-yl-methyl]-morpholine;
(2R)-2-[2-(4-Fluoro-phenoxy)-pyridin-3-yloxymethyl]-morpholine;
(2R)-2-[(R)-(2-Ethoxy-phenoxy)-pyridin-3-yl-methyl]-morpholine;
(R)-2-[(S)-(2-Ethoxy-phenoxy)-phenyl-methyl]-morpholine;
(S)-2-[(R)-(2-Ethoxy-phenoxy)-phenyl-methyl]-morpholine;
2-[(S)-(2S)-morpholin-2-yl(phenyl)methoxy]benzonitrile;
(2S)-2-[(2-chloro-5-fluorophenoxy)(phenyl)methyl]morpholine;
(2S)-2-[(2-fluoro-6-methoxyphenoxy)(phenyl)methyl]morpholine;
(2S)-2-[(S)-(2,5-difluorophenoxy)(phenyl)methyl]morpholine;
(2S)-2-[(S)-phenyl(2-propylphenoxy)methyl]morpholine;
(2S)-2-[(S)-(2-ethylphenoxy)(phenyl)methyl]morpholine;
(2S)-2-[cyclopropyl(2,4-difluorophenoxy)methyl]morpholine;
(2S)-2-[(S)-(2-ethoxyphenoxy)(1-oxidopyridin-2-yl)methyl]morpholine;
(2S)-2-[1-(2,6-difluorophenoxy)-2-phenylethyl]morpholine;
(2S)-2-[(S)-[2-(benzyloxy)phenoxy](pyridin-2-yl)methyl]morpholine;
(2S)-2-[(S)-(2-isopropylphenoxy)(pyridin-2-yl)methyl]morpholine;
(2S)-2-[(1S)-1-(2-ethoxyphenoxy)butyl]morpholine;
(2S)-2-[(1S)-1-(2-ethoxyphenoxy)-3-methylbutyl]morpholine;
(2S)-2-[(S)-(2,3-difluorophenoxy)(3-fluorophenyl)methyl]morpholine;
(2S)-2-[(R)-(2,3-difluorophenoxy)(3-fluorophenyl)methyl]morpholine;
(2S)-2-[(S)-(2-ethoxyphenoxy)(6-methylpyridin-2-yl)methyl]morpholine;
(2S)-2-[(S)-(2-ethoxyphenoxy)(6-methoxypyridin-2-yl)methyl]morpholine;
(2S)-2-{(S)-(6-methoxypyridin-2-yl)[2-(trifluoromethoxy)phenoxy]methyl}morpholine;
(2S)-2-[(S)-(2,3-dihydro-1H-inden-4-yloxy)(pyridin-2-yl)methyl]morpholine;
(2R)-2-[(2,6-difluorophenoxy)(4-fluorophenyl)methyl]morpholine;
(2R)-2-[(2-bromophenoxy)(phenyl)methyl]morpholine;
(2S)-2-[(S)-(2-chloro-6-fluorophenoxy)(phenyl)methyl]morpholine;
(2R)-2-[(2-cyclopropylphenoxy)(phenyl)methyl]morpholine;
N,N,N-trimethyl-2-[(S)-(2S)-morpholin-2-yl(phenyl)methoxy]benzenaminium;
(2S)-2-[(S)-{[2-(4-fluorophenoxy)pyridin-3-yl]oxy}(phenyl)methyl]morpholine;
(2S)-2-[(S)-(2-bromo-4-fluorophenoxy)(phenyl)methyl]morpholine;
(2S)-2-[cyclopropyl(2-ethoxyphenoxy)methyl]morpholine;
(2S)-2-[(S)-(2-cyclopropyl-4-fluorophenoxy)(phenyl)methyl]morpholine;
(2S)-2-[(S)-[2-fluorophenoxy)](pyridin-2-yl)methyl]morpholine;
(2S)-2-[(R)-[2-fluorophenoxy)](pyridin-2-yl)methyl]morpholine;
2S)-2-[(S)-(2-cyclopropyl-4,6-difluorophenoxy)(phenyl)methyl]morpholine;
(2S)-2-[(2-ethoxyphenoxy)(4-methyl-1,3-oxazol-2-yl)methyl]morpholine;
(2S)-2-[(S)-[(2-ethylpyridin-3-yl)oxy](phenyl)methyl]morpholine;
2-[(S)-(2S)-morpholin-2-yl(pyridin-2-yl)methoxy]benzonitrile;
(2S)-2-[(S)-(2-isopropoxyphenoxy)(pyridin-2-yl)methyl]morpholine;
(2S)-2-[(S)-(2-propylphenoxy)(pyridin-2-yl)methyl]morpholine;
(2S)-2-[(S)-(2-benzylphenoxy)(pyridin-2-yl)methyl]morpholine;
(2S)-2-{(S)-pyridin-2-yl[2-(trifluoromethoxy)phenoxy]methyl}morpholine;
(2S)-2-[(S)-(2-isopropyl-5-methylphenoxy)(pyridin-2-yl)methyl]morpholine;
(2S)-2-[(S)-[(2-methylpyridin-3-yl)oxy](phenyl)methyl]morpholine;
(2S)-2-[(S)-(2-cyclopentylphenoxy)(pyridin-2-yl)methyl]morpholine;
(2S)-2-{(S)-pyridin-2-yl[2-(trifluoromethyl)phenoxy]methyl}morpholine;
(2S)-2-[(2,6-difluorophenoxy)(4-methyl-1,3-oxazol-2-yl)methyl]morpholine;
(2S)-2-{(S)-phenyl[(2-propylpyridin-3-yl)oxy]methyl}morpholine;
(2S)-2-{1-[(2-ethoxypyridin-3-yl)oxy]propyl}morpholine;
(2S)-2-[(S)-[(2-ethoxypyridin-3-yl)oxy](phenyl)methyl]morpholine;
(2S)-2-[(S)-(2-ethoxyphenoxy)(3-methylpyridin-2-yl)methyl]morpholine;
(2S)-2-{(S)-(3-methylpyridin-2-yl)[2-(trifluoromethoxy)phenoxy]methyl}morpholine;
(2S)-2-[(S)-(2-isopropoxyphenoxy)(6-methoxypyridin-2-yl)methyl]morpholine;
(2S)-2-[(S)-(4-ethylpyridin-2-yl)(2-fluoro-6-methoxyphenoxy)methyl]morpholine;
(2S)-2-[(S)-(2-ethoxyphenoxy)(4-ethylpyridin-2-yl)methyl]morpholine;
(2S)-2-[1-benzofuran-2-yl(2,6-difluorophenoxy)methyl]morpholine;
(2S)-2-{(1S)-1-[(2-ethoxypyridin-3-yl)oxy]ethyl}morpholine;
(2S)-2-[(S)-[2-(3-fluoropropyl)phenoxy](phenyl)methyl]morpholine;
(2S)-2-[(S)-cyclopent-1-en-1-yl(2,6-difluorophenoxy)methyl]morpholine;
(2S)-2-[(R)-cyclopent-1-en-1-yl(2,6-difluorophenoxy)methyl]morpholine;
(2S)-2-[(2,6-dimethoxyphenoxy)(phenyl)methyl]morpholine;
(2S)-2-{1-[(2-ethoxypyridin-3-yl)oxy]-3-methylbutyl}morpholine;
(2S)-2-[(S)-[(2-cyclopropylpyridin-3-yl)oxy](phenyl)methyl]morpholine;
(2S)-2-{1-[2-(4-fluorophenoxy)phenoxy]ethyl}morpholine;

(2S)-2-[(S)-(2-chloro-5-fluorophenoxy)(pyridin-2-yl)methyl]morpholine;
(2S)-2-[(S)-(biphenyl-2-yloxy)(pyridin-2-yl)methyl]morpholine;
(2S)-2-[(S)-(2-cyclopropylphenoxy)(pyridin-2-yl)methyl]morpholine;
(2S)-2-[(S)-(2-bromophenoxy)(pyridin-2-yl)methyl]morpholine;
(2S)-2-[[2-(fluoromethyl)phenoxy](phenyl)methyl]morpholine;
(2S)-2-[(2-ethoxy-6-fluorophenoxy)(phenyl)methyl]morpholine;
(2S)-2-[(S)-(2-fluoro-6-methoxyphenoxy)(pyridin-2-yl)methyl]morpholine;
(2S)-2-[(S)-(2-ethoxy-6-fluorophenoxy)(pyridin-2-yl)methyl]morpholine;
(2S)-2-[(S)-(2,6-difluorophenoxy)(pyridin-2-yl)methyl]morpholine;
(2S)-2-[(S)-[2-(3-fluoropropoxy)phenoxy](phenyl)methyl]morpholine;
(2S)-2-{(1S)-2-cyclohexyl-1-[(2-ethoxypyridin-3-yl)oxy]ethyl}morpholine;
(2S)-2-[(2,6-difluorophenoxy)(2,3-dihydro-1-benzofuran-7-yl)methyl]morpholine;
(2S)-2-[(S)-(2-cyclopropyl-5-fluorophenoxy)(pyridin-2-yl)methyl]morpholine;
(2S)-2-[(S)-(2-fluoro-6-isopropoxyphenoxy)(phenyl)methyl]morpholine;
(2S)-2-[(S)-[(2-methoxypyridin-3-yl)oxy](phenyl)methyl]morpholine;
(2S)-2-[(5-fluoro-2-methoxyphenoxy)(phenyl)methyl]morpholine;
(2S)-2-[(3-fluoro-2-methoxyphenoxy)(phenyl)methyl]morpholine;
(2S)-2-[(2-ethoxy-5-fluorophenoxy)(phenyl)methyl]morpholine;
(2S)-2-[(2-ethoxy-3-fluorophenoxy)(phenyl)methyl]morpholine;
(2S)-2-[(S)-(2-fluoro-6-propoxyphenoxy)(phenyl)methyl]morpholine;
(2S)-2-[(2-ethoxyphenoxy)(4-methyl-1,3-oxazol-2-yl)methyl]morpholine;
(2S)-2-[(2,6-difluorophenoxy)(4-methyl-1,3-oxazol-2-yl)methyl]morpholine;
(2S)-2-{(4-methyl-1,3-oxazol-2-yl)[2-(trifluoromethoxy)phenoxy]methyl}morpholine;
(2S)-2-[(2,6-difluorophenoxy)(1,3-thiazol-2-yl)methyl]morpholine;
(2S)-2-{(1S)-1-[(2-ethoxypyridin-3-yl)oxy]pentyl}morpholine;
(2S)-2-[(2-bromophenoxy)(4-methyl-1,3-oxazol-2-yl)methyl]morpholine;
(2S)-2-[(S)-(2-fluoro-6-methylphenoxy)(phenyl)methyl]morpholine;
(2S)-2-[(S)-[(2-isopropylpyridin-3-yl)oxy](phenyl)methyl]morpholine;
(2S)-2-[(2-ethoxyphenoxy)(1,3-thiazol-2-yl)methyl]morpholine;
(2R)-2-[(R)-(2-ethoxyphenoxy)(pyridin-2-yl)methyl]morpholine;
(2S)-2-[(S)-[(2-isobutylpyridin-3-yl)oxy](phenyl)methyl]morpholine;
(2S)-2-[(S)-(2-fluoro-6-isopropylphenoxy)(phenyl)methyl]morpholine;
(2S)-2-[(S)-(2-cyclopropyl-6-fluorophenoxy)(phenyl)methyl]morpholine;
(2S)-2-[(S)-(2-bromo-6-fluorophenoxy)(6-methoxypyridin-2-yl)methyl]morpholine;
(2S)-2-[(S)-(2-bromo-6-fluorophenoxy)(pyridin-2-yl)methyl]morpholine;
(2S)-2-[(S)-(2-bromophenoxy)(6-methoxypyridin-2-yl)methyl]morpholine;
(2S)-2-[(S)-(2-fluoro-6-methoxyphenoxy)(6-methoxypyridin-2-yl)methyl]morpholine;
(2S)-2-{1-[(2-ethoxypyridin-3-yl)oxy]-2-methylpropyl}morpholine;
(2S)-2-[(2-cyclopropylphenoxy)(4-methyl-1,3-oxazol-2-yl)methyl]morpholine;
(2S)-2-{(1S)-1-[(2-ethoxypyridin-3-yl)oxy]butyl}morpholine;
(2S)-2-[(S)-{[2-(cyclopropylmethoxy)pyridin-3-yl]oxy}(phenyl)methyl]morpholine;
(2S)-2-[(S)-[2-fluoro-6-(trifluoromethyl)phenoxy](phenyl)methyl]morpholine;
(2S)-2-[(S)-[2-fluoro-6-(trifluoromethoxy)phenoxy](phenyl)methyl]morpholine;
(S)-2-[(2-ethoxyphenoxy)(1,3-oxazol-2-yl)methyl]morpholine;
(S)-2-[(2,6-difluorophenoxy)(1,3-oxazol-2-yl)methyl]morpholine;
(2S)-2-{(1S)-1-[(2-ethoxypyridin-3-yl)oxy]-2-phenylethyl}morpholine;
(2S)-2-[(S)-[4-fluoro-2-(methylthio)phenoxy](phenyl)methyl]morpholine;
(2S)-2-[(S)-(2,6-difluorophenoxy)(6-methoxypyridin-2-yl)methyl]morpholine;
(2R,2'R)-2,2'-[pyrazine-2,3-diylbis(oxymethylene)]dimorpholine;
(S)-2-[2-Ethoxy-pyridin-3-yloxymethyl]-morpholine; and
(2R)-2-[(2-fluoro-6-methoxyphenoxy)(pyridin-3-yl)methyl]morpholine.

The present invention further relates to a method of treatment of attention deficit hyperactivity disorder, urinary disorders, pain, anxiety, depression, premature ejaculation, or fibromyalgia, which comprises administering a therapeutically effective amount of a compound as defined in any of formulae I, II, and III.

Accordingly, one aspect of the present invention is directed to a method of selectively inhibiting reuptake of norepinephrine and the compounds used therefor, the method comprising the step of administering a therapeutically effective amount of a compound or composition to an individual, the compound or composition comprising a compound having a pharmacological selectivity of serotonin (Ki)/norepinephrine (Ki) of at least about 25, preferably at least about 50, and more preferably at least about 200.

Another aspect of the present invention is directed to a method of treating a human suffering from a condition, or preventing the condition, wherein inhibiting reuptake of norepinephrine provides a benefit, the method comprising the step of administering a therapeutically effective amount of a composition comprising a compound having a pharmacological selectivity of serotonin (Ki)/norepinephrine (Ki) of at least about 25, preferably at least about 50, and more preferably at least about 200.

This invention also relates to a method of treating a disorder or condition selected from the group consisting of norepinephrine dysfunction, single episodic or recurrent major depressive disorders, dysthymic disorders, depressive neurosis and neurotic depression, melancholic depression including anorexia, weight loss, insomnia, early morning waking or psychomotor retardation; atypical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior disorder; behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia (including social anxiety disorder), obsessive-compulsive disorder and related spectrum disorders, stress disorders including post-traumatic stress disorder, acute stress disorder and chronic stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, and other dementias, for example, due to HIV disease, head trauma, Parkinson's disease, Huntington's disease, Pick's disease, Creutzfeldt-Jakob disease, or due to multiple etiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; addictive disorders and withdrawal syndrome, chemical dependencies and addictions (e.g., dependencies on, or addictions to, alcohol, heroin, cocaine, benzodiazepines, psychoactive substances, nicotine, or phenobarbitol) and behavioral addictions such as an addiction to gambling; ocular disorders such as glaucoma and ischemic retinopathy addictive disorders (including those due to alcohol, nicotine, and other psychoactive substances) and withdrawal syndrome, adjustment disorders (including depressed mood, anxiety, mixed anxiety and depressed mood, disturbance of conduct, and mixed disturbance of conduct and mood); age-associated learning and mental disorders (including Alzheimer's disease); anorexia nervosa; apathy; attention-deficit (or other cognitive) disorders due to general medical conditions including attention-deficit disorder (ADD) and attention-deficit hyperactivity disorder (ADHD) and it's recognized sub-types; bulimia nervosa; chronic fatigue syndrome; pain; chronic pain; cyclothymic disorder; depression (including adolescent depression and minor depression); fibromyalgia and other somatoform disorders (including somatization disorder; conversion disorder; pain disorder; hypochondriasis; body dysmorphic disorder; undifferentiated somatoform disorder; and somatoform NOS); incontinence (i.e.; stress incontinence; genuine stress incontinence; and mixed incontinence); urinary disorders; premature ejaculation; inhalation disorders; intoxication disorders (alcohol addiction); mania; migraine headaches; obesity (i.e.; reducing the weight of obese or overweight patients); oppositional defiant disorder; peripheral neuropathy; diabetic neuropathy; post-herpetic neuralgic; premenstrual dysphoric disorder (i.e.; premenstrual syndrome and late luteal phase dysphoric disorder); sleep disorders (such as narcolepsy, insomnia and enuresis); specific developmental disorders; selective serotonin reuptake inhibition (SSRI) "poop out" syndrome (i.e.; wherein a patient who fails to maintain a satisfactory response to SSRI therapy after an initial period of satisfactory response); and TIC disorders (e.g.; Tourette's Disease) in a mammal in need thereof, including a human, comprising administering to a mammal in need of such treatment an amount of a compound of the formulae I, II, or III, or a pharmaceutically acceptable salt thereof, that is effective in treating such disorder or condition.

Another aspect of the present invention is directed to a preparation of a medicament from a composition comprising a compound having a pharmacological selectivity of serotonin (Ki)/norepinephrine (Ki) of at least about 25, preferably at least about 50, and more preferably at least about 200 to treat or prevent at least one of the aforementioned central nervous system disorders.

This invention also relates to a pharmaceutical composition comprising a therapeutically effective amount of a compound of the formulae I, II, or III, or a pharmaceutically acceptable salt thereof, and a pharmaceutically acceptable carrier.

This invention also relates to a pharmaceutical composition for treating a disorder or condition selected from norepinephrine dysfunction, single episodic or recurrent major depressive disorders, dysthymic disorders, depressive neurosis and neurotic depression, melancholic depression including anorexia, weight loss, insomnia, early morning waking or psychomotor retardation; atypical depression (or reactive depression) including increased appetite, hypersomnia, psychomotor agitation or irritability, seasonal affective disorder and pediatric depression; bipolar disorders or manic depression, for example, bipolar I disorder, bipolar II disorder and cyclothymic disorder; conduct disorder; disruptive behavior disorder; behavioral disturbances associated with mental retardation, autistic disorder, and conduct disorder; anxiety disorders such as panic disorder with or without agoraphobia, agoraphobia without history of panic disorder, specific phobias, for example, specific animal phobias, social anxiety, social phobia (including social anxiety disorder), obsessive-compulsive disorder and related spectrum disorders, stress disorders including post-traumatic stress disorder, acute stress disorder and chronic stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder; mood disorders associated with schizophrenia; delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, and other dementias, for example, due to HIV disease, head trauma, Parkinson's disease, Huntington's disease, Pick's disease, Creutzfeldt-Jakob disease, or due to multiple etiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; addictive disorders and withdrawal syndrome, chemical dependencies and addictions (e.g., dependencies on, or addictions to, alcohol, heroin, cocaine, benzodiazepines, psychoactive substances, nicotine, or phenobarbitol) and behavioral addictions such as an addiction to gambling; ocular disorders such as glaucoma and ischemic retinopathy addictive disorders (including those due to alcohol, nicotine, and other psychoactive substances) and withdrawal syndrome, adjustment disorders (including depressed mood, anxiety, mixed anxiety and depressed mood, disturbance of conduct, and mixed disturbance of conduct and mood); age-associated learning and mental disorders (including Alzheimer's disease); anorexia nervosa; apathy; attention-deficit (or other cognitive) disorders due to general medical conditions including attention-deficit disorder (ADD) and attention-deficit hyperactivity disorder (ADHD) and it's recognized sub-types; bulimia nervosa; chronic fatigue syndrome; pain; chronic pain; cyclothymic disorder; depression (including adolescent depression and minor depression); fibromyalgia and other somatoform disorders (including somatization disorder; conversion disorder; pain disorder; hypochondriasis; body dysmorphic disorder; undifferentiated somatoform disorder; and somatoform NOS); incontinence (i.e.; stress incontinence; genuine stress incontinence; and mixed incontinence); urinary disorders; premature ejaculation; inhalation disorders; intoxication disorders (alcohol addiction); mania; migraine headaches; obesity (i.e.; reducing the weight of obese or overweight patients); oppositional defiant disorder; peripheral neuropathy; diabetic neuropathy; post-herpetic neuralgic; premenstrual dysphoric disorder (i.e.; premenstrual syndrome and late luteal phase dysphoric disorder); sleep disorders (such as narcolepsy, insomnia and enuresis); specific developmental disorders; selective serotonin reuptake inhibition (SSRI) "poop out" syndrome (i.e.; wherein a patient who fails to maintain a satisfactory response to SSRI therapy after an initial period of satisfactory response); and TIC disorders (e.g.; Tourette's Disease) in a mammal in need of such treatment, including a human, comprising an amount of a compound of the formulae I, II, or III or a pharmaceutically acceptable salt thereof, that is effective in treating such disorder or condition, and a pharmaceutically acceptable carrier.

Another specific aspect of this invention relates to the above method wherein the compound of formulae I, II, or III is administered to a human for the treatment of any two or more comorbid disorders or conditions selected from those disorders and conditions referred to in any of the above methods.

For the treatment of ADHD, depression, anxiety, schizophrenia or any of the other disorders and conditions referred to above in the descriptions of the methods and pharmaceutical compositions of this invention, the novel compounds of this invention can be used in conjunction with one or more additional active agents including antidepressants, anti-psychotics or anti-anxiety agents. Examples of classes of antidepressants that can be used in combination with the active compounds of this invention include norepinephrine reuptake inhibitors (NRIs), selective serotonin reuptake inhibitors (SRIs), NK-1 receptor antagonists, monoamine oxidase inhibitors (MAOs), reversible inhibitors of monoamine oxidase (RIMAs), dual serotonin and norepinephrine reuptake inhibitors, corticotropin releasing factor (CRF) antagonists, α-adrenoreceptor antagonists, alpha-2-delta ligands (A2D), and atypical antidepressants.

Another type of agent that can be used in combination with the novel compounds of this invention are nicotinic receptor agonists or antagonists.

SRIs useful for the methods and pharmaceutical compositions of the present invention include, but are not limited to sertraline (Zoloft®), sertraline metabolite demethylsertraline, fluoxetine (Prozac®), norfluoxetine (fluoxetine desmethyl metabolite), fluvoxamine (Luvox®), paroxetine (Seroxat®, Paxil®) and its alternative formulation, Paxil-CR®, citalopram (Celexa®), citalopram metabolite desmethylcitalopram, escitalopram (Lexapro®), d,l-fenfluramine (Pondimin®), femoxetine, ifoxetine, cyanodothiepin, litoxetine, cericlamine, dapoxetine, nefazaodone (Serxone®)), and trazodone (Desyrel®), or any prodrug thereof or any pharmaceutically acceptable salt of the SRI or the prodrug thereof.

NRIs useful for the methods and pharmaceutical compositions of the present invention include, but are not limited to, reboxetine (Edronax®) and all isomers of reboxetine, ie., (R/R,S/S,R/S,S/R), desipramine (Norpramin®), maprotiline (Ludiomil®), lofepramine (Gamanil®), mirtazepine (Remeron®), oxaprotiline, fezolamine, atomoxetine (Strattera®) and buproprion (Wellbutrin®), buproprion metabolite hydroxybuproprion, nomifensine (Merital®), viloxazine (Vivalan®), or mianserin (Bolvidon®) or any prodrug thereof or any pharmaceutically acceptable salt of the $NR^1$ or the prodrug thereof.

Pharmaceutical agents which inhibit the reuptake of both serotonin and norepinephrine include venlafaxine (Effexor®), venlafaxine metabolite O-desmethylvenlafaxine, clomipramine (Anafranil®), clomipramine metabolite desmethylclomipramine, duloxetine (Cymbalta®), milnacipran, and imipramine (Tofranil® or Janimine®).

Examples of preferred A2D ligands for use with the present invention are those compounds generally or specifically disclosed in U.S. Pat. No. 4,024,175, particularly gabapentin, EP641330, particularly pregabalin, U.S. Pat. No. 5,563,175, WO9733858, WO9733859, WO9931057, WO9931074, WO9729101, WO02085839, particularly [(1R,5R,6S)-6-(Aminomethyl)bicyclo[3.2.0]hept-6-yl]acetic acid, WO9931075, particularly 3-(1-Aminomethyl-cyclohexylmethyl)-4H-[1,2,4]oxadiazol-5-one and C-[1-(1H-Tetrazol-5-ylmethyl)-cycloheptyl]-methylamine, WO9921824, particularly (3S,4S)-(1-Aminomethyl-3,4-dimethyl-cyclopentyl)-acetic acid, WO0190052, WO0128978, particularly (1α,3α, 5α)(3-amino-methyl-bicyclo[3.2.0]hept-3-yl)-acetic acid, EP0641330, WO9817627, WO0076958, particularly (3S, 5R)-3-aminomethyl-5-methyl-octanoic acid, U.S. Ser. No. 10/401,060, particularly (3S,5R)-3-amino-5-methyl-heptanoic acid, U.S. Ser. No. 10/401,060, (3S,5R)-3-amino-5-methyl-nonanoic acid, and (3S,5R)-3-Amino-5-methyl-octanoic acid, EP1178034, EP1201240, WO9931074, WO03000642, WO0222568, WO0230871, WO0230881 WO02100392, WO02100347, WO0242414, WO0232736 and WO0228881, and pharmaceutically acceptable salts and solvates thereof.

Suitable CRF antagonists include those compounds described in International Patent Application Nos. WO 94/13643, WO 94/13644, WO 94/13661, WO 94/13676 and WO 94/13677. Suitable atypical anti-depressants include bupropion, lithium, nefazodone, trazodone and viloxazine.

Suitable NK-1 receptor antagonists include those referred to in World Patent Publication WO 01/77100.

Suitable classes of anti-anxiety agents that can be used in combination with the active compounds of this invention include benzodiazepines and serotonin IA ($5\text{-HT}_{IA}$) agonists or antagonists, especially $5\text{-HT}_{IA}$ partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable $5\text{-HT}_{IA}$ receptor agonists or antagonists include buspirone, flesinoxan, gepirone and ipsapirone.

Suitable antipsychotic agents include both conventional and atypical antipsychotics.

Conventional antipsychotics are antagonists of dopamine ($D_2$) receptors. The atypical antipsychotics also have $D_2$ antagonistic properties but possess different binding kinetics to these receptors and activity at other receptors, particularly $5\text{-HT}_{2A}$, $5\text{-HT}_{2C}$ and $5\text{-HT}_{2D}$ (Schmidt B et al, Soc. Neurosci. Abstr. 24:2177, 1998).

Examples of dopamine (D4) receptor ligands are described in U.S. Pat. Nos. 6,548,502, 5,852,031, 5,883,094, 5,889,010 and WO 98/08835.

Examples of nicotinic receptor agonists or antagonists include: varenicline, azaindole-ethylamine derivatives as described in U.S. Pat. No. 5,977,131, and analogs, derivatives, prodrugs, and pharmaceutically acceptable salts of the nicotinic receptor agonists or antagonists and the prodrugs.

A particularly preferred nicotinic receptor agonist is varenicline, 7,8,9,10-tetrahydro-6,10-methano-6H-pyrazino[2,3-h][3]benzapine (2R,3R)-2,3-dihydroxybutanedioate, or any pharmaceutical acceptable salt thereof, including any polymorph or any prodrug thereof, or any pharmaceutically acceptable salt of such prodrug. A preferred salt of varenicline is varenicline tartrate. Varenicline is a partial nicotine agonist with affinity for some nicotine receptor subtypes but not others. Synthesis of varenicline tartrate is disclosed in WO 99/35131, U.S. Pat. No. 6,410,550, Patent Application Nos. 1997070245, 2002072524, 2002072525, 2002111350, and 2002132824.

The class of atypical antipsychotics includes clozapine (Clozaril®), 8-chloro-11-(4-methyl-1-piperazinyl)-5H-dibenzo[b,e][1,4]diazepine (U.S. Pat. No. 3,539,573); risperidone (Risperdal®), 3-[2-[4-(6-fluoro-1,2-benzisoxazol-3-yl)piperidino]ethyl]-2-methyl-6,7,8,9-tetrahydro-4H-pyrido-[1,2-a]pyrimidin-4-one (U.S. Pat. No. 4,804,663); olanzapine (Zyprexa®), 2-methyl-4-(4-methyl-1-piperazinyl)-10H-thieno[2,3-b][1,5]benzodiazepine (U.S. Pat. No. 5,229,382); quetiapine (Seroquel®), 5-[2-(4-dibenzo[b,f][1,4]thiazepin-11-yl-1-piperazinyl)ethoxy]ethanol (U.S. Pat. No. 4,879,288); aripiprazole (Abilify®), 7-{4-[4-(2,3-dichlorophenyl)-1-piperazinyl]-butoxy}-3,4-dihydro carbostyril and 7-{4-[4-(2,3-dichlorophenyl)-1-piperazinyl]-butoxy}-3,4-dihydro-2 (1H)-quinolinone (U.S. Pat. Nos. 4,734,416 and 5,006,528); sertindole, 1-[2-[4-[5-chloro-1-(4-fluorophenyl)-1H-indol-3-yl]-1-piperidinyl]ethyl]imidazolidin-2-one (U.S. Pat. No. 4,710,500); amisulpride (U.S. Pat. No. 4,410,822); ziprasidone (Geodon®) 5-[2-[4-(1,2-benzisothiazol-3-yl)piperazin-3-yl]ethyl]-6-chloroindolin-2-one hydrochloride hydrate (U.S. Pat. No. 4,831,031); and asenapine trans-5-chloro-2-methyl-2,3,3a,12b-tetrahydro-1H-dibenz[2,3:6,7]oxepino[4,5-c]pyrrole (U.S. Pat. Nos. 4,145,434 and 5,763,476).

This invention also relates to a method of treating a disorder or condition selected from addictive disorders (including those due to alcohol, nicotine, and other psychoactive substances) and withdrawal syndrome, adjustment disorders (including depressed mood, anxiety, mixed anxiety and depressed mood, disturbance of conduct, and mixed disturbance of conduct and mood); age-associated learning and mental disorders (including Alzheimer's disease); anorexia nervosa; apathy; attention-deficit (or other cognitive) disorders due to general medical conditions including attention-deficit disorder (ADD) and attention-deficit hyperactivity disorder (ADHD) and it's recognized sub-types; bulimia nervosa; chronic fatigue syndrome; pain; chronic pain; cyclothymic disorder; depression (including adolescent depression and minor depression); fibromyalgia and other somatoform disorders (including somatization disorder; conversion disorder; pain disorder; hypochondriasis; body dysmorphic disorder; undifferentiated somatoform disorder; and somatoform NOS); incontinence (i.e.; stress incontinence; genuine stress incontinence; and mixed incontinence); urinary disorders; premature ejaculation; inhalation disorders; intoxication disorders (alcohol addiction); mania; migraine headaches; obesity (i.e.; reducing the weight of obese or overweight patients); oppositional defiant disorder; peripheral neuropathy; diabetic neuropathy; post-herpetic neuralgic; premenstrual dysphoric disorder (i.e.; premenstrual syndrome and late luteal phase dysphoric disorder); sleep disorders (such as narcolepsy, insomnia and enuresis); specific developmental disorders; selective serotonin reuptake inhibition (SSRI) "poop out" syndrome (i.e.; wherein a patient who fails to maintain a satisfactory response to SSRI therapy after an initial period of satisfactory response); and TIC disorders (e.g.; Tourette's Disease) in a mammal in need of such treatment, including a human, comprising administering to said mammal:

(a) a compound of the formulae I, II, or III or a pharmaceutically acceptable salt thereof; and (b) another pharmaceutically active compound that is an anti-depressant, anti-psychotic or anti-anxiety agent, or a pharmaceutically acceptable salt thereof;

wherein the active compounds "a" and "b" are present in amounts that render the combination effective in treating such disorder or condition.

Another more specific aspect of this invention relates to the above method wherein the compounds of formulae I, II, or III and the additional pharmaceutical agent includes an antidepressant, anti-anxiety agent, or anti- psychotic are administered to a human for the treatment of any two or more comorbid disorders or conditions selected from those disorders and conditions referred to in any of the above methods.

This invention also relates to a pharmaceutical composition for treating a disorder or condition selected from addictive disorders (including those due to alcohol, nicotine, and other psychoactive substances) and withdrawal syndrome, adjustment disorders (including depressed mood, anxiety, mixed anxiety and depressed mood, disturbance of conduct, and mixed disturbance of conduct and mood); age-associated learning and mental disorders (including Alzheimer's disease); anorexia nervosa; apathy; attention-deficit (or other cognitive) disorders due to general medical conditions including attention-deficit disorder (ADD) and attention-deficit hyperactivity disorder (ADHD) and it's recognized sub-types; bulimia nervosa; chronic fatigue syndrome; pain; chronic pain; cyclothymic disorder; depression (including adolescent depression and minor depression); fibromyalgia and other somatoform disorders (including somatization disorder; conversion disorder; pain disorder; hypochondriasis; body dysmorphic disorder; undifferentiated somatoform disorder; and somatoform NOS); incontinence (i.e.; stress incontinence; genuine stress incontinence; and mixed incontinence); urinary disorders; premature ejaculation; inhalation disorders; intoxication disorders (alcohol addiction); mania; migraine headaches; obesity (i.e.; reducing the weight of obese or overweight patients); oppositional defiant disorder; peripheral neuropathy; diabetic neuropathy; post-herpetic neuralgic; premenstrual dysphoric disorder (i.e.; premenstrual syndrome and late luteal phase dysphoric disorder); sleep disorders (such as narcolepsy, insomnia and enuresis); specific developmental disorders; selective serotonin reuptake inhibition (SSRI) "poop out" syndrome (i.e.; wherein a patient who fails to maintain a satisfactory response to SSRI therapy after an initial period of satisfactory response); and TIC disorders (e.g.; Tourette's Disease) in a mammal in need of such treatment, including a human, comprising:

(a) a compound of the formulae I, II, or III or a pharmaceutically acceptable salt thereof;

(b) another pharmaceutically active compound including an antidepressant or anti-anxiety agent, or a pharmaceutically acceptable salt thereof; and (c) a pharmaceutically acceptable carrier;

wherein the active compounds "a" and "b" are present in amounts that render the composition effective in treating such disorder or condition.

Another aspect of the present invention is directed to use of a composition comprising a compound of formula I, II, or III having a pharmacological selectivity of serotonin (Ki)/norepinephrine (Ki) of at least about 25, preferably at least about 50, and more preferably at least about 200, in a manufacture of a medicament to treat or prevent at least one of the aforementioned central nervous system disorders.

This invention also relates to a pharmaceutical composition comprising a therapeutically effective amount of a compound of the formulae I, II, or III or a pharmaceutically acceptable salt thereof, and a pharmaceutically acceptable carrier.

Compounds of formulae I, II, or III may contain chiral centers and therefore may exist in different enantiomeric and diastereomeric forms. This invention relates to all optical isomers and all stereoisomers of compounds of the formulae I, II, or III, both as racemic mixtures and as individual enantiomers and diastereoisomers of such compounds, and mixtures thereof, and to all pharmaceutical compositions and methods of treatment defined above that contain or employ them, respectively. Individual isomers can be obtained by known methods, such as classical resolution, stereo-selective reaction, or chromatographic separation in the preparation of the final product or its intermediate. Individual enantiomers of the compounds of formulae I, II, or III may have advantages, as compared with the racemic mixtures of these compounds, in the treatment of various disorders or conditions.

When two chiral centers exist in one molecule, there are four possible stereoisomers: (R,R), (S,S), (R,S), and (S,R). Of these, (R,R) and (S,S) are an example of a pair of enantiomers (mirror images of each other), which typically share chemical properties and melting points just like any other enantiomeric pair. The mirror images of (R,R) and (S,S) are not, however, superimposable on (R,S) and (S,R). This relationship is called diastereoisomeric, and the (S,S) molecule is a diastereoisomer of the (R,S) molecule, whereas the (R,R) molecule is a diastereoisomer of the (S,R) molecule.

In so far as the compounds of formulae I, II, or III of this invention are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)) salts.

The present invention also includes isotopically labelled compounds, which are identical to those recited in formulae I, II, or III, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^{3}H$, $^{18}F$, $^{11}C$ and $^{14}C$ are incorporated, are useful in drug and/or substrate tissue distribution assays and others such as $^{11}C$ and $^{18}F$ are useful for imaging studies i.e., PET, MRI, etc. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formulae I, II, or III of this invention and prodrugs thereof can generally be prepared by carrying out the procedures disclosed in the Schemes and/or in the Examples below, by substituting a readily available isotopically labelled reagent for a non-isotopically labelled reagent.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "aryl" includes substituted or unsubstituted groups, including 5- and 6-membered single-ring aromatic groups that may include from zero to four heteroatoms, for example, benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Aryl groups may be substituted with, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfmoyl, sulfonamide, nitro, trifluoromethyl, cyano, azido, heterocyclyl, alkylaryl, or an aromatic or heteroaromatic moiety.

Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkyl, alkoxy, alkylcarbonyloxy, arylcarbonyloxy, alkoxycarbonyloxy, aryloxycarbonyloxy, carboxylate, alkylcarbonyl, alkylaminocarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin). In an aspect, the heteroaromatic group is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, or 2-, 3-, 4-, 5, 6, or 7-indolyl.

The term "phenyl" includes aromatic rings of six carbons. Phenyl may be unsubstituted (or substituted with hydrogen) or substituted at one or more positions with a substituent such as, but not limited to, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. The term "aryl" is intended to include both substituted and unsubstituted phenyl groups.

The term "aryloxy" or "—O-aryl" includes substituted and unsubstituted aryl groups covalently linked to an oxygen atom. Examples of aryloxy groups include phenoxy and benzoxy.

The term "alkoxy" includes substituted and unsubstituted alkyl, alkenyl, and alkynyl groups covalently linked to an oxygen atom. Examples of alkoxy groups include methoxy, ethoxy, isopropoxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc The term "heteroaryl" as used herein, unless otherwise indicated, includes monocyclic aromatic heterocycles containing five to seven ring members, of which from 1 to 4 can be heteroatoms selected, independently, from N, S and O, and bicyclic aromatic heterocycles containing from six to 10 ring members, of which from 1 to 4 can be heteroatoms selected, independently, from N, S and O.

The term "heterocycle", as used herein, unless otherwise indicated, includes substituted or unsubstituted 4, 5 or 6 membered ring containing at least one N, O, or S heteroatom which includes both aromatic and non-aromatic ring systems and includes fusion to a 5 or 6 membered aromatic, heteroaromatic, non-aromatic carbocycle, or non-aromatic heterocycle. Examples of heterocycles include, but are not limited to furan, tetrahydrofuran, thiophene, pyrrole, pyrrolidine, oxazole, thiazole, imidazole, pyrazole, isoxazole, isothiazole, triazole, tetrazole, pyran, pyridine, piperidine, morpholine, pyridazaine, pyrimidine, pyrazine, piperazine, and the fused bicyclic heterocycles: indolizine, indole, isoindole, indoline, benzofuran, benzothiophene, indazole, benzimidazole, benzthiazole, quinoline, isoquinoline, quinazoline, azetidine, oxetane, and ethylenedioxy benzene.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups, which include oxygen, nitrogen, sulfur or phosphorous atoms replacing one or more carbons of the hydrocarbon backbone. In certain aspects, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including; alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfmoyl, sulfonamide, nitro, trifluoromethyl, cyano, azido, heterocyclyl, alkylaryl, or an aromatic or heteroaromatic moiety.

The term "one or more substituents", as used herein, refers to a number of substituents that equals from one to the maximum number of substituents possible based on the number of available bonding sites.

The terms "halo" and "halogen", as used herein, unless otherwise indicated, include, fluoro, chloro, bromo and iodo.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The term "treating", as used herein, refers to reversing, alleviating, inhibiting the progress of, or preventing the disorder or condition to which such term applies, or preventing one or more symptoms of such condition or disorder.

The term "treatment", as used herein, refers to the act of treating, as "treating" is defined immediately above. The term "treatment" also includes the diminishment or alleviation of at least one symptom associated or-caused by the disorder being treated. For example, treatment can be diminishment of several symptoms of a disorder or complete eradication of a disorder.

The compounds of formulae I, II, or III and their pharmaceutically acceptable salts are also referred to herein, collectively, as the "novel compounds of this invention" and the "active compounds of this invention".

Additional benefits and features of the present invention will become apparent to those skilled in the art from a review of the following detailed description, taken in conjunction with the example and the appended claims. It should be noted, however, that while the invention is susceptible of aspects in various forms, described hereafter are specific preferred aspects of the invention with the understanding that the present disclosure is intended as illustrative, and is not intended to limit the invention to the specific aspects described herein.

DETAILED DESCRIPTION OF THE INVENTION

The compounds of formulae I, II, or III of the present invention may be prepared as described in the following reaction schemes. Unless otherwise indicated, $R^1$-$R^8$ in the reaction schemes and discussion that follow, are as defined above.

Unless otherwise provided herein:
TMS=Chlorotrimethylsilane;
Red-Al=sodium bis(2-methoxy) aluminum;
IBX=1,2-Benziodoxol-3(1H)-one, 1-hydroxy, 1-oxide;
DIAD=Diisopropyl azodicarboxylate;
BOC=butyloxy carbonyl;
TFA=trifluoroacetic acid; and
DPPP=1,3-bis-diphenylphosphino propane.

Scheme A:

General procedure for the synthesis of morpholine derivatives starting from benzyl glycidol (General Procedure A).

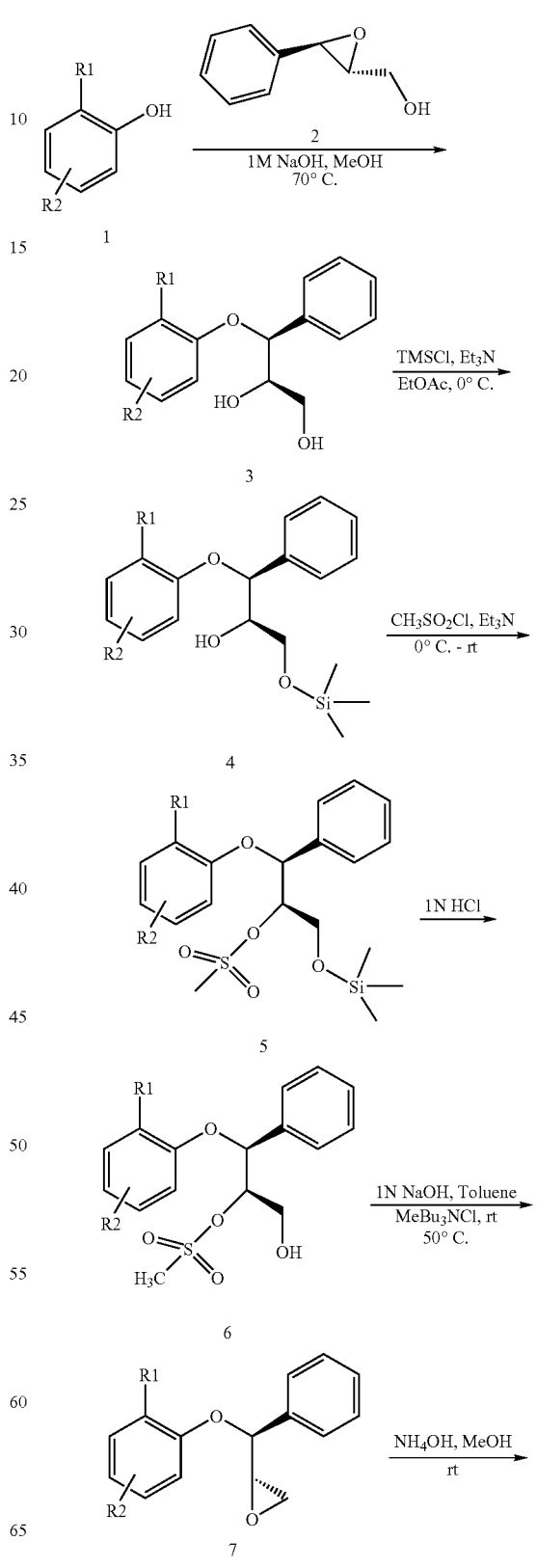

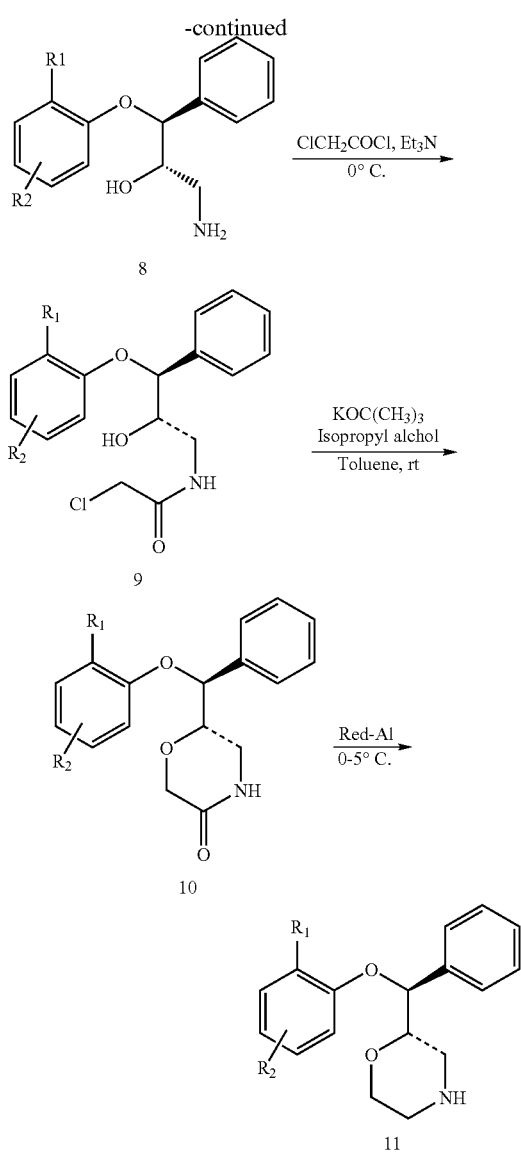

General procedure for the preparation of morpholine derivatives (Scheme A)

Preparation of Diol 3

To a 1 M sodium hydroxide solution, the appropriate phenol (1.05 equiv) was added and stirred at room temperature for 30 min. Then (2R,3R)-3-phenylglycidol 2 (1.0 equiv) was added in one portion and the reaction mixture was heated at 70° C. for 2 h. The reaction mixture was cooled to room temperature and the product was extracted with ether. The combined organic extract was washed with 1 M sodium hydroxide solution, brine and dried over anhydrous sodium sulfate. The solvent was removed under reduced pressure and the product was purified on a column of silica gel to afford the pure diol.

Preparation of Mesylate 6

To a solution of diol 3 in ethyl acetate, triethylamine (excess) was added. The mixture was cooled to 0° C., then chlorotrimethylsilane (1.0 equiv) in ethyl acetate was added dropwise over 30 min. After 1 h, if TLC analysis indicated that a small amount of starting diol was left, an additional amount of chlorotrimethylsilane (0.26 mL, 1.83 mmol) was added and the reaction mixture was stirred at 0° C. for 45 min. When TLC analysis indicated diol 3 had converted to TMS derivative 4, triethylamine (1.0 equiv) was added to the reaction mixture followed by methanesulfonyl chloride (1.1 equiv which was added dropwise). The reaction mixture was allowed to attain room temperature and stirred for 12 h. When TLC analysis indicated TMS derivative 4 was converted to 5, 1 M hydrochloric acid solution was added and the reaction mixture was stirred at room temperature for 1 h. The reaction mixture was diluted with water and the organic layer was separated and the aqueous layer was extracted with ethyl acetate. The combined organic extract was washed with aqueous sodium bicarbonate solution, brine and dried over anhydrous sodium sulfate. The solvent was removed under reduced pressure to give the mesylate 6 as a colorless liquid Preparation of Epoxide 7

To a solution of mesylate 6 in toluene, 1 M sodium hydroxide solution (3 equiv of base) and methyltributylammonium chloride (75 wt % in water) were added. The reaction mixture was stirred at room temperature for 48 h and at 50° C. for 18 h. The layers were separated and the aqueous layer was extracted with toluene. The combined organic extract was washed with brine and dried over anhydrous sodium sulfate. The solvent was removed under reduced pressure and the product was purified on a column of silica gel to give the epoxide 7.

Preparation of Aminoalcohol 8

To a concentrated ammonium hydroxide solution, an equal volume of methanol was added. A solution of epoxide 7 in methanol was added drop-wise over 3 h. The reaction mixture was stirred at room temperature for 18 h. The product was extracted with dichloromethane. The combined organic extract was washed with brine, dried over anhydrous sodium sulfate. The solvent was removed under reduced pressure. Purification on a silica gel column gave compound 8.

Preparation of Chloroacetamide 9

To a mixture of aminoalcohol 8 and triethylamine (1.5 equiv) in THF, a solution of chloroacetyl chloride (1 equiv) in THF was added dropwise. After stirring for 1.5 h, the solvent and volatiles were removed under reduced pressure, the residue was dissolved in ethyl acetate, washed with water, brine and dried over anhydrous sodium sulfate. The solvent was removed under reduced pressure to give chloroacetamide 9.

Preparation of Morpholinone 10

Chloroacetamide 9 was dissolved in a mixture of isopropyl alcohol and toluene. A solution of potassium tert-butoxide (4 equiv) in isopropyl alcohol was added dropwise under nitrogen atmosphere. The reaction mixture was stirred at room temperature for 4 h. The pH of the mixture was adjusted to 6.5 by adding 2 M HCl solution and volatiles were removed under reduced pressure. The residue was partitioned between toluene and water. The aqueous layer was extracted with toluene. The combined organic extract was washed with sodium bicarbonate solution, brine and dried over anhydrous sodium sulfate. The solvent was removed under reduced pressure and the product was triturated with a mixture of ethyl acetate and hexane to give morpholinone 10 typically as a white solid.

Preparation of 11

To a solution of morpholinone 10 in toluene, Red-Al (75% solution in toluene) was added dropwise at 0° C. The reaction mixture was stirred at ice temperature for 3 h. Excess Red-Al was destroyed by drop-wise addition of 2 M NaOH solution. The layers were separated and the aqueous layer was diluted with water and extracted with toluene. The combined organic extract was washed with brine and dried over anhydrous $Na_2SO_4$. The solvent was removed under reduced pressure and the product was purified on a column of silica gel (ethyl acetate: methanol) to give morpholine compound 11 typically as a colorless liquid.

Scheme B

Palladium coupling of Bromo derivative (General Procedure B).

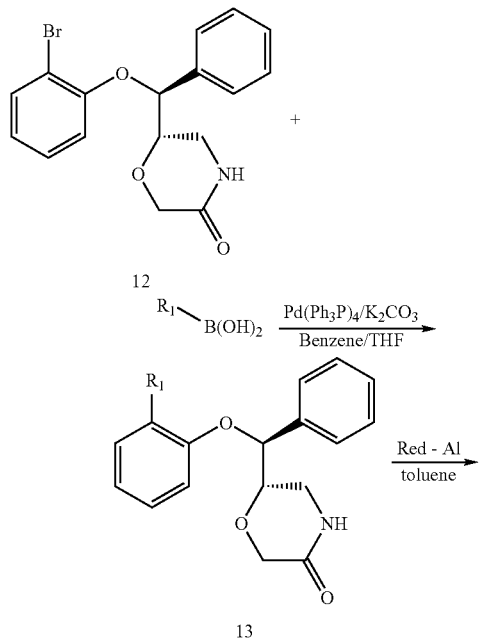

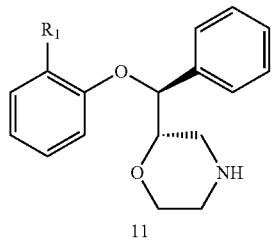

Preparation of Morpholinone 13:

To a solution of arylbromide 12 in benzene was added tetrakis(triphenylphosphine) palladium (0) and potassium carbonate. Then a solution of the appropriate boronic acid in THF was added. The reaction mixture was heated to reflux (80° C.) for 18 h and then cooled to room temperature, diluted with toluene and washed with water and brine. The organic phase was dried over anhydrous sodium sulfate. The solvent was removed under reduced pressure and the residue was purified on a column of silica gel (EtOAc/ Hexane) to give morpholinone compound 13.

Preparation of Morpholine Compound 11

The reduction of the morpholinone to the morpholine was carried out as described in General Procedure A.

Scheme C: General procedure for the preparation of morpholine compound 7 starting from morpholine alcohols 1 or 2 (General Procedure C).

Synthesis of "S" morpholine compounds (Formula I, II).

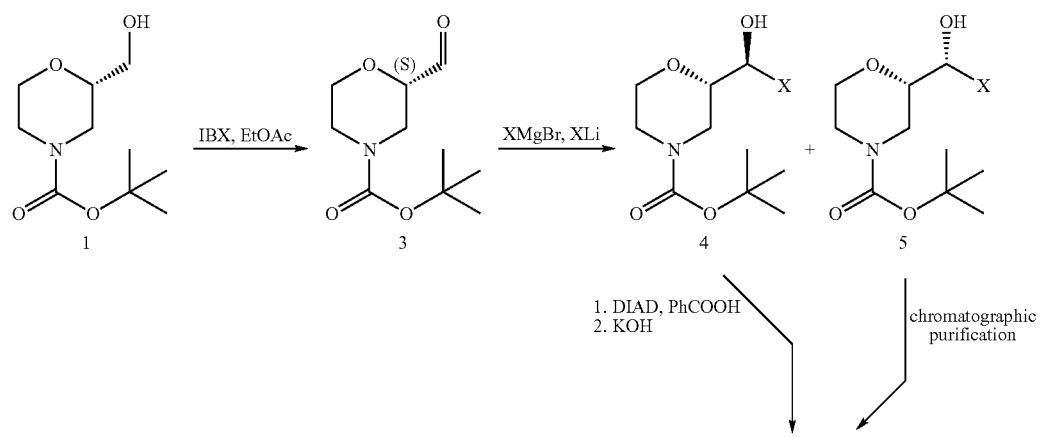

-continued
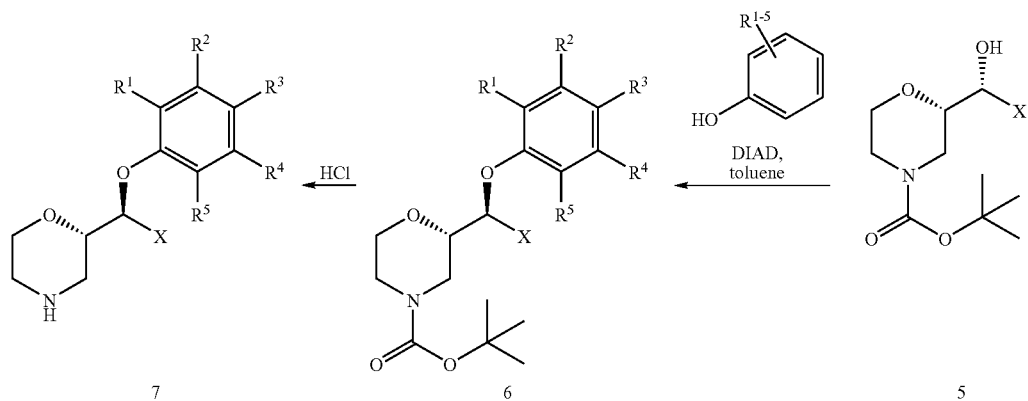
Synthesis of "R" morpholine compounds (Formula I, II).
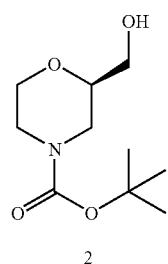
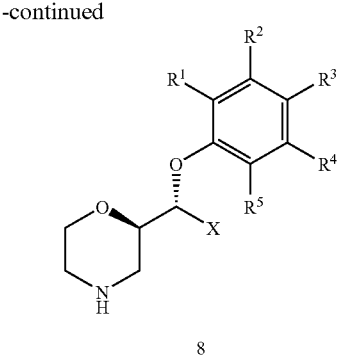
Alternative general route for the preparation of morpholine compounds (Formula I, II, III).
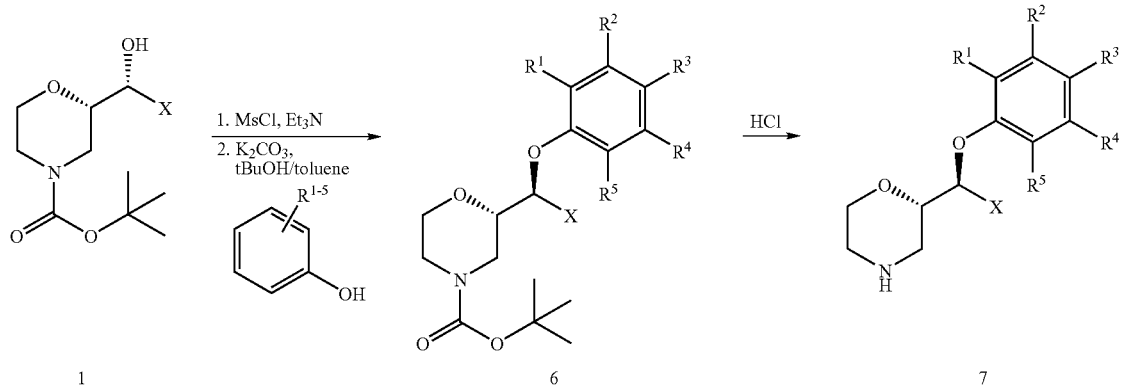

-continued

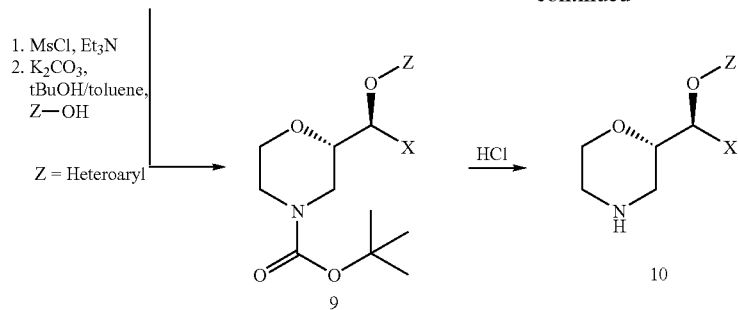

Scheme C, continued
Synthesis of "2-S,3-R" morpholine compounds (Formula I, II).

Synthesis of "2-R,3-S" morpholine compounds (Formula I, II)

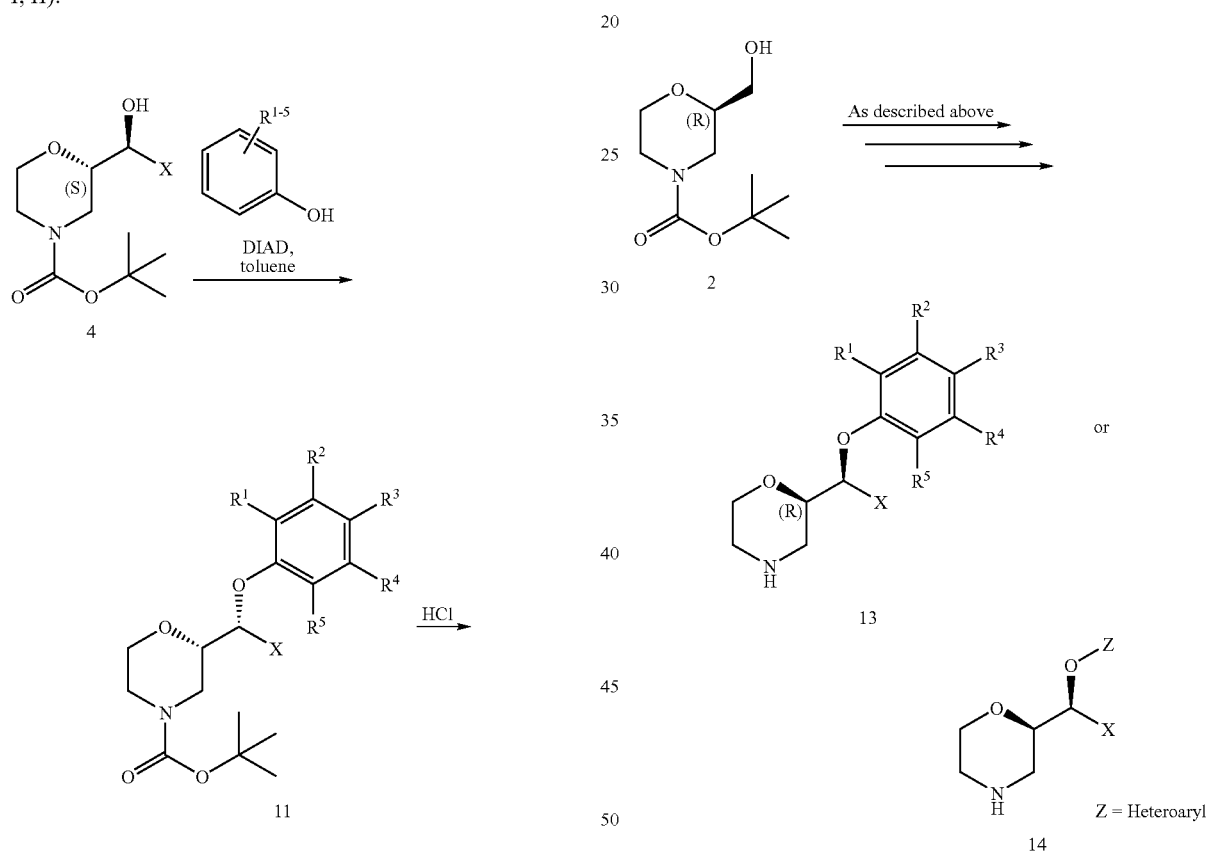

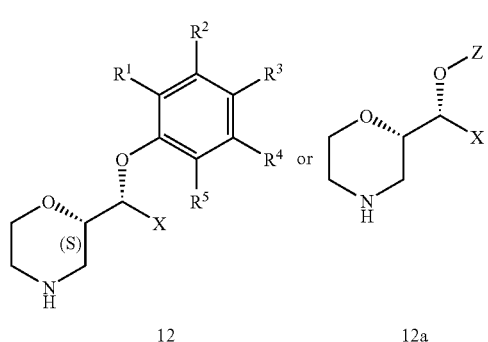

General procedure for the synthesis of (2-S,3-S)-, (2-R,3-R)-morpholine compounds (Formula I, II, or III) and (2-S,3-R)-, (2-R,3-S)-morpholine compounds (Formula I, II, or III).

Oxidation of N—BOC-morpholine Alcohol

The appropriate S or R chiral morpholine alcohol (1, or 2) was dissolved in a suitable amount of EtOAc (0.2M) in a round-bottom flask fitted with a reflux condenser and a magnetic stirbar, and this solution was gently refluxed with IBX (2.0 equiv) for 3 hours with stirring. The reaction mixture was cooled to room temperature, diluted with hexanes (40% by volume) and filtered through a medium porosity frit filter. The collected solid was washed twice with a 1:1 mixture of EtOAc and hexanes and the combined filtrates were concentrated to afford a colorless oil which was used in the next reaction without further purification. See Org Lett, 2002, 3002. The crude NMR shows CHO peak and a trace (<3%) of iodobenzoic acid. The aldehyde thus obtained gives a good result in the subsequent alkylation reaction. The aldehyde product 3 is somewhat unstable and should be used shortly after its preparation.

Alkylation of the N—BOC-morpholine Aldehyde

The crude aldehyde (3) from the previous step was dissolved in anhydrous THF (0.6M) in a dry flask under an inert atmosphere and the resulting solution was cooled to –40 C. A solution of the appropriate alkyllithium or Grignard reagent (1.5-3.0 equiv.) in THF or diethylether was added dropwise over 15 minutes via syringe while vigorously stirring the reaction mixture. When the addition was complete, the cooling was removed, and the reaction was allowed to come to ambient temperature. After stirring for 4 hours at this temperature, the reaction was judged complete (by TLC analysis, EtOAC in hexanes as the eluent) and was poured into a beaker containing sat. aq. NH4Cl and ice. The resulting mixture was extracted with EtOAc and the combined organic extracts were washed with sat. aq. NaCl and concentrated to dryness. The resulting crude oil was adorbed onto silica gel and purified by column chromatography (silica, Biotage prepack, EtOAc in hexanes) to afford the products 4 and 5 as a colorless oil (60-75% overall yield for two steps from the starting N—BOC-morpholine alcohol 1 or 2). HNMR and MS analysis were consistent with product.

Inversion of the Secondary Alcohol:

This procedure was applied to invert the stereochemistry of an undesired alcohol (e.g. 4) to the desired alcohol (e.g. 5) during the synthesis of (2-S,3-S)- and (2-R,3-R)-morpholine derivatives such as 7, 8, or 10. This procedure was also applied to convert the undesired (e.g. 5) to the desired alcohol (e.g. 4) during the synthesis of (2-S,3-R)- and (2-R,3-S)-morpholine derivatives such as 12, 12a, 13, or 14. Hence, alcohols 4 and 5 could be interconverted, thus making the synthetic route applicable to any of the four possible stereoisomers Benzoate Formation The starting alcohol (5), triphenylphosphine (3.0 equiv.), and the starting phenol (5.0 equiv.) were dissolved in toluene (0.4 M) in a round-bottom flask fitted with a magnetic stirbar and septa, and the mixture was cooled to 0 C and stirred for 10 minutes at this temperature. DIAD (2.9 equiv) was added dropwise over 10 minutes at 0 C. The reaction mixture was warmed to ambient temperature and stirred for 24-48 hours. Reaction progress was monitored by TLC (40% EtOAc in hexanes as an eluent) and MS. Upon completion of the reaction, the solvent was removed in vacuo, affording an oil which was dissolved in dichloromethane (0.1 M). This solution was transferred to a separatory funnel and washed twice with 1 M aq. KOH solution. The organic phase was dried over $Na_2SO_4$, concentrated to dryness, adsorbed onto silica gel, and subjected to column chromatography (Silica, Biotage prepack, EtOAc in hexanes) to afford the product benzoate, typically as a foamy semi-solid in 95-99% yield. HNMR and MS analysis were consistent with product.

Benzoate Cleavage

The starting benzoate from was dissolved in MeOH (0.1 M) and NaOH (10 equiv, 5% aq. solution) was added. The reaction mixture was warmed to 60° C. and stirred at that temperature for 0.5 hr. The MeOH was removed in vacuo and the aqueous layer was extracted with $CH_2Cl_2$ (4 times). The combined organic layers were dried over $Na_2SO_4$.and concentrated to afford an oil which was purified by column chromatography (silica, Biotage prepack, EtOAc/Hex) to afford the desired alcohol 5 in good to excellent yield. HNMR and MS analysis were consistent with product.

Ether Formation via Mitsunobu Reaction

The starting alcohol (5) triphenylphosphine (2.0 equiv.), and the starting phenol (5.0 equiv.) were dissolved in toluene (0.4 M) in a round-bottom flask fitted with a magnetic stirbar and septa and the mixture was cooled to 0 C and stirred for 10 minutes at this temperature. In some cases, some phenol or alcohol remained undissolved and a small amount (5-10% of the total solvent volume) of THF was added to aid with solubility. DIAD (1.9 equiv) was added dropwise over 10 minutes at 0 C. The reaction mixture was warmed to ambient temperature and stirred for 24-48 hours. Reaction progress was monitored by TLC (EtOAc in hexanes as an eluent) and MS. Upon completion of the reaction, the solvent was removed in vacuo, affording an oil which was dissolved in dichloromethane (0.1 M). This solution was transferred to a separatory funnel and washed twice with a 1M aq. KOH solution. The organic phase was dried over $Na_2SO_4$, concentrated to dryness, adsorbed onto silica gel, and subjected to column chromatography (Silica, Biotage prepack, 10 to 25% EtOAc in hexanes) to afford the product 6 as a solid or a foam in moderate yield.

Removal of the BOC Group

The starting material 6 was dissolved in a very minimum of dioxane in a round-bottom flask fitted with a magnetic stirbar and this was cooled to 0 C. A solution of HCl (4.0 equiv, 4.0 M in dioxane) was added dropwise via syringe and the reaction was stirred for 0.5 h during which time, the reaction was allowed to warm to room temperature. Stirring was continued for an additional 0.5 hours if necessary. When all starting material was consumed (as judged by TLC using EtOAc in hexanes), the reaction was concentrated to dryness in vacuo and taken up in a minimum of a 5% (v/v)HOAc solution in MeOH. This solution was loaded onto an ion exchange column (Varian SCX) and purified using MeOH and eluting with 1M $NH_3$ in MeOH) to give the product amine 7 or 8 (as the free amine) as a colorless solid or oil which was pure by NMR and HPLC.

Formation of the Fumaric Acid Salt

The free amine was dissolved in a minimum of isopropanol in an appropriately sized round-bottom flask fitted with a magnetic stirbar. A solution of fumaric acid (0.96 equiv, 0.205 M in isopropanol) was added and the reaction mixture was vigorously stirred for 15 minutes. A portion of the solvent (30-40%) was allowed to evaporate under a stream of nitrogen to afford a solid or a gummy solid. The remainder of the solvent was removed in vacuo and MeCN (0.1 M) was added. The resulting reaction mixture was vigorously stirred for several hours during which time a white solid forms. The reaction mixture was heated until all of the solid dissolved and was allowed to (slowly) cool over 1 h to ambient temperature in an oil bath. The reaction mixture was filtered through filter paper and the product crystals (or amorphous solid) were collected and dried under vacuum.

Ether Formation via Mesylate Displacement (Alternative Procedure to Mitsunobu Reaction)

The starting alcohol 5 was dissolved in $CH_2Cl_2$ (0.4M) and $Et_3N$ (1.3 equiv) was added. The reaction mixture was cooled to 0° C. and methanesulfonyl chloride (1.2 equiv) was added dropwise. The mixture was stirred at 0° C. for 2 hr. The reaction was quenched by the addition of satd. aq. NH4Cl, diluted with an additional volume of $CH_2Cl_2$ and poured into a separatory funnel. 1.5M aq. HCl was used to wash the organic layer for 2 times. The organic phase was dried over $Na_2SO_4$, filtered, and concentrated in vacuo to afford the product mesylate which was used in the next step without additional purification. This material was dissolved in a suitable solvent such as acetonitrile or toluene and $K_2CO_3$ (3.0 equiv) was added along with the appropriate phenol (1.3 equiv). The reaction mixture was heated to near the reflux point of the solvent either in a microwave reactor or on an oil bath. After heating for 12-60 hours, the reaction mixture was filtered and concentrated to afford a gummy residue which was purified by flash column chromatography to afford the desired ether product 6 or 9 in moderate yield.

Scheme D: Alternate procedure for the synthesis of biaryl and pyridyl-substituted morpholine derivatives (Formula II). General Procedure D.

concentrated and chromatographed (MPLC, silica gel, EtOAc in hexanes) to give the product (3), typically as a thin oil.

Formation of Fumarate Salt.

A solution of the BOC-protected morpholine derivative 3 in of $CH_2Cl_2$ was treated with 2 mL of trifluoroacetic acid. The solution was stirred at room temperature under $N_2$ for 3 h, concentrated then partitioned between $CH_2Cl_2$ and 10% aq.

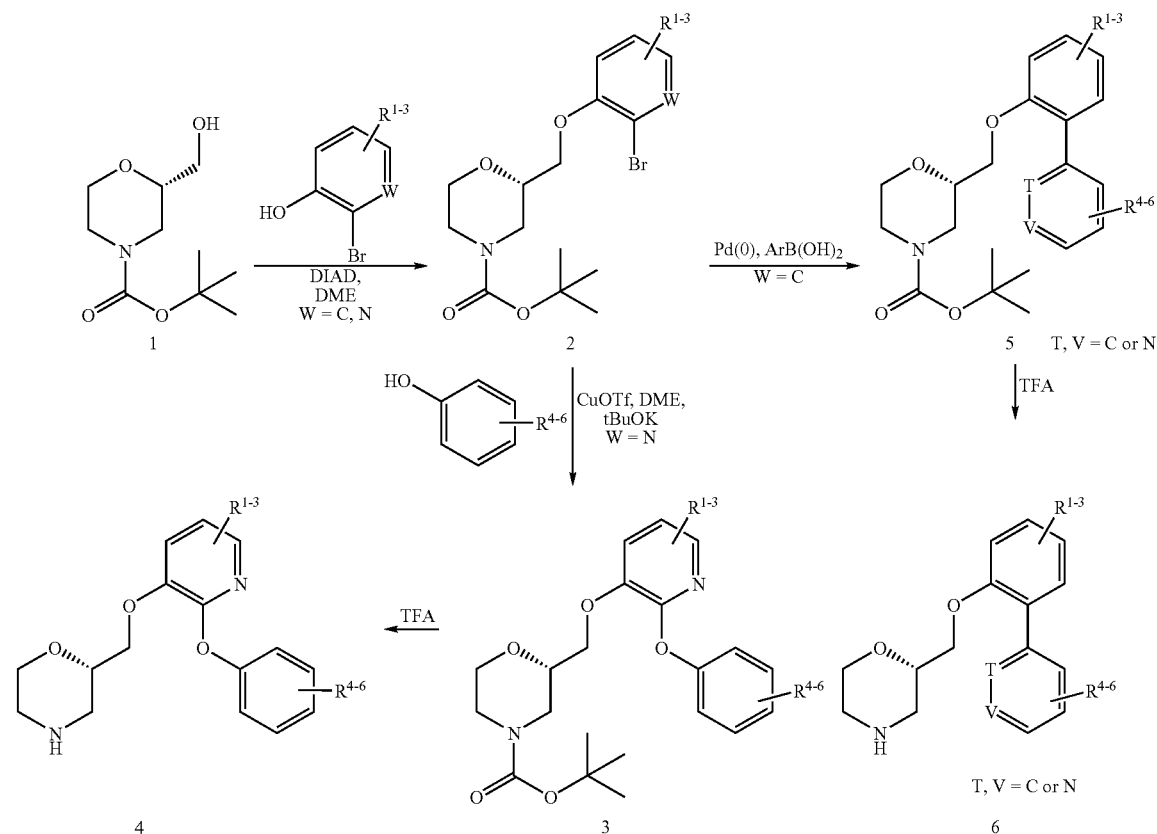

Etherification Via Mitsunobu Reaction

To a stirring mixture at room temperature of either (R) or (S)-2-hydroxymethyl-morpholine-4-carboxylic ac id, tert-butyl ester (1), the appropriate phenol (e.g. 2-bromophenol, 2-bromo-3-pyridinol, or a substituted analog), and triphenylphosphine, in DME was added dropwise diisopropyl azodicarboxylate. The solution was stirred and heated at 40° C. for 24 h, concentrated (to remove most of the DME), then suspended into diethyl ether. The solid that formed was filtered. The filtrate was concentrated and chromatographed (MPLC, silica gel, EtOAc in dichloromethane) to give the product (2), typically as a yellow or colorless oil.

Biaryl Ether Formation

To a stirred solution of the aryl bromide 2 and the appropriate phenol in DME was added potassium tert-butoxide and Copper (I) triflate benzene complex. The mixture was stirred and heated to 100° C. for 24 hours. The reaction was then concentrated (to remove most of the DME), and suspended into diethyl ether and water. This mixture was filtered through a pad of Celite and the pad was washed with additional diethyl ether. The layers were separated and the organic layer was washed with 2 N NaOH (2×), sat. $KH_2PO_4$, and brine solutions. The organic extract was dried with $Na_2SO_4$, filtered, $NH_4OH$ solution. The layers were separated and the organic extract was dried ($Na_2SO_4$), filtered and concentrated. The sample was converted to the fumaric acid salt in 2-propanol from which it crystallized to give the product 4 as its fumarate salt (white solid).

Additional debenzylation and alternate etherification for diphenyl ether formation without pyridine ring: (W=C)

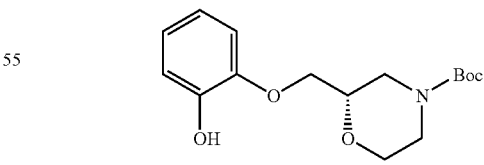

Additional debenzylation reaction: To a solution of (S)-2-(2-benzyloxy-phenoxymethyl)-morpholine-4-carboxylic acid, tert-butyl ester (obtained as above, General Procedure D) in ethanol was treated with 10% Pd/C. The room temperature sample was hydrogenated at balloon pressure for 2 h, filtered then concentrated. The sample was dissolved into EtOAc, washed with sat. $KH_2PO_4$ and brine solutions, dried (MgSO$_4$), filtered and concentrated to give (S)-2-(2-hydroxyphenoxymethyl)-morpholine-4-carboxylic acid, tert-butyl ester as a light yellow oil.

Alternate diphenyl ether formation: The procedure of David Evans, et al., *Tetrahedron Letters* 1998, 39, 2937-2940 was followed. A mixture of 2, arylboronic acid, copper (II) acetate, pyridine, and 4 Å activated powdered molecular sieves in CH$_2$Cl$_2$ was stirred at room temperature under ambient atmosphere for 5 days. The sample was diluted with EtOAc, stirred at room temperature for 2 h then filtered through a pad of Celite. The filtrate was washed with 1 N NaOH (2×), sat. KH$_2$PO$_4$ and brine solutions, dried (MgSO$_4$), filtered and concentrated. The crude sample was chromatoghaphed (MPLC, silica gel, EtOAc in hexanes) to give the product diphenyl ether 3.

Biphenyl Version of General Procedure D

To a mixture of aryl bromide 2, in degassed ethanol, tetrakis(triphenylphosphine) palladium(0), potassium carbonate, and the appropriate boronic acid were added. The reaction mixture was heated under reflux for 18 h, cooled to room temperature, the contents were filtered and the filtrate was concentrated. The residue was dissolved in ethyl acetate (100 mL), washed with water and brine. The solvent was removed under reduced pressure and the product was purified on a column of silica gel using ethyl acetate in hexane to give compounds 5 which were deprotected in the usual way.

General Procedure E:

Scheme E. General Procedure for the Synthesis of Chiral Morpholine Derivatives.

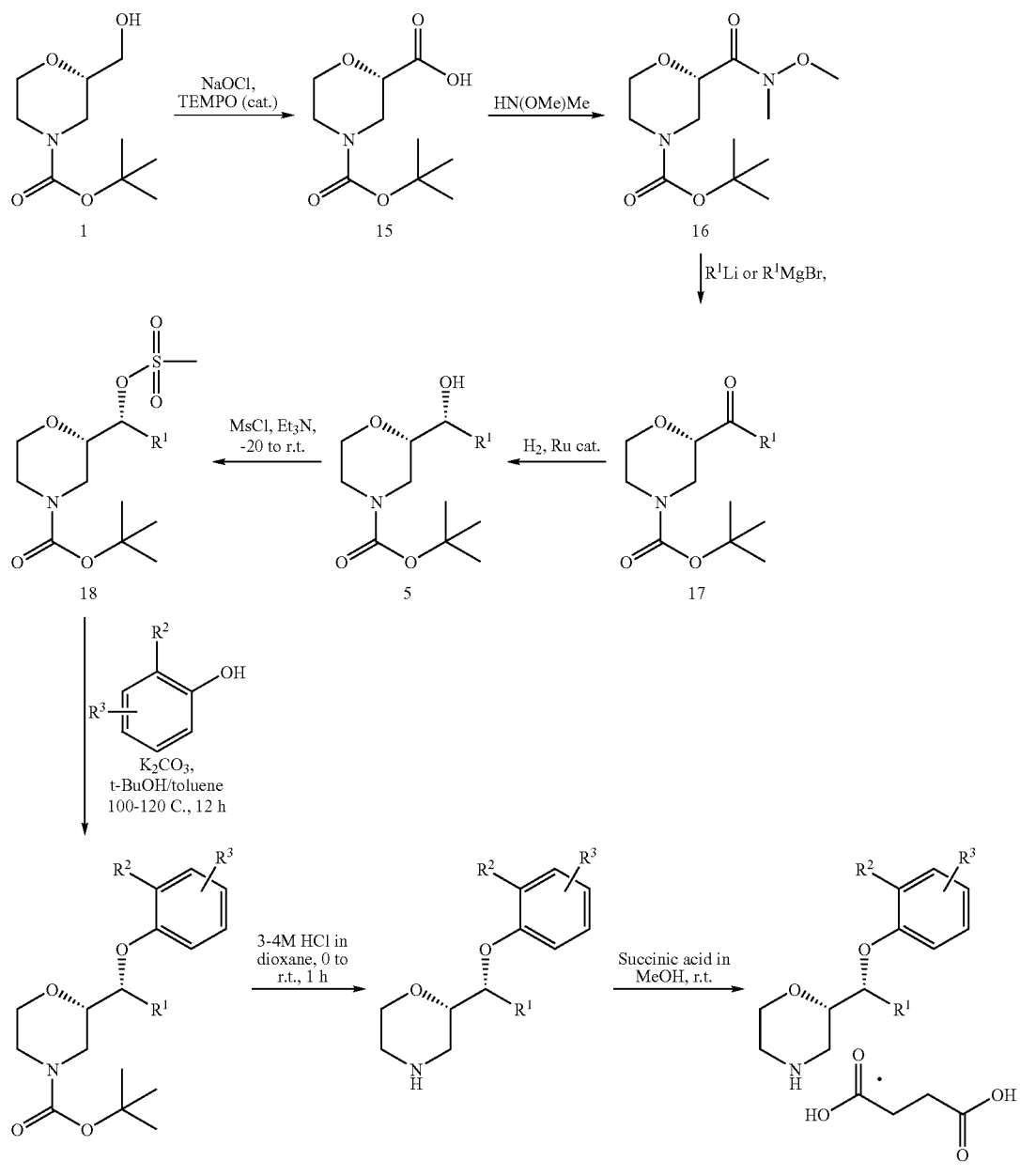

Oxidation of N—BOC-morpholine Alcohol

The appropriate S chiral morpholine alcohol 1 (15 g) was dissolved in a suitable amount dichloromethane and, TEMPO (160 mg), KBr (650 mg), and TBACl (1 g) were dissolved in a mixture of DCM (950 mL) and 40 mL 1 M NaHCO$_3$. The reaction mixture was cooled to 0 C and a solution of NaOCl (13%, 300 mL), 300 mL satd NaCl, and 180 mL NaHCO$_3$ was added dropwise over a period of 45 minutes. After stirring the resulting mixture for another 1.5 hours, it was washed with CH$_2$Cl$_2$ (4×500 mL). The aq. layer was cautiously acidified to pH 2 with 1M HCl and extracted with CH$_2$Cl$_2$. The combined organics were dried and concentrated to give a white solid. The acid thus obtained gives a good result in the subsequent coupling reaction.

Preparation of Weinreb Amide:

The acid 15, (32 g) was dissolved in 400 mL dichloromethane along with, the amine hydrochloride (15.1 g), triethylamine (35 g), and this solution was cooled to 0-5 C. To this reaction mixture was added phosphoric acid cyclic anhydride (97 g) over 90 minutes at 0-5 C. The reaction mixture was stirred for 1.5 hrs total and quenched with 250 ml of 20% K$_2$CO$_3$ solution at <15 C. The organic phase was separated and washed with 2×400 ml 10% K$_2$CO$_3$ to afford, after removal of solvent, 35.7 g of the desired amide 16 as a colorless oil (94%)

Preparation of Ketone:

Preparation of 2-(Pyridine-2-carbonyl)-morpholine-4-carboxylic acid tert-butyl ester as a representative example. 2-pyridyl iodide (5.5 g) was dissolved in THF and cooled to −20 C. EtMgBr (3.3 g) was added dropwise over 10 minutes as a solution in THF and stirring was continued for 30 minutes at −20 C. The solution became dark yellow. The amide 16 (4 g) was added to this solution as a solution in THF (8 mL) and the reaction mixture was held at −30 C and stirred for 30 minutes. Water was poured into the reaction mixture while it was still cold (100 mL) and quenched with NH$_4$Cl (aq) (50 mL). Extraction into EtOAc (3×75 mL) and concentration gave an solid which was purified on a 40 g Biotage prepack column (15% EtOAc in hexanes) to give the desired product as a slightly yellow, waxy solid.

Reduction:

Preparation of 2-(Hydroxy-pyridin-2-yl-methyl)-morpholine-4-carboxylic acid tert-butyl ester as a representative example. In a glove box in a sealed tube the reactants (1.15 g ketone, 0.1 g K$_2$CO$_3$) were dissolved in THF and isopropanol along with 0.001 g of Ru (S) cat (0.02 mol % eq) (Strem cat #44-0211 lot # B7081103). This was stirred under 50 psi H2 at RT overnight. The reaction was removed from the glovebox, filtered (the solid K$_2$CO$_3$) through syringe filter containing 3 g silica, and concentrated to dryness under reduced pressure to afford a yellow oil which was pure by NMR. Upon standing, the oil solidified to a fluffy solid which was used in the next steps without further purification. NMR analysis can be used to estimate the ratio of diastereoisomers present in the crude reduction mixture.

Formation of and Displacement of Mesylate or Mitsunobu Reaction:

2-[(2-Ethoxy-phenoxy)-pyridin-2-yl-methyl]-morpholine-4-carboxylic acid tert-butyl ester was prepared following the protocols outlined for General Procedure C.

Removal of Boc Group and Salt Formation:

2-[(2-Ethoxy-phenoxy)-pyridin-2-yl-methyl]-morpholine fumarate was prepared following the protocols outlined for General Procedure C.

Formation of Succinate Salt:

The free morpholine 7 was dissolved in a minimum amount of Et2O. Occasionally, a small amount of isopropanol was added in order to dissolve the morpholine completely. A 0.25 M solution of succinic acid in isopropanol (1.0 equiv. of acid) was added slowly dropwise with stirring. After several minutes, crystalline solid began to precipitate from the reaction mixture. After standing for 2 hours, the precipitate was filtered and dried to afford a 1:1 adduct of succinic acid and the morpholine derivative.

Scheme F (General Procedure F)

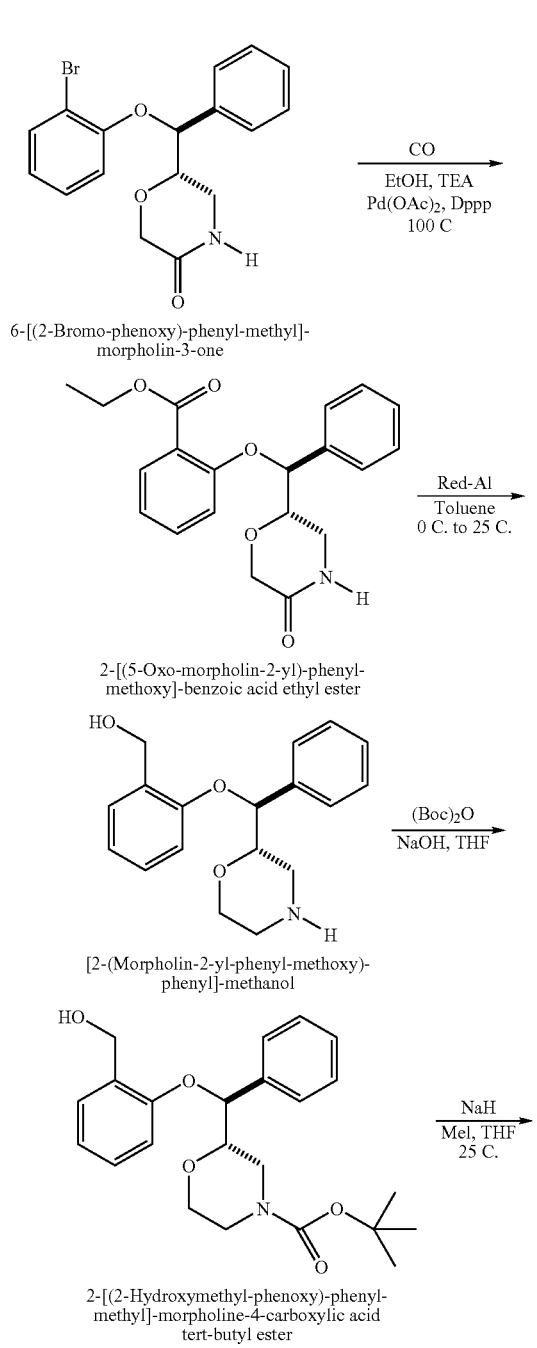

6-[(2-Bromo-phenoxy)-phenyl-methyl]-morpholin-3-one

2-[(5-Oxo-morpholin-2-yl)-phenyl-methoxy]-benzoic acid ethyl ester

[2-(Morpholin-2-yl-phenyl-methoxy)-phenyl]-methanol

2-[(2-Hydroxymethyl-phenoxy)-phenyl-methyl]-morpholine-4-carboxylic acid tert-butyl ester -continued

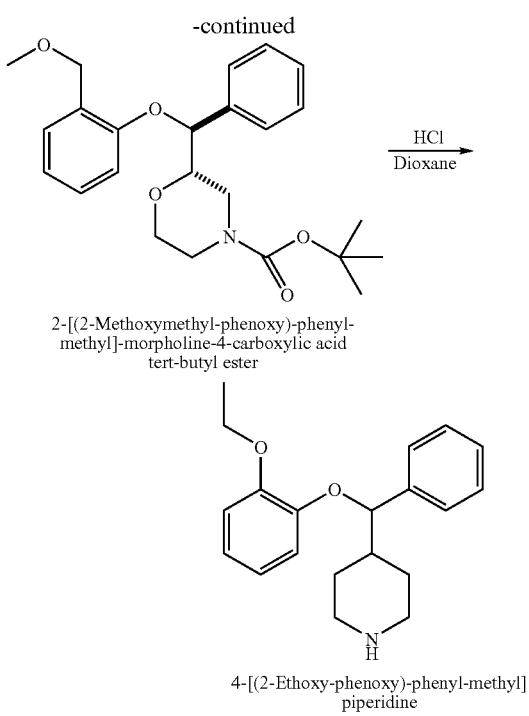

2-[(2-Methoxymethyl-phenoxy)-phenyl-methyl]-morpholine-4-carboxylic acid tert-butyl ester 4-[(2-Ethoxy-phenoxy)-phenyl-methyl]piperidine General Procedure F:

Preparation of 2-[(5-Oxo-morpholin-2-yl)-phenyl-methoxy]-benzoic acid ethyl ester.

6-[(2-Bromo-phenoxy)-phenyl-methyl]-morpholin-3-one (0.82 g) was taken up in ethanol (40 mL). Palladium acetate (0.051 g) was added, followed by DPPP (0.112 g) and TEA (0.63 mL), and the reaction was placed under a CO atmosphere and heated at 100 C. An second charge of catalyst was added at 60 h, and again at 74 h. After 88 h, the mixture was cooled, filtered, and concentrated to give a dark red oil. The oil was taken up in DCM, concentrated onto silica, and purified by silica chromatography (Hexane/EtOAc 95:5 to 40:60). Fractions containing the desired product were combined and concentrated to give 0.66 g of 2-[(5-Oxo-morpholin-2-yl)-phenyl-methoxy]-benzoic acid ethyl ester as an orange oil (83% yield, M+1=356.1).

Preparation of [2-(Morpholin-2-yl-phenyl-methoxy)-phenyl]-methanol

2-[(5-Oxo-morpholin-2-yl)-phenyl-methoxy]-benzoic acid ethyl ester (0.66 g) was taken up in 10 mL toluene, and cooled to 0 C for the addition of Red-Al (2.8 mL, 5 equiv). The mixture was allowed to warm to room temperature. After 12 h, 2 mL 2 N NaOH was added, and the mixture was stirred at room temperature for 30 min, extracted with toluene (2×5 mL). The organics were combined, dried over $MgSO_4$, filtered and concentrated. The residual oil was taken up in DCM, and pumped onto silica, and purified by MPLC in DCM/MeOH+0.1 $NH_4OH$. Fractions containing the desired compound were combined and concentrated. 0.287 g of [2-(Morpholin-2-yl-phenyl-methoxy)-phenyl]-methanol as a pale yellow oil (51% yield, M+1=300.1).

Preparation of 2-[(2-Hydroxymethyl-phenoxy)-phenyl-methyl]-morpholine-4-carboxylic acid tert-butyl ester

[2-(Morpholin-2-yl-phenyl-methoxy)-phenyl]-methanol (0.287 g) alcohol was taken up in THF, and NaOH (1.2 mL, 1M, 1.1 equiv.) was added followed by di-t-butyl dicarbonate (0.23 g, 1.1 equiv). The mixture was stirred at room temperature for 12 h. The THF was then removed by rotary evaporation, and the residual oil was partitioned between water and ether. The layers were separated, and the aqueous layer was extracted with ether (2×15 mL). The organics were combined and dried over $MgSO_4$, filtered and concentrated to give 0.44 g of 2-[(2-Hydroxymethyl-phenoxy)-phenyl-methyl]-morpholine-4-carboxylic acid tert-butyl ester (114% crude yield).

Preparation of 2-[(2-Methoxymethyl-phenoxy)-phenyl-methyl]-morpholine-4-carboxylic acid tert-butyl ester 2-[(2-Hydroxymethyl-phenoxy)-phenyl-methyl]-morpholine-4-carboxylic acid tert-butyl ester (0.44 g) was taken up in THF (10 mL) and placed in a room temperature bath for the addition of NaH (0.05 g). The mixture was stirred for 10 min, and then MeI (0.17 g) was added and stirred at room temperature for 3 h. The mixture was again treated with NaH and MeI and stirred at room temperature for 48 h. Starting material was still present, so the mixture was treated with NaH. MeI was passed through a plug of basic alumina and then added. After 3 h, the reaction was carefully quenched by the addition of water. The mixture was extracted with ether (3×30 ml), and the organics were combined, washed with brine (1×20 ml), dried over $MgSO_4$, filtered and concentrated. The colorless oil was taken up in DCM and pumped onto silica and then purified by MPLC (Hexane:EtOAc 95:5 to 40:60). Fractions containing the desired product were combined and concentrated to give 0.317 g of Preparation of 2-[(2-Methoxymethyl-phenoxy)-phenyl-methyl]-morpholine-4-carboxylic acid tert-butyl ester (70% yield).

Preparation of 4-[(2-Ethoxy-phenoxy)-phenyl-methyl]-piperidine

2-[(2-Methoxymethyl-phenoxy)-phenyl-methyl]-morpholine-4-carboxylic acid tert-butyl ester (0.761 g) was taken up in 1 M HCl in dioxane (7.4 mL) and stirred at room temperature for 12 h. The dioxane was removed, and the residual tacky solid was taken up in DCM, washed with 1 M NaOH, dried over $MgSO_4$, filtered and concentrated onto silica. The material was purified via MPLC (DCM/MeOH+ 1% $NH_4OH$ 95:5 to 75:25. The collected product was not clean, so it was purified by preparative HPLC to give 0.077 g of 4-[(2-Ethoxy-phenoxy)-phenyl-methyl]-piperidine (21% yield, M+1=312.2).

The compounds of the formulae I, II, or III and their pharmaceutically acceptable salts can be administered to mammals via either the oral, parenteral (such as subcutaneous, intravenous, intramuscular, intrasternal and infusion techniques), rectal, buccal or intranasal routes. In general, these compounds are most desirably administered in doses ranging from about 0.1 mg to about 1000 mg per day, in single or divided doses (i.e., from 1 to 4 doses per day), although variations will necessarily occur depending upon the species, weight and condition of the patient being treated and the patient's individual response to said medicament, as well as on the type of pharmaceutical formulation chosen and the time period and interval at which such administration is carried out. However, a dosage level that is in the range of about 25 mg to about 100 mg per day is most desirably employed. In some instances, dosage levels below the lower limit of the aforesaid range may be more than adequate, while in other cases still larger doses may be employed without causing any harmful side effects, provided that such higher dose levels are first divided into several small doses for administration throughout the day.

The compounds of the present invention may be administered alone or in combination with pharmaceutically acceptable carriers or diluents by any of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, jellies, gels, pastes, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the weight ratio of the novel compounds of this invention to the pharmaceutically acceptable carrier will be in the range from about 1:6 to about 2:1, and preferably from about 1:4 to about 1:1.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art.

This invention relates to methods of treating a central nervous system disorder or condition such as ADHD, anxiety, depression, schizophrenia and the other disorders referred to in the description of the methods of the present invention, wherein a novel compound of this invention and one or more of the other active agents referred to above (e.g., an NK1 receptor antagonist, an anxiolytic an antipsychotic agent, tricyclic antidepressant, 5HT1B receptor antagonist, or serotonin reuptake inhibitor) are administered together, as part of the same pharmaceutical composition, as well as to methods in which such active agents are administered separately as part of an appropriate dose regimen designed to obtain the benefits of the combination therapy. The appropriate dose regimen, the amount of each dose of an active agent administered, and the specific intervals between doses of each active agent will depend upon the subject being treated, the specific active agent being administered and the nature and severity of the specific disorder or condition being treated. In general, the novel compounds of this invention, when used as a single active agent or in combination with another active agent, will be administered to an adult human in an amount from about 3 mg to about 300 mg per day, in single or divided doses, preferably from about 25 to about 100 mg per day. Such compounds may be administered on a regimen of up to 6 times per day, preferably 1 to 4 times per day, especially 2 times per day and most especially once daily. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

A proposed daily dose of an atypical anti psychotic, preferably piprasidone, in the combination methods and compositions of this invention, for oral, parenteral or buccal administration to the average adult human for the treatment of the conditions referred to above, is from about 0.1 mg to about 2000 mg, preferably from about 1 mg to about 200 mg of an atypical anti psychotic per unit dose, which could be administered, for example, 1 to 4 times per day. A proposed daily dose of a 5HT1B receptor antagonist in the combination methods and compositions of this invention, for oral, parenteral, rectal or buccal administration to the average adult human for the treatment of the conditions referred to above, is from about 0.01 mg to about 2000 mg, preferably from about 0.1 mg to about 200 mg of the 5HT1B receptor antagonist per unit dose, which could be administered, for example, 1 to 4 times per day.

For intranasal administration or administration by inhalation, the novel compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch. Formulations of the active compounds of this invention for treatment of the conditions referred to above in the average adult human are preferably arranged so that each metered dose or "puff" of aerosol contains 20 µg to 1000 µg of active compound. The overall daily dose with an aerosol will be within the range 100 µg to 10 mg. Administration may be several times daily, for example 2, 3, 4 or 8 times, giving for example, 1, 2 or 3 doses each time.

The ability of the compounds of this invention to bind to the hNET and serotonin SERT receptor can be determined using conventional radioligand receptor binding assays. The receptors can be heterologously expressed in cell lines and experiments conducted in membrane preparations from the cell lines using procedures outlined below. $IC_{50}$ concentrations can be determined by nonlinear regression of concentration-dependent reduction in specific binding. The Cheng-Prussoff equation can be used to convert the $IC_{50}$ to Ki concentrations.

hNET Receptor Binding:

Cell pastes of HEK-293 cells transfected with the human norepinephrine transporter were supplied by the Pfizer Ann Arbor Protein Expression and Production group. Pellets were resuspended in 400 to 700 ml of Krebs-HEPES assay buffer (25 mM HEPES, 122 mM NaCl, 3 mM KCl, 1.2 mM MgSO$_4$, 1.3 mM CaCl$_2$, and 11 mM glucose, pH 7.4) with a Polytron homogenizer at setting 7 for 30 sec. Aliquots of membranes (5 mg/ml protein) were stored in liquid nitrogen until used.

The binding assay was set up in Beckman deep-well polypropylene plates with a total volume of 250 µl l containing: drug ($10^{-5}$M to $10^{-12}$M), cell membranes, and 50 µM [$^{125}$I]-RTI-55 (Perkin Elmer, NEX-272; specific activity 2200 Ci/mmol). The reaction was incubated by gentle agitation for 90 min at room temperature and was terminated by filtration through Whatman GF/C filter plates using a Brandel 96-well plate harvester. Scintillation fluid (100 µl l) was added to each well, and bound [$^{125}$I]-RTI-55 was determined using a Wallac Trilux Beta Plate Counter. Test compounds were run in duplicate, and specific binding was defined as the difference between binding in the presence and absence of 10 µM desipramine.

Excel and GraphPad Prism software were used for data calculation and analysis. IC$_{50}$ values were converted to K$_i$ values using the Cheng-Prusoff equation.

hSERT Receptor Binding:

Cell pastes of HEK-293 cells transfected with the human seritonin transporter were supplied by the Pfizer Ann Arbor Protein Expression and Production group. Pellets were resuspended in 400 to 700 ml of Krebs-HEPES assay buffer (25 mM HEPES, 122 mM NaCl, 3 mM KCl, 1.2 mM MgSO$_4$, 1.3 mM CaCl$_2$, and 11 mM glucose, pH 7.4) with a Polytron homogenizer at setting 7 for 30 sec. Aliquots of membranes (5 mg/ml protein) were stored in liquid nitrogen until used.

The binding assay was set up in Beckman deep-well polypropylene plates with a total volume of 250 µl l containing: drug ($10^5$M to $10^{-12}$M), cell membranes, and 50 µM [$^{125}$I]-RTI-55 (Perkin Elmer, NEX-272; specific activity 2200 Ci/mmol). The reaction was incubated by gentle agitation for 90 min at room temperature and was terminated by filtration through Whatman GF/C filter plates using a Brandel 96-well plate harvester. Scintillation fluid (100 µl l) was added to each well, and bound [$^{125}$I]-RTI-55 was determined using a Wallac Trilux Beta Plate Counter. Test compounds were run in duplicate, and specific binding was defined as the difference between binding in the presence and absence of 10 µl M citalopram.

Excel and GraphPad Prism software were used for data calculation and analysis. IC$_{50}$ values were converted to K$_i$ values using the Cheng-Prusoff equation.

The hNET and SERT activities of compounds of the present invention are set forth in Table 1.

TABLE 1

| Example # | hNET (Ki) | SERT (Ki) |
| --- | --- | --- |
| 1 | 9.9 | 3942 |
| 2 | 6.3 | 564 |
| 3 | 33 | 1581 |
| 4 | 1.6 | 708 |
| 5 | 13 | 1176 |
| 6 | 11 | 3227 |
| 7 | 17 | 6610 |
| 8 | 4.2 | 4713 |
| 9 | 15 | 967 |
| 10 | 689 | 10000 |
| 11 | 1.8 | 452 |
| 12 | 6.7 | 6.4 |
| 13 | 18 | 4097 |
| 14 | 61 | 10000 |
| 15 | 15 | 3772 |
| 16 | 99 | 4505 |
| 18 | 133 | 72 |
| 19 | 1015 | 74 |
| 20 | 593 | 10000 |
| 21 | 6.8 | 2500 |
| 22 (2S, 3R) | 4816 | 6671 |
| 22 (2S, 3S) | 12 | 10000 |
| 23 | 51 | 2629 |
| 24 | 210 | 7722 |
| 25 | 124 | 10000 |
| 26 | 359 | 2437 |
| 27 | 7903 | 412 |
| 28 | 8414 | 1409 |
| 29 | 154 | 10000 |
| 30 | 41 | 10000 |
| 31 | 85 | 348 |
| 32 | 36 | 10000 |
| 33 | 22 | 2410 |
| 34 | 141 | 184 |
| 35 | 11 | 605 |
| 36 | 3.7 | 471 |
| 37 | 12 | 163 |
| 38 | 517 | 4099 |
| 39 | 3.7 | 475 |
| 40 | 317 | 828 |
| 41 | 17 | 17 |
| 42 | 68 | 4941 |
| 43 | 172 | 19 |
| 44 | 5.3 | 1359 |
| 45 | 10 | 45 |
| 46 | 6.5 | 5632 |
| 47 | 8.4 | 52 |
| 48 | 31 | 10 |
| 49 | 8.9 | 729 |
| 50 | 5.2 | 6260 |
| 51 | 16 | 10000 |
| 52 | 1617 | 1351 |
| 53 | 5.9 | 259 |
| 54 | 1306 | 10000 |
| 55 | 12 | 2244 |
| 56 | 41 | 2463 |
| 57 | 24 | 94 |
| 58 | 7.4 | 965 |
| 59 | 61 | 206 |
| 60 | 14 | 78 |
| 61 | 68 | 6603 |
| 62 | 12 | 65 |
| 63 | 28 | 2538 |
| 64 | 119 | 10000 |
| 65 | 85 | 1195 |
| 66 | 81 | 176 |
| 67 | 21 | 93 |
| 68 | 19 | 660 |
| 69 | 26 | 1894 |
| 70 | 11 | 818 |
| 71 | 50 | 65 |
| 73 | 595 | 10000 |
| 74 | 55 | 10000 |
| 75 | 22 | 849 |
| 76 | 64 | 349 |
| 77 | 3163 | 10000 |
| 78 | 7974 | 10000 |
| 79 | 10 | 9646 |
| 80 | 7.5 | 3669 |
| 81 | 9.6 | 4320 |
| 82 | 11 | 2609 |
| 83 | 3.9 | 3116 |
| 84 | 7.3 | 4865 |
| 85 | 37 | 869 |
| 86 | 14 | 8085 |
| 87 | 2893 | 953 |
| 88 | 633 | 10000 |
| 89 | 4110 | 10000 |
| 90 | 211 | 5045 |
| 91 | 19 | 2289 |

TABLE 1-continued
| Example # | hNET (Ki) | SERT (Ki) |
|---|---|---|
| 92 | 35 | 1452 |
| 93 | 11 | 5603 |
| 94 | 8 | 811 |
| 95 | 3 | 3410 |
| 96 | 12 | 4447 |
| 97 | 9 | 471 |
| 98 | 22 | 1140 |
| 99 | 880 | 1271 |
| 100 | 152 | 10000 |
| 101 | 66 | 912 |
| 102 | 82 | 5740 |
| 103 | 13 | 6073 |
| 104 | 2386 | 9786 |
| 105 | 1500 | 5587 |
| 106 | 54 | 10000 |
| 107 | 27 | 3675 |
| 108 | 28 | 676 |
| 109 | 16 | 364 |
| 110 | 8.57 | 356 |
| 111 | 105 | 237 |
| 112 | 17 | 105 |
| 113 | 15 | 71 |
| 114 | 35 | 75 |
| 116 | 63 | 1333 |
| 118 | 1137 | 10000 |
| 119 | 23 | 66 |
| 120 | 10 | 10000 |
| 121 | 470 | 10000 |
| 122 | 11 | 44 |
| 123 | 935 | 4116 |
| 124 | 30 | 346 |
| 125 | 11 | 10000 |
| 126 | 32 | 10000 |
| 127 | 7 | 6280 |
| 128 | 11 | 3325 |
| 129 | 8 | 4473 |
| 130 | 457 | 7057 |
| 131 | 388 | 99 |
| 132 | 18 | 6117 |
| 133 | 1457 | 9059 |
| 134 | 18 | 10000 |
| 135 | 32 | 4483 |
| 136 | 102 | 6135 |
| 137 | 9 | 1813 |
| 138 | 1609 | 3822 |
| 139 | 1189 | 1139 |
| 140 | 71 | 763 |
| 141 | 40 | 2745 |
| 142 | 49 | 4538 |
| 143 | 896 | 3319 |
| 144 | 304 | 7221 |
| 145 | 45 | 4138 |
| 146 | 20 | 3704 |
| 147 | 2568 | 2533 |
| 148 | 69 | 10000 |
| 149 | 9 | 2311 |
| 150 | 20 | 2025 |
| 151 | 4 | 3290 |
| 152 | 9 | 1938 |
| 153 | 14 | 6319 |
| 154 | 12 | 2524 |
| 155 | 5 | 768 |
| 156 | 14 | 801 |
| 157 | 4 | 2573 |
| 158 | 6 | 10000 |
| 159 | 7 | 7368 |
| 160 | 6 | 6503 |
| 161 | 5 | 3877 |
| 162 | 5 | 263 |
| 163 | 13 | 446 |
| 164 | 13 | 3067 |
| 165 | 4 | 351 |
| 166 | 8 | 1349 |
| 167 | 8 | 2554 |
| 168 | 5 | 791 |
| 169 | 6 | 2982 |
| 170 | 11 | 4934 |
| 171 | 20 | 1039 |
| 172 | 24 | 9341 |
| 173 | 12 | 10000 |
| 174 | 18 | 7517 |
| 175 | 15 | 7640 |
| 176 | 5 | 3417 |
| 177 | 7 | 1961 |
| 178 | 3 | 61 |
| 179 | 18 | 2553 |
| 180 | 9 | 8234 |
| 181 | 225 | 4904 |
| 182 | 31 | 7084 |
| 183 | 7 | 5344 |
| 184 | 6 | 460 |
| 185 | 8 | 201 |
| 186 | 8 | 1255 |
| 187 | 15 | 224 |
| 188 | 14 | 2212 |
| 189 | 147 | 5218 |
| 190 | 6 | 4338 |
| 191 | 6 | 5832 |
| 192 | 38 | 1880 |
| 193 | 3 | 707 |
| 194 | 9 | 2560 |
| 195 | 10 | 7057 |
| 196 | 9 | 10000 |
| 197 | 18 | 811 |
| 198 | 30 | 62 |
| 199 | 8 | 2942 |
| 200 | 9546 | 10000 |
| 201 | 171 | 10000 |
| 202 | 45 | 722 |
EXAMPLES
Example 1
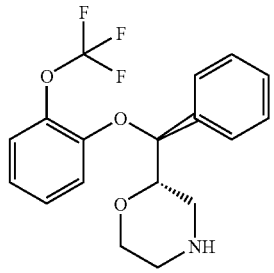
(S)-2-[(S)-Phenyl-(2-trifluoromethoxy-phenoxy)-methyl]-morpholine was synthesized from benzyl glycidol and 2-trifluoromethoxyphenol according to General Procedure A (Scheme A) and was isolated as a gummy oil. $^1$H NMR (CDCl$_3$) δ: 7.22 (m, 5H), 7.07 (d, 1H), 6.91 (dt, 1H), 6.72 (m, 2H), 5.04 (d, 1H), 3.82 (m, 2H), 3.51 (m, 1H), 2.65 (m, 2H), 2.53 (m, 1H), 2.46 (t, 1H), 1.61 (s, 1H). MS(EI): calculated: [C$_{18}$H$_{18}$O$_3$F$_3$N] 353, Found: [M+H]: 354. Elemental Analysis: calculated: C, 61.19%; H, 5.10%; N, 3.97%. Found: C, 60.33%; H, 5.04%; N, 3.82%.

Example 2

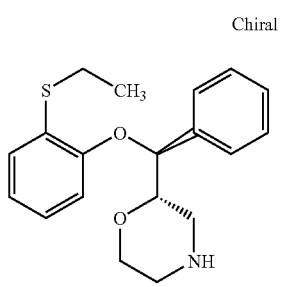

(S)-2-[(S)-(2-Ethylsulfanyl-phenoxy)-phenyl-methyl]-morpholine was synthesized from 2-Ethylsulfanyl-phenol according to general procedure A and was isolated as a gummy oil. MS (APCI): 330 [M+H]$^+$.

Example 3

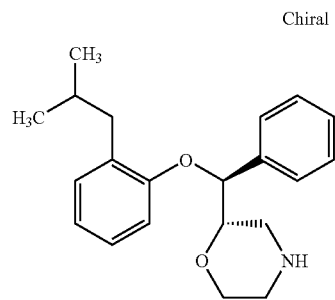

(S)-2-[(S)-(2-isobutyl-phenoxy)-phenyl-methyl]-morpholine was synthesized from 2-Isobutyl-phenol according to general procedure A and was isolated as a gummy oil. MS (APCI): 326 [M+H]$^+$.

Example 4

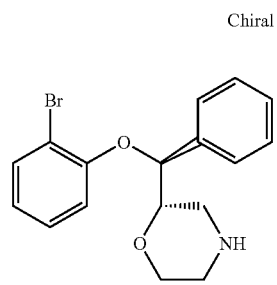

(S)-2-[(S)-(2-Bromo-phenoxy)-phenyl-methyl]-morpholine was synthesized from 2-Bromophenol according to general procedure A with the following modification of the final reduction reaction.

Preparation of Morpholine Compound 2:

To a solution of bromomorpholinone 1 (1.0 g, 2.76 mmol) in 20 mL of THF was added 10 mL of 1.0 M borane in THF and the reaction mixture was stirred at room temperature for 18 h. Then the reaction mixture was quenched by adding 3 mL of 3.0 M hydrochloric acid solution and heated at 80° C. for 10

Scheme:

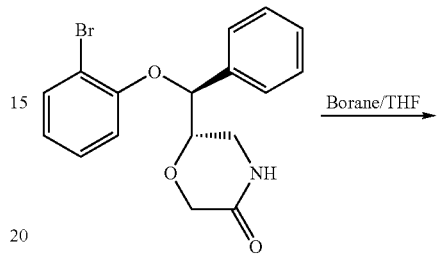

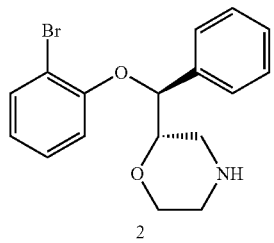

minutes. The reaction mixture was cooled to room temperature and basified with 2.0 M sodium hydroxide solution. The product was extracted with ethyl acetate (2×30 mL). The combined organic extract was washed with brine and dried over anhydrous sodium sulfate. The solvent was removed under reduced pressure and the product was purified on a column of silica gel (EtOAc: MeOH=9:1) to give 2-[(2-Bromo-phenoxy)-phenyl-methyl]-morpholine (2) as a thick oil (0.650 g, 67.6%). $^1$H NMR (CDCl$_3$) δ: 7.50 (d, 1H), 7.40-7.20 (m, 5H), 7.06 (m, 1H), 6.76 (m, 2H), 5.20 (d, 1H), 3.94 (m, 1H), 3.70 (m, 1H), 2.90-2.50 (m, 4H). MS (ES) m/z 347.96 [C$_{17}$H$_{18}$BrNO$_2$+H]$^+$. Analysis: Calcd for C$_{17}$H$_{18}$BrNO$_2$: C, 58.63; H, 5.21; N, 4.02. Found: C, 58.20; H, 5.12; N, 4.37.

Example 5

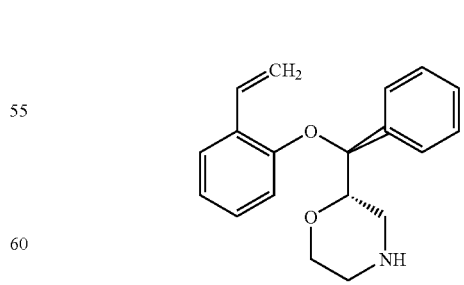

(S)-2-[(S)-Phenyl-(2-vinyl-phenoxy)-methyl]-morpholine was synthesized from 6-[(2-Bromo-phenoxy)-phenyl-methyl]-morpholin-3-one according to General Procedure A and General Procedure B as detailed below.

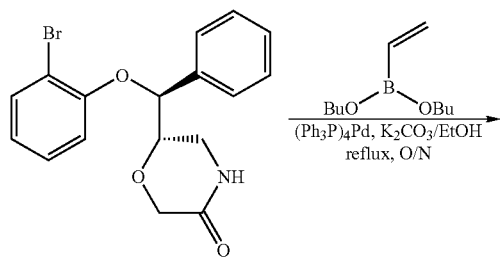

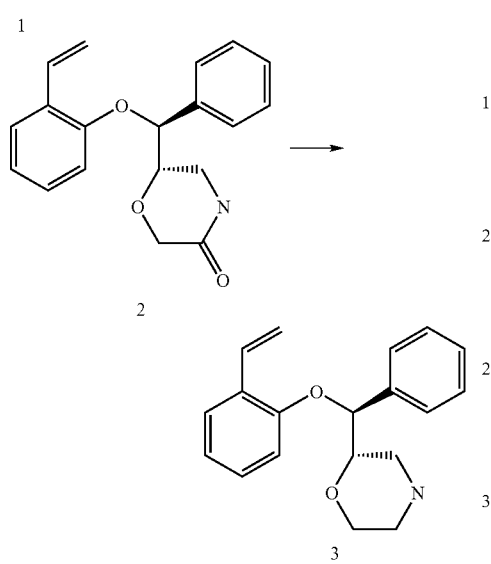

Synthesis of Compound 2

To a mixture of 1, (1.0 g, 2.76 mmol) in degassed ethanol (25 mL), tetrakis(triphenylphosphine)palladium(0) (0.319 g, 0.276 mmol), potassium carbonate (1.14 g, 8.28 g mmol), vinylboronic acid dibutyl ester (1.22 mL, 5.52 mmol) were added. The reaction mixture was heated under reflux for 18 h, cooled to room temperature, the contents were filtered and the filtrate was concentrated. The residue was dissolved in ethyl acetate (100 mL), washed with water and brine. The solvent was removed under reduced pressure and the product was purified on a column of silica gel using 70% ethyl acetate in hexane to give compound 2 as a colorless oil (0.351 g, 47%). $^1$H NMR (CDCl$_3$) δ: 7.46 (dd, 1H), 7.40-7.28 (m, 5H), 7.16 (dd, 1H), 7.03 (m, 1H), 6.89 (t, 1H), 6.67 (d, 1H), 6.45 (br s, 1H), 5.78 (dd, 1H), 5.31 (dd, 1H), 5.25 (d, 1H), 4.30 (ABq, 2H), 4.18 (m, 1H), 3.34 (t, 1H), 3.05 (td, 1H); MS (ES) 310.2 $[C_{19}H_{19}NO_3+H]^+$.

Preparation of Compound 3 (2-[Phenyl-(2-vinyl-phenoxy)-methyl]-morpholine)

To a solution of morpholinone 2 (0.255 g, 0.825 mmol) in toluene (10 mL), Red-Al (65% solution in toluene (0.8 mL, 2.55 mmol), was added dropwise at 0° C. over 20 min. The reaction mixture was stirred at 0-5° C. for 2.5 h. Excess Red-Al was destroyed by dropwise addition of 2 M NaOH solution (2.7 mL). The layers were separated and the aqueous layer was diluted with water (20 mL) and extracted with toluene (2×15 mL). The combined organic extract was washed with brine and dried over anhydrous Na$_2$SO$_4$. The solvent was removed under reduced pressure and the product was purified on a column of silica gel using 10% methyl alcohol in ethyl acetate to give morpholine compound 3 (2-[Phenyl-(2-vinyl-phenoxy)-methyl]-morpholine) as a viscous colorless oil (0.154 g, 63%). $^1$H NMR (CDCl$_3$) δ: 7.46-7.18 (m, 7H), 7.01 (m, 1H), 6.84 (t, 1H), 6.68 (d, 1H), 5.78 (dd, 1H), 5.29 (dd, 1H), 5.12 (d, 1H), 3.98-3.86 (m, 2H), 3.64 (dt, 1H), 2.86-2.72 (m, 2H), 2.66-2.54 (m, 2H); MS (ES) 296.1 $[C_{19}H_{21}NO_2+H]^+$; HPLC purity (94.3%); Analysis: Calcd. $C_{19}H_{21}NO_2 \cdot 0.5H_2O$: C, 74.91; H, 7.23; N, 4.60. Found: C, 75.41; H, 7.09; N, 4.95.

Example 6

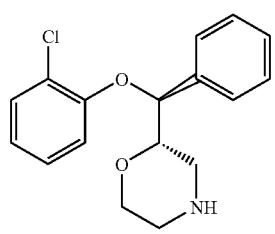

(S)-2-[(S)-(2-Chloro-phenoxy)-phenyl-methyl]-morpholine was synthesized from 2-chloro-phenol according to general procedure A and was isolated as a colorless liquid (Yield: 0.325 mg, 51%). $^1$H NMR (CDCl$_3$) δ: 7.40-7.35 (m, 6H), 7.00 (m, 1H), 6.80 (m, 2H), 5.20 (d, 1H), 3.90 (m, 2H), 3.65 (m, 1H), 2.90-2.80 (m, 2H), 2.70-2.60 (m, 2H), 1.65 (s, 1H). MS (ES) m/z 304.06 $[C_{17}H_{18}ClNO_2+H]^+$. Analysis: Calcd for $C_{17}H_{18}ClNO_2$: C, 67.21; H, 5.91; N, 4.61. Found: C, 66.51; H, 6.19; N, 5.51.

Example 7

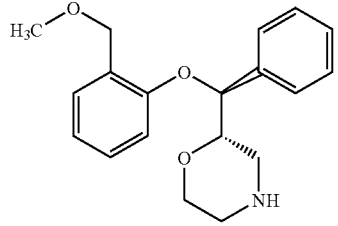

(S)-2-[(S)-(2-Methoxymethyl-phenoxy)-phenyl-methyl]-morpholine was synthesized from 2-bromophenol going through 6-[(2-Bromo-phenoxy)-phenyl-methyl]-morpholin-3-one according to General Procedures A and F and was isolated as a gummy oil. MS (APCI): 314 $[M+H]^+$.

Example 8

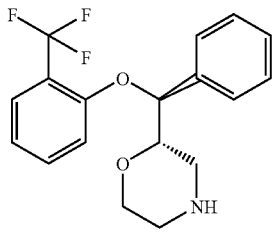

(S)-2-[(S)-Phenyl-(2-trifluoromethyl-phenoxy)-methyl]-morpholine was synthesized from 2-trifluoromethylphenol according to general procedure A and was isolated as colorless liquid (Yield: 0.36 mg, 65%). $^1$H NMR (CDCl$_3$) δ: 7.55 (m, 1H), 7.40-7.25 (m, 6H), 6.90 (m, 1H), 6.78 (d, 1H), 5.25 (d, 1H), 3.90 (m, 2H), 3.62 (m, 1H), 2.80-2.73 (m, 3H), 2.55-2.50 (m, 1H), 1.60 (br s, 1H). MS (ES) m/z 338.07 [C$_{17}$H$_{18}$ClNO$_2$+H]$^+$. Analysis: Calcd for C$_{18}$H$_{18}$F$_3$NO$_2$: C, 64.09; H, 5.38; N, 4.54. Found: C, 63.52; H, 5.44; N, 4.66.

Example 9

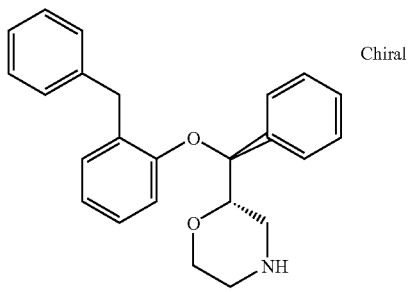

(S)-2-[(S)-(2-Benzyl-phenoxy)-phenyl-methyl]-morpholine was synthesized from 2-Benzylphenol according to general procedure A and was isolated as a thick oil. $^1$H NMR (400 MHz, CDCl$_3$) δ 7.16 (m, 11H), 7.00 (m, 1H), 6.80 (m, 1H), 6.64 (m, 1H), 5.10 (d, 1H), 4.10 (m, 2H), 3.92 (d, 1H), 3.78 (m, 1H), 3.62 (m, 1H), 2.78 (m, 2H), 2.44 (m, 2H), 1.76 (br s, 1H). (ES) m/z 360.18 [C$_{24}$H$_{25}$NO$_2$+H$^+$].

Example 10

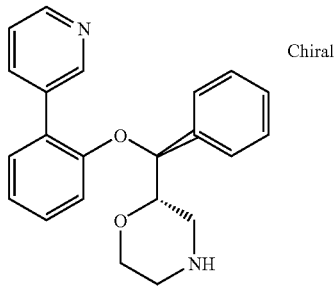

(S)-2-[(S)-Phenyl-(2-pyridin-4-yl-phenoxy)-methyl]-morpholine was synthesized from 6-[(2-Bromo-phenoxy)-phenyl-methyl]-morpholin-3-one and 4-pyridineboronic acid according to general procedures A and B and was isolated as a thick viscous gum. $^1$H NMR (CDCl$_3$) δ: 8.65 (d, 2H), 7.60 (d, 2H), 7.32-7.18 (m, 7H), 6.96 (m, 1H), 6.90 (d, 1H), 5.10 (d, 1H), 3.93 (d, 1H), 3.80 (m, 1H), 3.60 (m, 1H), 2.75 (m, 2H), 2.48 (m, 2H), 1.80 (br s, 1H). MS (ES) m/z 347.08 [C$_{22}$H$_{22}$N$_2$O$_2$+H]$^+$. Analysis: Calcd for C$_{22}$H$_{22}$N$_2$O$_2$: 0.5H$_2$O: C, 74.34; H, 6.52; N, 7.88. Found: C, 74.15; H, 6.84; N, 7.37.

Example 11

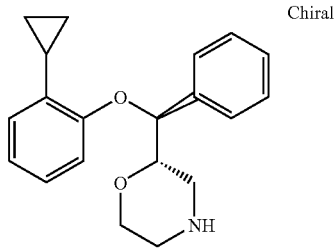

(S)-2-[(S)-(2-Cyclopropyl-phenoxy)-phenyl-methyl]-morpholine was synthesized from 6-[(2-Bromo-phenoxy)-phenyl-methyl]-morpholin-3-one and cyclopropyl boronic acid according to general procedures A and B and was isolated as a viscous colorless oil. $^1$H NMR (CDCl$_3$): δ 7.40-7.24 (m, 5H), 6.91 (m, 1H), 6.80 (m, 2H), 6.66 (d, 1H), 5.15 (d, 1H), 3.94 (m, 2H), 3.65 (dt, 1H), 2.85-2.59 (m, 4H), 2.32 (m, 1H), 0.99-0.89 (m, 2H), 0.74-0.59 (m, 2H); MS (ES) 310.1 [C$_{20}$H$_{23}$NO$_2$+H]$^+$; HPLC purity (98.6%); Analysis: Calc'd for C$_{20}$H$_{23}$NO$_2$: C, 77.64; H, 7.49; N, 4.53. Found: C, 76.61; H, 7.58; N, 4.37.

Example 12

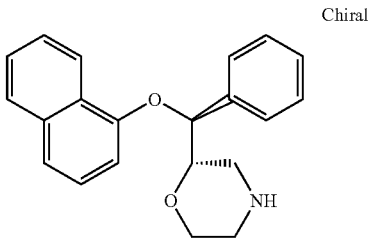

(S)-2-[(S)-(Naphthalen-1-yloxy)-phenyl-methyl]-morpholine was synthesized from naphthol according to general procedure A and was isolated as a gummy oil. MS (APCI): 320 [M+H]$^+$.

Example 13

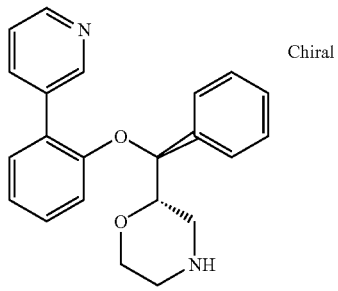

(S)-2-[(S)-Phenyl-(2-pyridin-3-yl-phenoxy)-methyl]-morpholine was synthesized from 6-[(2-Bromo-phenoxy)-phenyl-methyl]-morpholin-3-one and 4-pyridineboronic acid according to general procedures A and B and was isolated as a gummy oil. MS (APCI): 347 [M+H]$^+$.

Example 14

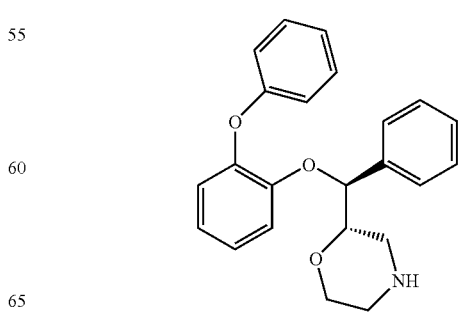

(S)-2-[(S)-(2-Phenoxy-phenoxy)-phenyl-methyl]-morpholine was synthesized from 2-phenoxy phenol according to general procedure A and was isolated as a gummy oil. MS (APCI): 362 [M+H]+.

Example 15

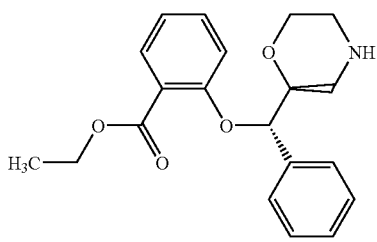

(2S,3S)-2-(Morpholin-2-yl-phenyl-methoxy)-benzoic acid ethyl ester was synthesized from 6-[(2-Bromo-phenoxy)-phenyl-methyl]-morpholin-3-one according to General Procedures A and F and was isolated as a gummy oil. MS (APCI): 342 [M+H]+.

Example 16

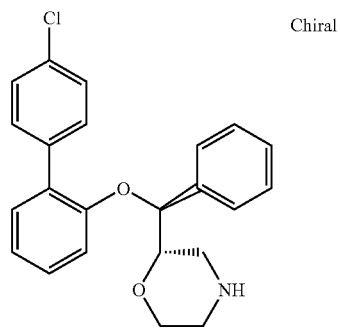

(S)-2-[((S)-4'-Chloro-biphenyl-2-yloxy)-phenyl-methyl]-morpholine was synthesized from 2-bromophenol according to general procedures A and B and was isolated as a gummy oil. MS (APCI): 381 [M+H]+.

Example 17

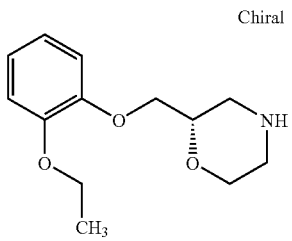

(S)-2-(2-Ethoxy-phenoxymethyl)-morpholine was synthesized from (S)-2-Hydroxymethyl-morpholine-4-carboxylic acid tert-butyl ester and 2-ethoxyphenol according to the following procedure:

Step 1. To a stirring mixture at room temperature of (S)-2-hydroxymethyl-morpholine-4-carboxylic acid, tert-butyl ester, 2-ethoxyphenol and triphenylphosphine in DME was added dropwise diisopropyl azodicarboxylate. The solution was stirred at room temperature for 24 h, concentrated (to remove most of the DME), then suspended into hexanes. The solid that formed was filtered. The filtrate was concentrated, redissolved into diethyl ether, then washed with 1 N NaOH (2×), sat. KH$_2$PO$_4$ and brine solutions. The organic extract was dried (MgSO$_4$), filtered, concentrated and chromatographed (MPLC, silica gel, 20% EtOAc in hexanes) to give (S)-2-(2-ethoxy-phenoxymethyl)-morpholine-4-carboxylic acid, tert-butyl ester as a colorless oil.

Step 2. (S)-2-(2-Ethoxy-phenoxymethyl)-morpholine fumarate. A solution of (S)-2-(2-ethoxy-phenoxymethyl)-morpholine-4-carboxylic acid, tert-butyl ester in CH$_2$Cl$_2$ was treated with trifluoroacetic acid. The solution was stirred at room temperature under N$_2$ for 2 h, concentrated then partitioned between CHCl$_3$ and 10% aq. NH$_4$OH solution. The organic extract was washed with brine, dried (MgSO$_4$), filtered and concentrated. The sample was converted to the fumaric acid salt in 2-propanol and precipitated from acetonitrile to give (S)-2-(2-ethoxy-phenoxymethyl)-morpholine fumarate as a white solid, mp 126-127° C. Analysis, calcd for C$_{13}$H$_{19}$NO$_3$xC$_4$H$_4$O$_4$ (353.375): C, 57.78; H, 6.56; N, 3.96. Found: C, 57.61; H, 6.50; N, 3.93.

Example 18

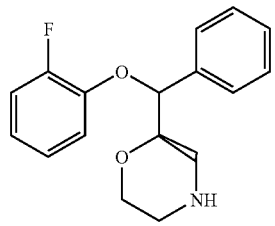

(R)-2-[(S)-(2-Fluoro-phenoxy)-phenyl-methyl]-morpholine was synthesized from 2-fluorophenol according to general procedure A and was isolated as a gummy oil. MS (APCI): 288 [M+H]+.

Example 19

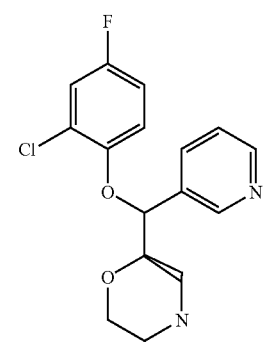

(S)-2-[(R)-(2-Chloro-4-fluoro-phenoxy)-pyridin-3-yl-methyl]-morpholine was synthesized from Morpholin-2-yl-pyridin-3-yl-methanol according to general procedure C and was isolated as a gummy foam. MS (APCI): 324 [M+H]+.

Example 20

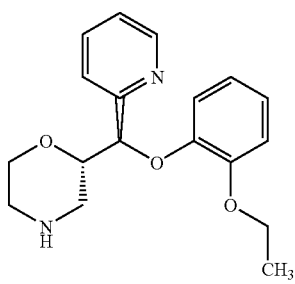

(S)-2-[(R)-(2-Ethoxy-phenoxy)-pyridin-2-yl-methyl]-morpholine was synthesized from (2-bromopyridine and 2-ethoxyphenol according to general procedure C and was isolated as a gummy oil. MS (APCI): 315 [M+H]$^+$.

Example 21

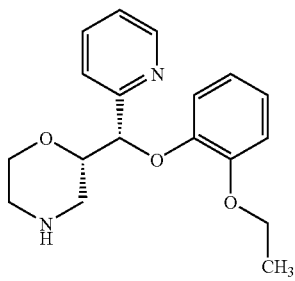

(S)-2-[(S)-(2-Ethoxy-phenoxy)-pyridin-2-yl-methyl]-morpholine was synthesized from (2-bromopyridine and 2-ethoxyphenol according to general procedure E and was isolated as the succinate salt. MS (APCI): 315 [M+H]$^+$.

Example 22

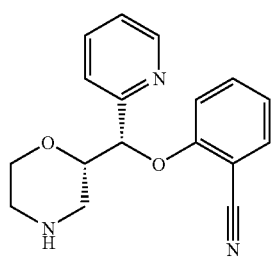

(2S,3R) and (2S,3S)-2-(Morpholin-2-yl-pyridin-2-yl-methoxy)-benzonitrile were independently synthesized from 2-bromopyridine and 2-cyanophenol according to general procedure C and were isolated as gummy oils which were shown by HNMR to be a mixture of diastereoisomers. Separation of these isomers afforded a gummy foam. MS (APCI): 296 [M+H]$^+$.

Example 23

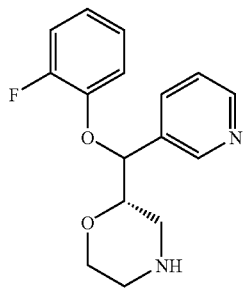

(S)-2-[(S)-(2-Fluorophenoxy)-pyridin-3-yl-methyl]-morpholine was synthesized via morpholin-2-yl-pyridin-3-yl-methanol from 3-bromopyridine and 2-fluorophenol according to general procedure C and was isolated as a gummy oil (mixture of diastereoisomers). MS (APCI): 289 [M+H]$^+$.

Example 24

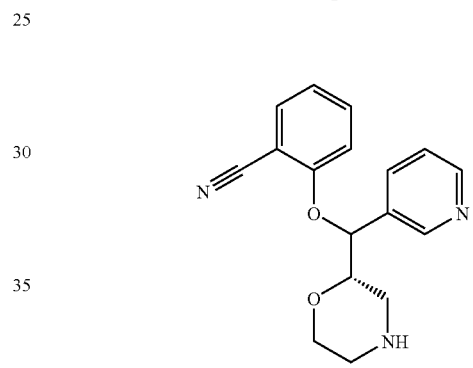

(2S,3R)-2-(Morpholin-2-yl-pyridin-3-yl-methoxy)-benzonitrile was synthesized via morpholin-2-yl-pyridin-3-yl-methanol from 3-bromopyridine and 2-cyanophenol according to general procedure C and was isolated as a gummy oil. MS (APCI): 296 [M+H]$^+$.

Example 25

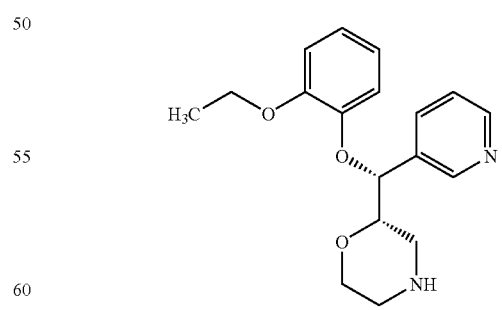

(2R,3R) and (2S,3R)-2-[(2-Ethoxy-phenoxy)-pyridin-3-yl-methyl]-morpholine were independently synthesized via morpholin-2-yl-pyridin-3-yl-methanol from 3-bromopyridine and 2-ethoxyphenol according to general procedure C and were isolated as oils. MS (APCI): 315 [M+H]$^+$.

Example 26

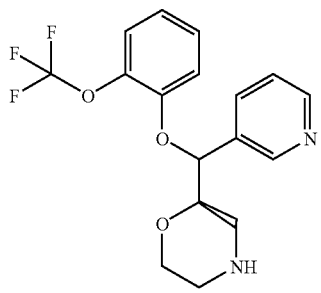

(R)-2-[(S)-Pyridin-3-yl-(2-trifluoromethoxy-phenoxy)-methyl]-morpholine was synthesized via morpholin-2-yl-pyridin-3-yl-methanol from 3-bromopyridine and 2-trifluoromethoxyphenol according to general procedure C and was isolated as a gummy oil. MS (APCI): 355 [M+H]$^+$.

Example 27

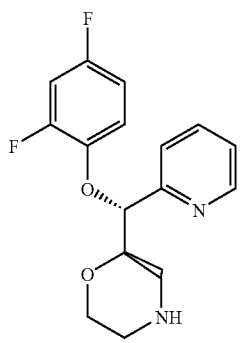

(R)-2-[(S)-(2-,4-Difluoro-phenoxy)-pyridin-3-yl-methyl]-morpholine was synthesized via morpholin-2-yl-pyridin-3-yl-methanol from 2-bromopyridine and 2,4-difluorophenol according to general procedure C and was isolated as a gummy oil. MS (APCI): 307 [M+H]$^+$.

Example 28

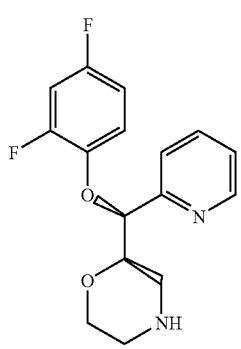

(R)-2-[(S)-(2-,4-Difluoro-phenoxy)-pyridin-3-yl-methyl]-morpholine was synthesized via morpholin-2-yl-pyridin-3-yl-methanol from 2-bromopyridine and 2,4-difluorophenol according to general procedure C and was isolated as a gummy oil. MS (APCI): 307 [M+H]$^+$.

Example 29

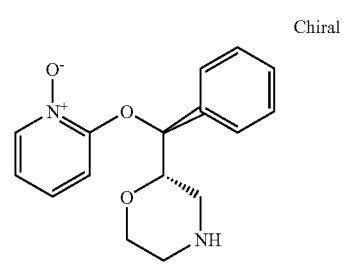

(S)-2-[((S)-1-Oxy-pyridin-2-yloxy)-phenyl-methyl]-morpholine was synthesized according to general procedure A and was isolated as pale yellow thick oil (0.095 g, 35%). $^1$H NMR (CD$_3$OD) δ: 7.55 (dd, 1H), 7.45-7.31 (m, 6H), 6.54 (dd, 1H), 6.07 (dt, 1H), 5.48 (d, 1H), 4.08 (m, 1H), 3.90 (td, 1H), 3.62 (m, 1H), 2.76 (m, 2H), 2.56 (dd, 1H), 2.41 (dd, 1H); MS (ES) 287.0 (Cl$_6$H$_{18}$N$_2$O$_3$+H)$^+$; HPLC purity (98%); CHN analysis calculated for C$_{16}$H$_{18}$N$_2$O$_3$: C, 66.65; H, 6.99; N, 9.72, Found: C, 66.67; H, 6.70; N, 9.32.

Example 30

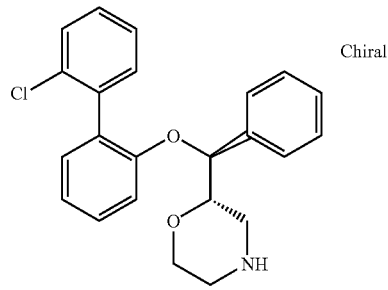

(S)-2-[(S)-(2'-Chloro-biphenyl-2-yloxy)-phenyl-methyl]-morpholine was from 2-bromophenol employing 2-chloroboronic acid in General Procedures A and B and was isolated as a thick viscous gum. $^1$H NMR (CDCl$_3$) δ: 7.48 (m, 1H), 7.40-7.10 (m, 10H), 6.96 (m, 1H), 6.80 (d, 1H), 5.04 (d, 1H), 3.84 (m, 1H), 3.64 (m, 1H), 3.50 (m, 1H), 2.68 (m, 2H), 2.42 (m, 1H), 2.30 (m, 1H). MS (ES) m/z 380.03 [C$_{23}$H$_{22}$ClNO$_2$+H]$^+$. Analysis: Calcd. C$_{23}$H$_2$ClNO$_2$: C, 72.72; H, 5.84; N, 3.69. Found: C, 72.41; H, 5.90; N, 3.80.

Example 31

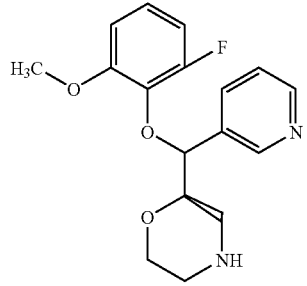

(2R,3R) and (R)-2-[(S)-(2-Fluoro-6-methoxy-phenoxy)-pyridin-3-yl-methyl]-morpholine were independently synthesized via morpholin-2-yl-pyridin-3-yl-methanol from 3-bromopyridine and 2-fluoro-6-methoxy phenol according to general procedure B with modification C and was isolated as a gummy oil. MS (APCI): 319 [M+H]⁺.

Example 32

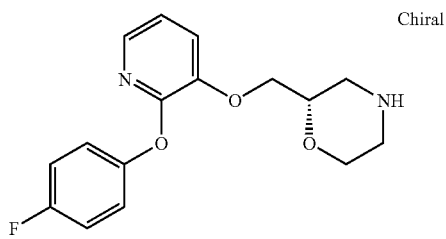

(S)-2-[2-(4-Fluoro-phenoxy)-pyridin-3-yloxymethyl]-morpholine was synthesized via General Procedure D and was isolated as a gummy oil. MS (APCI): 305 [M+H]⁺.

Example 33

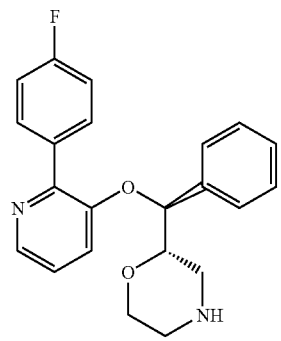

(S)-2-{(S)-[2-(4-Fluoro-phenyl)-pyridin-3-yloxy]-phenyl-methyl}-morpholine was synthesized according to the following scheme and procedure (which is a variation of General Procedures A and B):

Scheme G: Synthesis of pyridyl morpholine compounds.

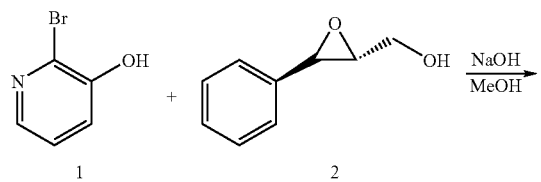

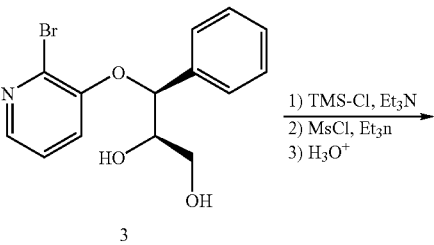

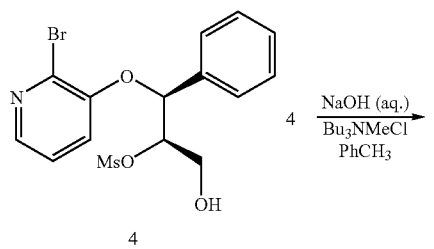

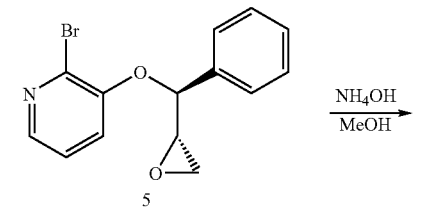

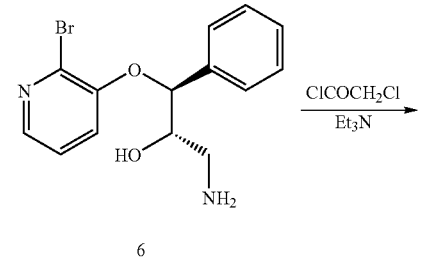

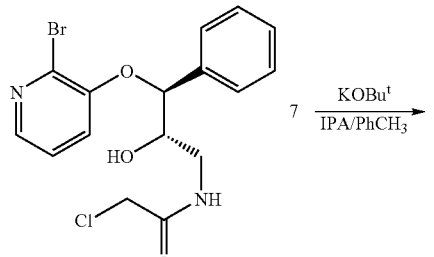

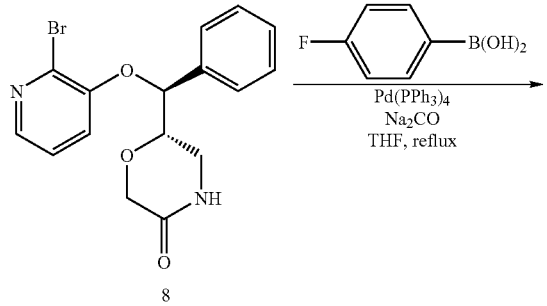

-continued

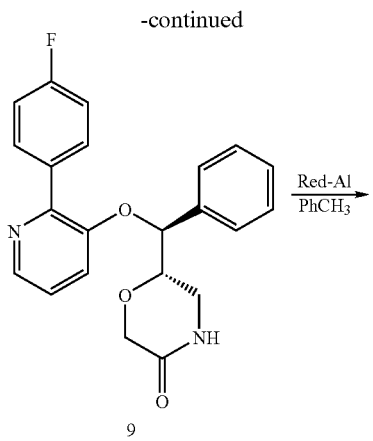

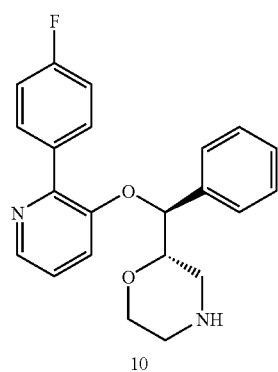

Preparation of Compound 3

A solution of 2-bromopyridinol 1 (7.6 g, 44 mmol) in 1N aqueous sodium hydroxide (44 mL, 44 mmol) was stirred at room temperature for 30 minutes. Phenylglycidol 2 (5.0 g, 33 mmol) was added in one portion and the reaction mixture was heated at 75° C. for 5 h. The reaction mixture was brought to room temperature and extracted with ethyl acetate. The combined organic extracts were dried over sodium sulphate, filtered and solvent was removed under reduced pressure. The reaction product was purified on silica gel (eluent 1:1 hexanes/ethyl acetate) to give the diol 3 (7.5 g, 69%) as a yellow oil. $^1$H NMR (400 MHz, CDCl$_3$) δ 7.90 (m, 1H), 7.36 (m, 5H), 7.00 (m, 1H), 6.92 (m, 1H), 5.32 (d, 1H), 4.00 (m, 2H), 3.84 (m, 1H), 2.94 (m, 1H), 2.60 (m, 1H).

Preparation of Compound 4

To a solution of diol 3 (5.0 g, 15.4 mmol) in ethyl acetate (120 mL) at 0° C. under nitrogen, was added triethylamine (3.2 mL, 23.0 mmol). Chlorotrimethylsilane (2.5 mL, 19.7 mmol) was added via syringe and the reaction mixture was allowed to warm to room temperature over 1 hour. TLC analysis showed no diol remaining. A further amount of triethylamine (3.2 mL, 23.0 mmol) was added followed by methanesulfonyl chloride (1.6 mL, 20.7 mmol). The reaction mixture was stirred at room temperature for 3 h, treated with 1N HCl, and stirred at room temperature for 2 hours. The aqueous phase was separated and extracted with ethyl acetate. The combined organic extracts were dried over sodium sulphate, filtered, and solvent was removed under reduced pressure to afford 3.5 g of mesylate 4 (56%) which was used without purification.

$^1$H NMR (400 MHz, CDCl$_3$) δ 7.96 (m, 1H), 7.40 (m, 5H), 7.04 (m, 1H), 6.94 (m, 1H), 5.58 (d, 1H), 5.00 (m, 1H), 4.24 (m, 1H), 4.04 (m, 1H), 2.76 (s, 3H).

Preparation of Compound 5

To a solution of compound 4 (5.5 g, 13.7 mmol) in toluene (25 mL) was added 1N sodium hydroxide (41 mL, 41 mmol) followed by tributylmethylammonium chloride (75 wt % in water, 0.5 mL). The reaction mixture was stirred at room temperature for 18 hours then was heated at 75° C. for 4 hours. TLC analysis showed no mesylate remaining. The reaction mixture was brought to room temperature and the layers were separated. The aqueous phase was extracted with toluene and the combined organic extracts were washed with brine, dried over sodium sulphate, filtered, and solvent was removed under reduced pressure. Chromatography of the product on a silica gel column (7:3 hexanes/ethyl acetate as eluent) gave 4.0 g of epoxide 5 (96%).

$^1$H NMR (400 MHz, CDCl$_3$) δ 7.96 (m, 1H), 7.40 (m, 5H), 7.06 (m, 2H), 4.92 (d, 1H), 3.50 (m, 1H), 2.88 (m, 1H), 2.82 (m, 1H).

Preparation of Compound 6

To a solution of concentrated ammonia (60 mL) in methanol (60 mL) was added a solution of compound 5 (4.0 g, 13.1 mmol) in methanol (50 mL) over 1 h. The reaction mixture was stirred at room temperature for 24 h. TLC analysis showed no starting material remaining. The reaction mixture was concentrated under reduced pressure and the residue was partitioned between water and ethyl acetate. The aqueous phase was separated and further extracted with ethyl acetate. The combined organic extracts were dried over sodium sulphate, filtered, and solvent was removed under reduced pressure to give 4.0 g (95%) of aminoalcohol 6 as a yellow oil which was carried on without purification.

$^1$H NMR (400 MHz, CDCl$_3$) δ 7.92 (m, 1H), 7.36 (m, 5H), 6.96 (m, 2H), 5.16 (d, 1H), 4.00 (m, 1H), 2.72 (m, 2H), 2.20 (br s, 3H).

Preparation of Compound 7

To a stirred solution of compound 6 (4.0 g, 12.4 mmol) in tetrahydrofuran (80 mL) under nitrogen, was added triethylamine (2.3 mL, 16.5 mmol). The reaction mixture was cooled to 0° C. Chloroacetyl chloride (1.2 mL, 15.1 mmol) was added dropwise and the reaction mixture was warmed to room temperature over 2 h. TLC analysis showed no starting material remaining. The reaction mixture was concentrated under reduced pressure and the residue was partitioned between saturated aqueous sodium bicarbonate and ethyl acetate. The organic phase was separated, washed with water, dried over sodium sulphate, and filtered. Removal of solvent under reduced pressure gave chloroacetamide 7 (4.4 g, 89%) as an off-white solid which was used without purification.

$^1$H NMR (400 MHz, CDCl$_3$) δ 7.96 (m, 1H), 7.40 (m, 5H), 7.24 (m, 1H), 6.90 (m, 1H), 5.04 (d, 1H), 4.20 (m, 1H), 4.04 (s, 2H), 3.44 (m, 2H).

Preparation of Compound 8

To a stirred solution of compound 7 (4.4 g, 11.0 mmol) in isopropyl alcohol/toluene (90 mL/30 mL) under nitrogen, was added a solution of potassium tert-butoxide (3.9 g, 33.0 mmol) in isopropyl alcohol (50 mL). The reaction mixture was stirred at room temperature for 18 hours at which point TLC analysis indicated the reaction was complete. The pH of the reaction mixture was adjusted to approximately 6.5 by the addition of 2N hydrochloric acid. The reaction mixture was concentrated under reduced pressure and the residue was partitioned between ethyl acetate and water. The aqueous phase was separated, basified by the addition of 2N NaOH, extracted with ethyl acetate and the combined organic extracts were dried over sodium sulphate, filtered, and solvent was removed under reduced pressure. The product was purified on a silica gel column (3:1 ethyl acetate/hexanes) to give morpholinone 8 (2.4 g, 60%) as a pale yellow solid.

$^1$H NMR (400 MHz, CDCl$_3$) δ 7.95 (m, 1H), 7.37 (m, 5H), 7.03 (m, 1H), 6.97 (m, 1H), 6.00 (br s, 1H), 5.30 (d, 1H), 4.32 (m, 2H), 4.26 (m, 1H), 3.37 (m, 1H), 3.13 (m, 1H).

Preparation of Compound 9

To a solution of compound 8 (0.526 g, 1.45 mmol) in tetrahydrofuran (10 mL) was added aqueous sodium carbonate (2M, 7 mL, 14 mmol), 4-fluorophenylboronic acid (0.683 g, 4.88 mmol), and tetrakistriphenylphosphine palladium (0) (0.093 g, 0.080 mmol). The dark reaction mixture was heated at 75-80° C. for 3 h. NMR check showed no starting material remaining. The reaction mixture was brought to room temperature, concentrated under reduced pressure, and the residue was partitioned between water and ethyl acetate. The aqueous phase was separated and further extracted with ethyl acetate, the combined organic extracts were dried over sodium sulphate, filtered and solvent was removed under reduced pressure. Initial chromatography of the reaction product gave 0.4 g of desired product as a foamy yellow solid. The product was further chromatographed on silica gel (eluent 1:1 dichloromethane/acetonitrile) to give 0.37 g of compound 9.

$^1$H NMR (400 MHz, CDCl$_3$) δ 8.26 (m, 1H), 7.96 (m, 2H), 7.32 (m, 5H), 7.12 (m, 3H), 7.04 (m, 1H), 5.96 (br s, 1H), 5.20 (d, 1H), 4.28 (m, 2H), 4.12 (m, 1H), 3.28 (m, 1H), 2.86 (m, 1H).

$^{19}$F NMR (376 MHz, CDCl$_3$) δ −113.770 (s, 1F)

Preparation of 10

A solution of compound 9 (0.95 g, 2.90 mmol) in anhydrous toluene (25 mL) was placed under a nitrogen atmosphere and cooled to 0° C. A commercial solution of Red-Al in toluene (65 wt %, 3.0 mL, 10.0 mmol) was added dropwise via syringe. The reaction mixture was warmed to room temperature over 1.5 h at which point TLC analysis indicated the presence of starting material. A further amount of Red-Al (0.3 mL, 1.0 mmol) was added and the reaction mixture was stirred for a further 1.5 h until the reaction was complete by TLC. The reaction mixture was again cooled to 0° C. and quenched by the dropwise addition of 2N sodium hydroxide. The mixture was diluted with water, and the aqueous phase was separated and extracted with toluene. The combined organic extracts were washed with brine, dried over sodium sulphate, filtered and solvent was removed under reduced pressure to give a 0.21 g of a cloudy oil. This oil was subjected to column chromatography (silica gel, eluent 4:1 ethyl acetate/methanol) to give 2-{[2-(4-Fluoro-phenyl)-pyridin-3-yloxy]-phenyl-methyl}-morpholine (10) (0.16 g, 66%) as a thick oil. $^1$H NMR (400 MHz, CDCl$_3$) δ 8.24 (m, 1H), 8.06 (m, 2H), 7.28 (m, 5H), 7.14 (m, 3H), 7.02 (m, 1H), 5.10 (d, 1H), 3.96 (m, 1H), 3.86 (m, 1H), 3.64 (m, 1H), 2.80 (m, 2H), 2.50 (m, 2H). $^{19}$F NMR (376 MHz, CDCl$_3$) 6-114.394 (m, 1F); (MS) m/z 364.97 [C$_{22}$H$_{21}$FN$_2$O$_2$+H$^+$]; CHN—C$_{22}$H$_{21}$FN$_2$O$_2$ Calc'd: C, 72.51%; H, 5.81%; N, 7.69%. Found: C, 72.39%; H, 6.07%; N, 8.04%.

Example 34

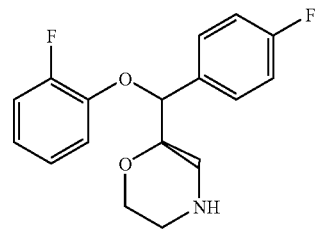

(R)-2-[(S)-(2-Fluoro-phenoxy)-(4-fluoro-phenyl)-methyl]-morpholine was synthesized from (3-fluorophenyl magnesium bromide and 2-fluorophenol according to general procedure C and was isolated as a gummy oil. MS (APCI): 306 [M+H]$^+$ Example 35

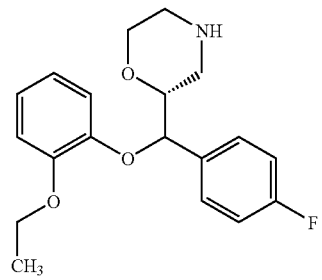

(R)-2-[(S)-(2-Fluoro-phenoxy)-(4-fluoro-phenyl)-methyl]-morpholine was synthesized from (4-fluorophenyl magnesium bromide and 2-ethoxyphenol according to general procedure C and was isolated as a gummy oil. MS (APCI): 332 [M+H]$^+$.

Example 36

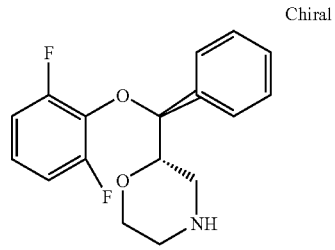

(S)-2-[(S)-(2,6-Difluoro-phenoxy)-phenyl-methyl]-morpholine was synthesized from 2,6-difluorophenol according to general procedure A and was isolated as a gummy oil. MS (APCI): 306 [M+H]$^+$.

Example 37

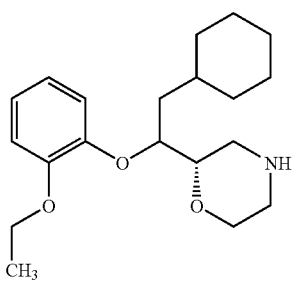

(S)-2-[(S)-2-Cyclohexyl-1-(2-ethoxy-phenoxy)-ethyl]-morpholine and (2S,3-R)-2-[2-Cyclohexyl-1-(2-ethoxy-phenoxy)-ethyl]-morpholine were synthesized from methylenecyclohexyl magnesium bromide according to general procedure C and was isolated as a gummy oil. MS (APCI): 334 [M+H]+.

Example 38

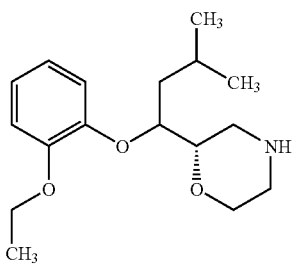

(S)-2-[(S)-1-(2-Ethoxy-phenoxy)-3-methyl-butyl]-morpholine was synthesized from isobutyl magnesium bromide according to general procedure C and was isolated as a gummy oil. MS (APCI): 294 [M+H]+.

Example 39

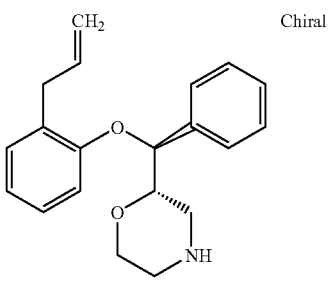

(S)-2-[(S)-(2-Allyl-phenoxy)-phenyl-methyl]-morpholine was synthesized 2-allylphenol according to General Procedures A and B and was isolated as a viscous colorless oil (0.415 g, 79%). $^1$H NMR (CDCl$_3$): δ 7.38-7.24 (m, 5H), 7.10 (dd, 1H), 6.98 (dt, 1H), 6.81 (dt, 1H), 6.65 (d, 1H), 6.04 (m, 1H), 5.18-5.04 (m, 3H), 3.98-3.86 (m, 2H), 3.65 (dt, 1H), 3.50 (m, 2H), 2.86-2.74 (m, 2H), 2.70-2.54 (m, 2H); MS (ES) 310.0 [C$_{20}$H$_{23}$NO$_2$+H]+; HPLC purity (98.2%); Analysis: Calcd. C$_{20}$H$_{23}$NO$_2$: C, 77.64; H, 7.49; N, 4.53. Found: C, 76.94; H, 7.48; N, 5.43.

Example 40

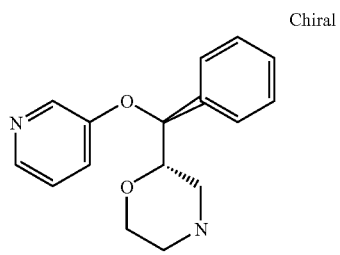

(S)-2-[(S)-Phenyl-(pyridin-3-yloxy)-methyl]-morpholine was synthesized from the corresponding amide (6-[Phenyl-(pyridin-3-yloxy)-methyl]-morpholin-3-one) (see Scheme G, compound 8) using the following procedure: A solution of compound 1 (0.30 g, 0.85 mmol) in anhydrous toluene (3.0 mL) was placed under a nitrogen atmosphere, cooled to 0° C. and a commercial solution of Red-Al (65 wt % in toluene, 1.0 mL, 3.3 mmol) was added dropwise via syringe. The reaction mixture was warmed to room temperature over 4 h. TLC analysis showed no starting material remaining. The reaction mixture was again cooled to 0° C. and quenched by the dropwise addition of 2N sodium hydroxide. The reaction mixture was diluted with toluene, the aqueous phase separated and further extracted with toluene. The combined organic extracts were dried over sodium sulphate, filtered, and solvent was removed under reduced pressure to give 0.30 g of light brown oil. Two chromatographies of the reaction product on silica gel (eluent—3:1 ethyl acetate/methanol the second) gave 0.080 g (35%) of the desired product. $^1$H NMR (400 MHz, CDCl$_3$) δ 8.32 (m, 1H), 8.12 (m, 1H), 7.24 (m, 5H), 7.10 (m, 2H), 5.10 (d, 1H), 3.96 (m, 2H), 3.68 (m, 1H), 2.84 (m, 2H), 2.66 (m, 2H), 1.84 (br s, 1H). (MS) m/z 271.05 [C$_{16}$H$_{18}$N$_2$O$_2$+H+]; CHN—C$_{16}$H$_{18}$N$_2$O$_2$ Calc'd: C, 71.09%; H, 6.71%; N, 10.36%. Found: C, 70.49%; H, 6.70%; N, 9.83%.

Example 41

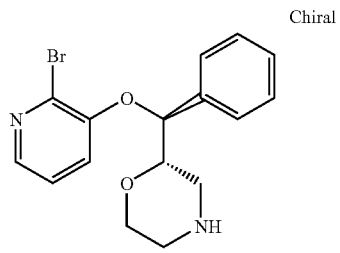

(S)-2-[(S)-(2-Bromo-pyridin-3-yloxy)-phenyl-methyl]-morpholine was synthesized from the corresponding amide (6-[Phenyl-(pyridin-3-yloxy)-methyl]-morpholin-3-one) using the following procedure: To a solution of compound 1 (0.4 g, 1.1 mmol) in anhydrous tetrahydrofuran (10 mL) under a nitrogen atmosphere was added a commercial solution of borane-tetrahydrofuran complex (1.0M in tetrahydrofuran, 3.4 mL, 3.4 mmol) via syringe. The reaction mixture was stirred at room temperature for 20 h. TLC analysis showed no reaction had occurred. A further amount of borane-tetrahydrofuran complex (3.0 mL, 3.0 mmol) was added and the reaction mixture was heated at reflux for 2.5 h. TLC analysis showed no starting material. The reaction mixture was brought to room temperature, treated with 1N HCl, stirred for 30 minutes, basified by the addition of 2N sodium hydroxide and extracted with ethyl acetate. The combined organic extracts were dried over sodium sulphate, filtered, and solvent was removed under reduced pressure. Two chromatographies of the reaction product on silica gel (eluent—3:1 ethyl acetate/methanol for first chromatography, 10:1 dichloromethane/methanol for the second) gave 0.063 g (16%) of the desired product. $^1$H NMR (400 MHz, CDCl$_3$) δ 7.90 (m, 1H), 7.36 (m, 5H), 7.00 (m, 2H), 5.16 (d, 1H), 3.96 (m, 2H), 3.68 (m, 1H), 2.82 (m, 2H), 2.64 (m, 2H), 1.80 (br s, 1H). (MS) m/z 350.92 [Cl$_6$H$_{17}$BrN$_2$O$_2$+H$^+$] HPLC—91.49% CHN—C$_{22}$H$_{21}$FN$_2$O$_2$ Calc'd: C, 55.03%; H, 4.91%; N, 8.02%. Found: C, 55.01%; H, 4.97%; N, 8.60%.

Example 42

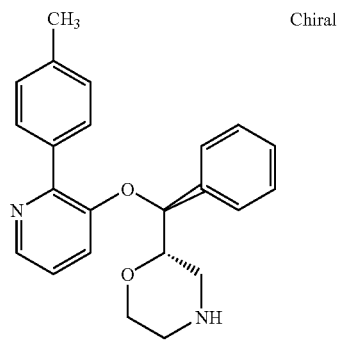

(S)-2-[(S)-Phenyl-(2-p-tolyl-pyridin-3-yloxy)-methyl]-morpholine was synthesized from the corresponding amide (6-[Phenyl-(pyridin-3-yloxy)-methyl]-morpholin-3-one) using General Procedure B (employing 4-methylphenylboronic acid in the coupling step) and gave 0.20 g of light brown oil. Two chromatographies of the reaction product on silica gel (eluent—3:1 ethyl acetate/methanol) gave 0.080 g (35%) of the desired product. $^1$H NMR (400 MHz, CDCl$_3$) δ 8.24 (m, 1H), 7.96 (d, 2H), 7.27 (m, 7H), 7.07 (m, 1H), 6.98 (m, 1H), 5.13 (d, 1H), 3.96 (m, 1H), 3.87 (m, 1H), 3.64 (m, 1H), 2.80 (m, 2H), 2.53 (m, 2H), 2.44 (s, 3H). (MS) m/z 361.07 [C$_{23}$H$_{24}$N$_2$O$_2$+H$^+$].

Example 43

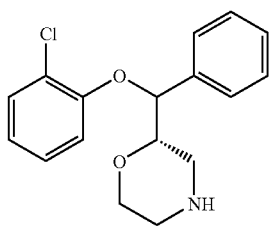

(S)-2-[(S)-(2-Chloro-phenoxy)-phenyl-methyl]-morpholine was synthesized 2-chlorophenol according to general procedure A and was isolated as a gummy oil. MS (APCI): 305 [M+H]$^+$.

Example 44

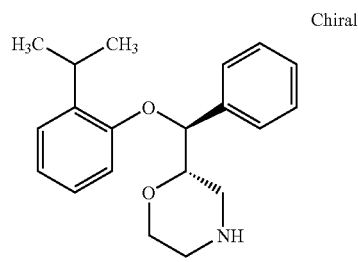

(S)-2-[(S)-(2-Isopropyl-phenoxy)-phenyl-methyl]-morpholine was synthesized 2-isopropylphenol according to general procedure A and was isolated as a gummy oil. $^1$H NMR (CDCl$_3$) δ: 7.40-7.30 (m, 5H), 7.19 (d, 1H), 6.90 (m, 1H), 6.82 (m, 1H), 6.70 (d, 1H), 5.13 (d, 1H), 3.90 (m, 2H), 3.70 (m, 1H), 3.50 (m, 1H), 2.80 (m, 2H), 2.75 (m, 1H), 2.60 (m, 1H), 1.70 (b s, 1H), 1.32 (d, 3H), 1.30 (d, 3H). MS (ES) m/z 312.06 [C$_{20}$H$_{25}$NO$_2$+H]$^+$. Analysis: Calcd for C$_{20}$H$_{25}$NO$_2$: C, 77.14; H, 8.09; N, 4.50. Found: C, 75.62; H, 8.47; N, 5.09.

Example 45

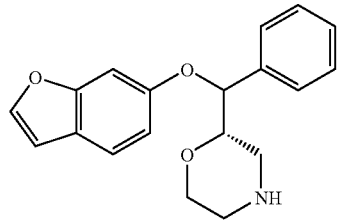

(R)-2-[(S)-(Benzofuran-6-yloxy)-phenyl-methyl]-morpholine was synthesized from 2-(Hydroxy-phenyl-methyl)-morpholine-4-carboxylic acid tert-butyl ester and 6-hydroxybenzofuran according General Procedure C employing the alternate etherification sequence (via the mesylate) and was isolated as an oil. MS (APCI): 310 [M+H]$^+$.

Example 46

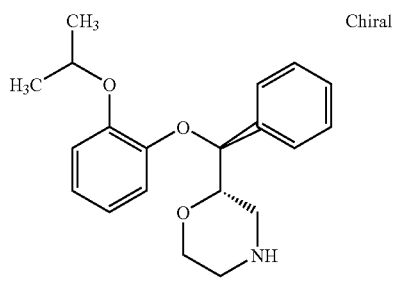

(S)-2-[(S)-(2-Isopropoxy-phenoxy)-phenyl-methyl]-morpholine was synthesized from 2-isopropoxy phenol according to general procedure A and was isolated as a gummy oil. MS (APCI): 328 [M+H]$^+$.

Example 47

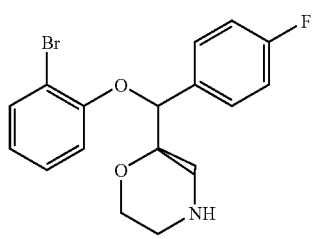

(R)-2-[(S)-(2-Bromo-phenoxy)-(4-fluoro-phenyl)-methyl]-morpholine was synthesized from 4-fluorophenol magnesium bromide and bromophenol according to general procedure C and was isolated as a gummy oil. MS (APCI): 367 [M+H]$^+$.

Example 48

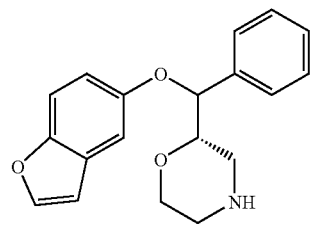

(S)-2-[(S)-(Benzofuran-5-yloxy)-phenyl-methyl]-morpholine was synthesized according General Procedure C employing the alternate etherification sequence (via the mesylate) and was isolated as an oil. MS (APCI): 310 [M+H]$^+$.

Example 49

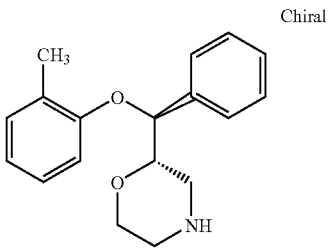

(S)-2-((S)-Phenyl-o-tolyloxy-methyl)-morpholine was synthesized from 2-methyl phenol according to general procedure A and was isolated as a gummy oil. MS (APCI): 284 [M+H]$^+$.

Example 50

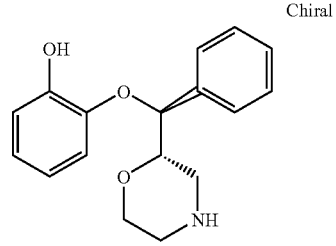

(2S,3S)-2-(Morpholin-2-yl-phenyl-methoxy)-phenol was synthesized from 2-benzyloxy phenol according to general procedure A with the following modification:

Scheme:

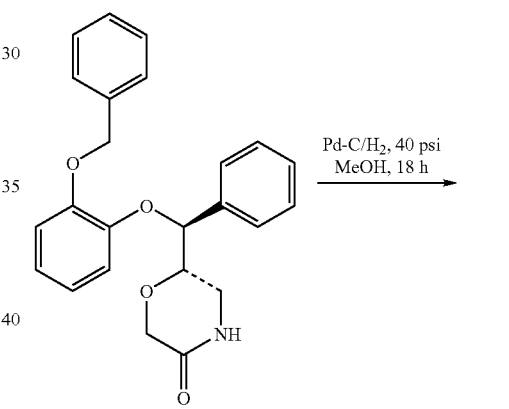

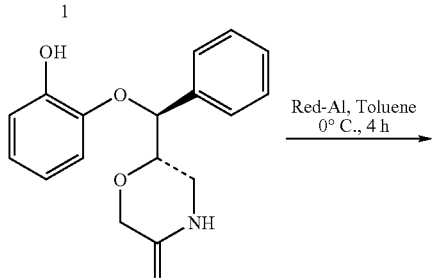

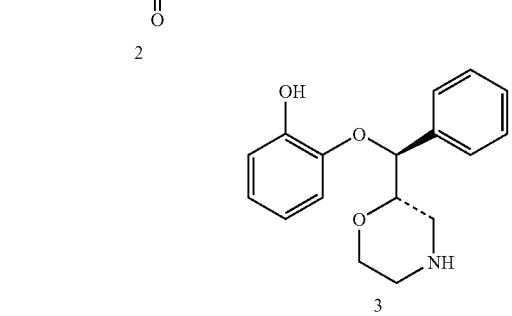

Experimental:

Step 1: Preparation of Compound 2

A mixture of 1 (0.61 g, 1.568 mmol) and 10% Pd—C (0.22 g) in methanol: tetrahydrofuran (50 mL:20 mL) was shaken under a hydrogen atmosphere (40 psi) for 18 hours. The mixture was filtered through a celite column and concentrated under reduced pressure to give phenol 2 as a thick viscous gum (Yield: 0.224 g, 47.8%). $^1$H NMR (CDCl$_3$) δ 7.58 (b s, 1H), 7.41-7.35 (m, 5H), 7.08 (b s, 1H), 6.90 (m, 2H), 6.59 (m, 1H), 6.50 (m, 1H), 4.65 (d, 1H), 4.45 (d, 1H), 4.30 (d, 1H), 4.18 (m, 1H), 3.20 (m, 1H), 2.75 (d, 1H). MS (ES) m/z 300.09 [Cl$_7$H$_{17}$NO$_4$+H]$^+$.

Step 2: Preparation of Compound 3

To a solution of morpholinone 2 (0.214 g, 0.750 mmol) in toluene (10 mL), Red-Al (65% solution in toluene, 1.5 mL) was added dropwise at 0° C. The reaction mixture was stirred at ice temperature for 4 h. Excess Red-Al was destroyed by dropwise addition of 2M NaOH solution (5 mL) and acidified to pH 2 with 6N HCl. The solution was neutralized with saturated NaHCO$_3$ and extracted with toluene (2×10 mL). The combined organic extract was washed with brine and dried over anhydrous Na$_2$SO$_4$. The solvent was removed under reduced pressure and the product was purified on a column of silica gel (ethyl acetate: methanol, 80:20) to give morpholine compound 3 as a colorless solid (Yield: 0.062 g, 31%), mp 156-158° C. $^1$H NMR (CDCl$_3$) δ: 7.45-7.38 (m, 5H), 6.97 (m, 2H), 6.58 (m, 1H), 6.50 (d, 1H), 4.53 (d, 1H), 4.10 (m, 1H), 3.95 (m, 1H), 3.90 (m, 1H), 2.90 (m, 2H), 2.50 (m, 1H), 2.42 (m, 1H). MS (ES) m/z 285.98 [C$_{17}$H$_{19}$NO$_3$+H]$^+$. Analysis: Calcd for C$_{17}$H$_{19}$NO$_3$ (0.5H$_2$O) C, 69.37; H, 6.85; N, 4.76. Found: C, 69.68; H, 5.45; N, 4.44.

Example 51

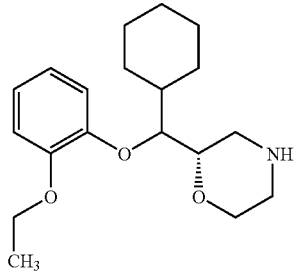

(S)-2-[(S)-Cyclohexyl-(2-ethoxy-phenoxy)-methyl]-morpholine was synthesized from cyclohexylmagnesium bromide and 2-ethoxy phenol according to general procedure C and was isolated as a gummy oil. MS (APCI): 320 [M+H]$^+$.

Example 52

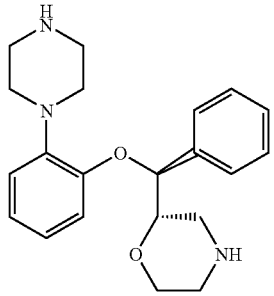

(S)-2-[(S)-Phenyl-(2-piperazin-1-yl-phenoxy)-methyl]-morpholine was synthesized according to general procedures A and B and was isolated as a gummy oil. MS (APCI): 354 [M+H]$^+$.

Example 53

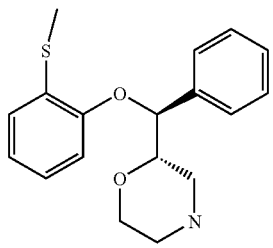

(S)-2-[(S)-(2-Methylsulfanyl-phenoxy)-phenyl-methyl]-morpholine was synthesized from 2-Methanesulfanyl phenol according to general procedure A and was isolated as a gummy oil. MS (APCI): 314 [M+H]$^+$.

Example 54

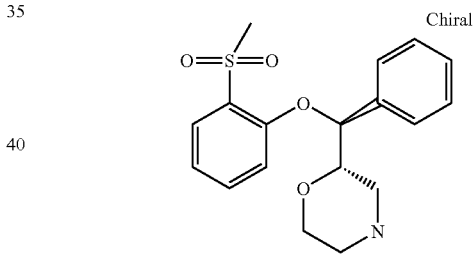

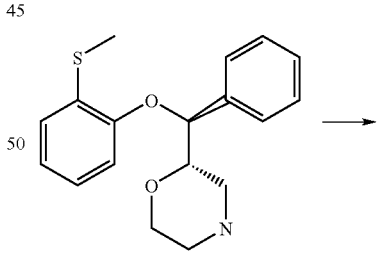

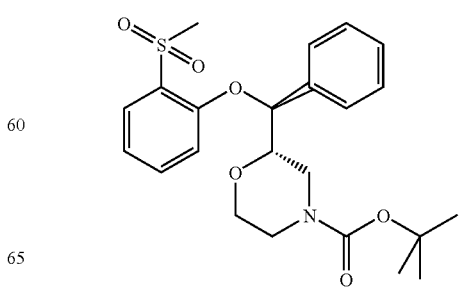

-continued

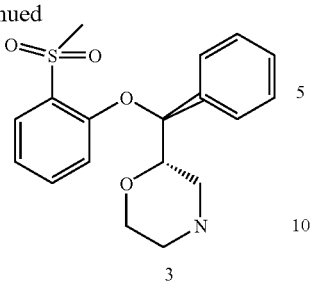

(S)-2-[(S)-(2-Methanesulfonyl-phenoxy)-phenyl-methyl]-morpholine was synthesized from 2-[(2-Methanelsulfanyl-phenoxy)-phenyl-methyl]-morpholine according to the following procedure:

Step 1: The starting amine (250 mg, 0.85 mmol) was dissolved in THF (5 mL) with NaOH (1 M aq., 1.0 mL). To this stirred solution was added BOC2O (220 mg, 0.98 mmol) and the reaction mixture was stirred for 1 hour. The reaction was quench with water (30 mL) and extracted into 1:1 hexane:EtOAc (2×20 mL). The combined organics were washed with brine (40 mL), dried over $Na_2SO_4$, and concentrated to dryness. The material is clean except for some BOC20 which is still present.

Step 2: The starting alcohol (270 mg, 0.65 mmol) was dissolved in chloroform (3.2 mL) and mcpba (290 mg, 1.6 mmol) was added as a solution in chloroform (4.0 mL) at 0 C. After stirring for 4 hours, the reaction was filtered through cotton in a pipette and extracted with 5% aq. $NaHCO_3$ (2×110 mL). After concentration, NMR analysis of the crude shows clean conversion to a single product. This was purified on silica (25-70% EtOAc/hexanes) to give the product as a colorless foam.

Step 3: The starting material was dissolved in 4 M HCl (solution in dioxane) at 0 C. The reaction mixture was stirred for 1 h. When starting material was consumed (by TLC, 1 h), the reaction was concentrated to dryness and taken up in MeOH (with 5% HOAc). Purification on ion exchange (SCX, 1 g, loading in 5% HOAc./MeOH, washing with MeOH, eluting with 1 M $NH_3$ in MeOH) gave a colorless sticky oil which was determined to contain a single isomer by NMR. Optical rotation of this sample (41 mg/ mL in MeOH, 100 mm path length, −3.713 degrees Arc) was −90 degrees and HPLC analysis of the sample indicated >98% purity. MS (APCI): 330 [M+H]$^+$.

Example 55

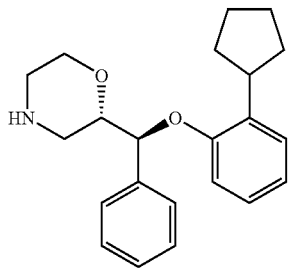

(S)-2-[(S)-(2-Cyclopentyl-phenoxy)-phenyl-methyl]-morpholine was synthesized according to general procedure A and was isolated as a gummy solid. MS (APCI): 338 [M+H]$^+$.

Example 56

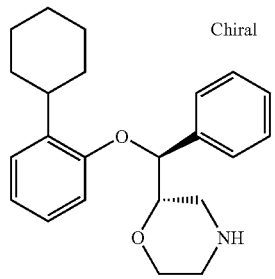

(S)-2-[(S)-(2-Cyclohexyl-phenoxy)-phenyl-methyl]-morpholine was synthesized according to general procedure A and was isolated as an oil. MS (APCI): 352 [M+H]$^+$.

Example 57

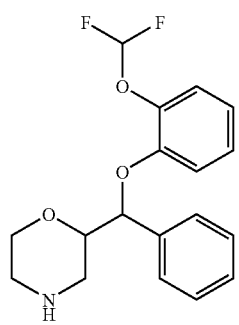

(S)-2-[(S)-(2-Difluoromethoxy-phenoxy)-phenyl-methyl]-morpholine was synthesized according to general procedure A and was isolated as an oil. MS (APCI): 336 [M+H]$^+$.

Example 58

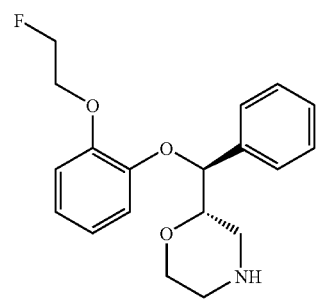

(S)-2-{(S)-[2-(2-Fluoro-ethoxy)-phenoxy]-phenyl-methyl}-morpholine was synthesized according to General Procedure A and was isolated as a gummy solid. MS (APCI): 332 [M+H]⁺.

Example 59

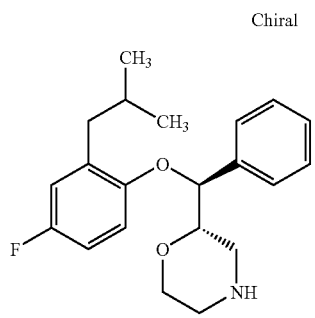

(S)-2-[(S)-(4-Fluoro-2-isobutyl-phenoxy)-phenyl-methyl]-morpholine was synthesized according to General Procedure A and was isolated as a gummy solid. MS (APCI): 344 [M+H]⁺.

Example 60

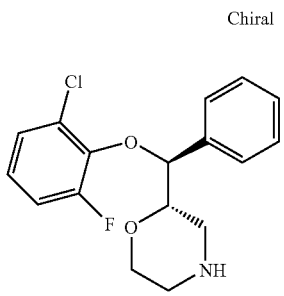

(S)-2-[(S)-(2-Chloro-6-fluoro-phenyl-methyl]-morpholine was synthesized according to General Procedure A and was isolated as a gummy solid. MS (APCI): 322 [M+H]⁺.

Example 61

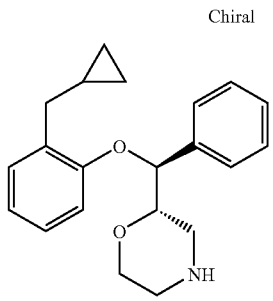

(S)-2-[(S)-(2-Cyclopropylmethyl-phenoxy)-phenyl-methyl]-morpholine was synthesized according to General Procedure A and was isolated as a gummy solid. MS (APCI): 324 [M+H]⁺.

Example 62

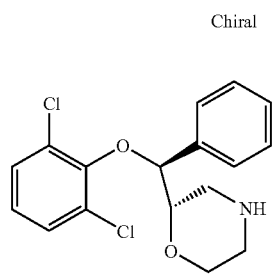

(S)-2-[(S)-(2,6-Dichloro-phenoxy)-phenyl-methyl]-morpholine was synthesized according to General Procedure A and was isolated as a gummy solid. MS (APCI): 339 [M+H]⁺.

Example 63

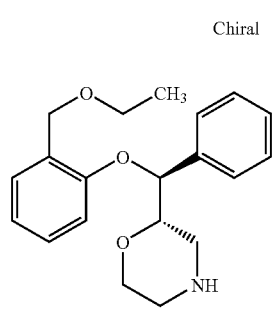

(S)-2-[(S)-(2-Ethoxymethyl-phenoxy)-phenyl-methyl]-morpholine was synthesized from [2-(Morpholin-2-yl-phenyl-methoxy)-phenyl]-methanol according to General Procedures A and F and was isolated as a gummy solid. MS (APCI): 328 [M+H]⁺.

Example 64

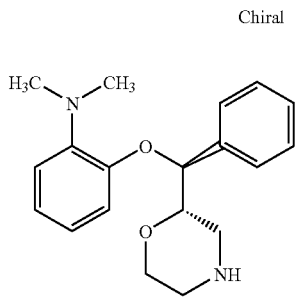

(2S,3S)-Dimethyl-[2-(morpholin-2-yl-phenyl-methoxy)-phenyl]-amine was synthesized according to General Procedure A and was isolated as a gummy solid. MS (APCI): 313 [M+H]⁺.

Example 65

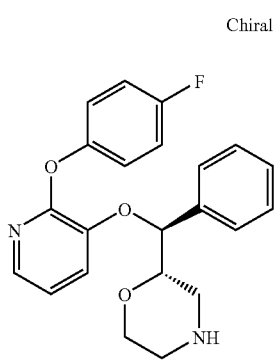

(S)-2-{(S)-[2-(4-Fluoro-phenoxy)-pyridin-3-yloxy]-phenyl-methyl}-morpholine was synthesized from (S)-2-[(S)-(2-Bromo-pyridin-3-yloxy)-phenyl-methyl]-morpholine according to General Procedure A and the biaryl coupling reaction of General Procedure D and was isolated as a gummy solid. MS (APCI): 381 [M+H]⁺.

Example 66

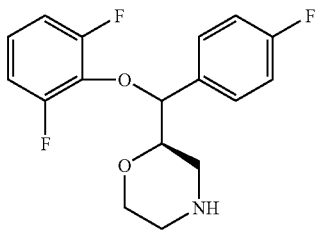

(R)-2-[(S)-(2,6-Difluoro-phenoxy)-(4-fluoro-phenyl)-methyl]-morpholine was synthesized according to General Procedure C and was isolated as its fumarate salt (white solid). MS (APCI): 324 [M+H]⁺.

Example 67

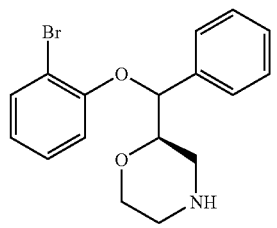

(R)-2-[(S)-(2-Bromo-phenoxy)-phenyl-methyl]-morpholine was synthesized according to General Procedure C and was isolated as the fumarate salt (white solid). MS (APCI): 348 [M+H]⁺.

Example 68

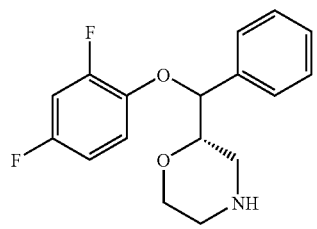

(S)-2-[(S)-(2,4-Difluoro-phenoxy)-phenyl-methyl]-morpholine was synthesized according to General Procedure C and was isolated as the fumarate salt (white solid). MS (APCI): 306 [M+H]⁺.

Example 69

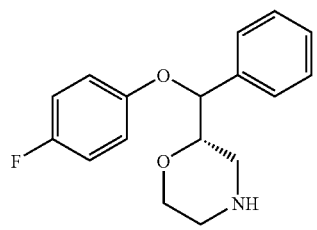

(S)-2-[(S)-(4-Fluoro-phenoxy)-phenyl-methyl]-morpholine was synthesized according to General Procedure C and was isolated as the fumarate salt (white solid). MS (APCI): 288 [M+H]⁺.

Example 70

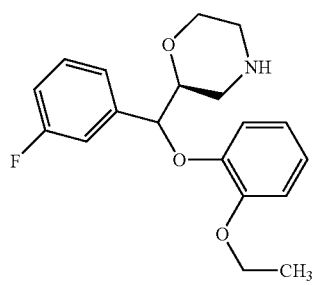

(R)-2-[(S)-(2-Ethoxy-phenoxy)-(3-fluoro-phenyl)-methyl]-morpholine was synthesized according to General Procedure C and was isolated as the fumarate salt (white solid). MS (APCI): 332 [M+H]$^+$.

Example 71

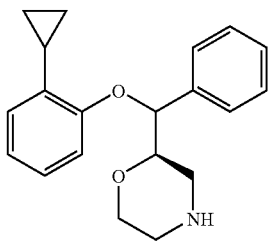

(R)-2-[(S)-(2-Cyclopropyl-phenoxy)-phenyl-methyl]-morpholine was synthesized according to General Procedure C and was isolated as the fumarate salt (white solid). MS (APCI): 310 [M+H]$^+$.

Example 72

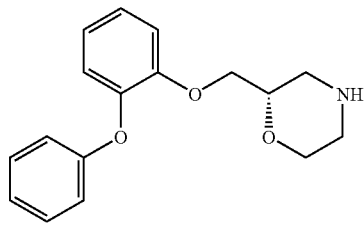

(S)-2-(2-Phenoxy-phenoxymethyl)-morpholine was prepared according to General Procedure D and was isolated as the hydrochloride salt MS (APCI): 310 [M+H]+.

Example 73

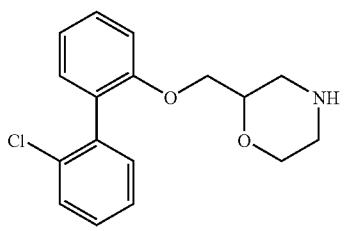

2-(2'-Chloro-biphenyl-2-yloxymethyl)-morpholine was prepared by the biphenyl version of General Procedure D and was isolated as the hydrochloride salt MS (APCI): 304 [M+H]$^+$.

Example 74

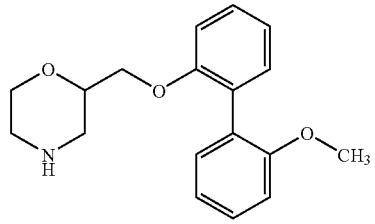

2-(2'-Methoxy-biphenyl-2-yloxymethyl)-morpholine was prepared by the biphenyl version of General Procedure D and was isolated as the fumarate salt MS (APCI): 300 [M+H]$^+$.

Example 75

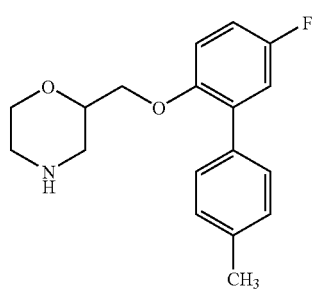

(R)- and (S)-2-(5-Fluoro-4'-methyl-biphenyl-2-yloxymethyl)-morpholine were independently prepared from the (R) and (S) morpholine alcohols by the biphenyl version of General Procedure D and was isolated as the fumarate salt MS (APCI): 302 [M+H]$^+$.

Example 76

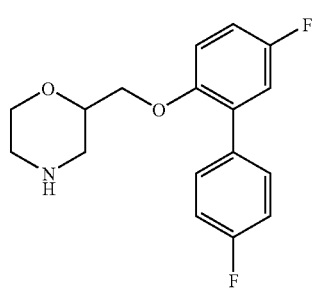

(R)- and (S)-2-(5,4'-Difluoro-biphenyl-2-yloxymethyl)-morpholine were independently prepared from the (R) and (S) morpholine alcohols by the biphenyl version of General Procedure D and was isolated as the fumarate salt MS (APCI): 306 [M+H]$^+$.

Example 77

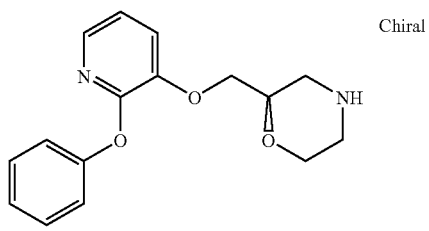

(R)-2-(2-Phenoxy-pyridin-3-yloxymethyl)-morpholine was prepared by the biaryl ether version of General Procedure D and was isolated as the fumarate salt MS (APCI): 287 [M+H]$^+$.

Example 78

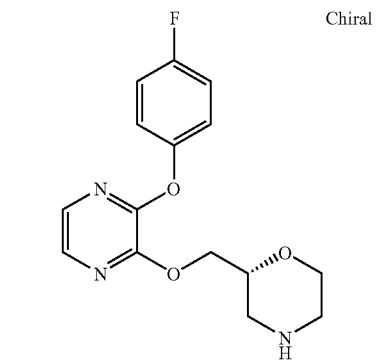

(S)-2-[3-(4-Fluoro-phenoxy)-pyrazin-2-yloxymethyl]-morpholine was prepared by using General Procedure D starting from 2,3-dichloropyrazine and was isolated as the hydrochloride salt MS (APCI): 287 [M+H]$^+$.

Example 79

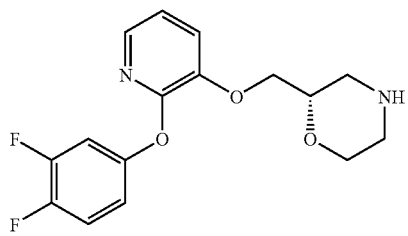

(S)-2-[2-(3,4-Difluoro-phenoxy)-pyridin-3-yloxymethyl]-morpholine was prepared by the biaryl ether version of General Procedure D and was isolated as the fumarate salt MS (APCI): 323 [M+H]$^+$.

Example 80

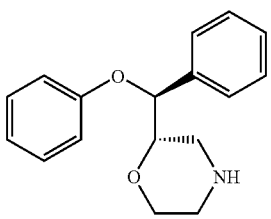

(S)-2-((S)-Phenoxy-phenyl-methyl)-morpholine was synthesized according to General Procedure A and was isolated as an oil. MS (APCI): 270 [M+H]$^+$.

Example 81

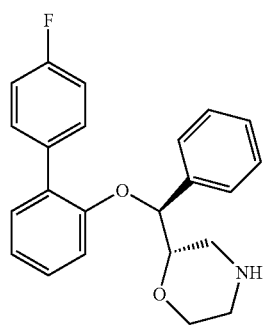

(S)-2-[(S)-(4'-Fluoro-biphenyl-2-yloxy)-phenyl-methyl]-morpholine was synthesized according to General Procedures A and B and was isolated as an oil. MS (APCI): 364 [M+H]$^+$.

Example 82

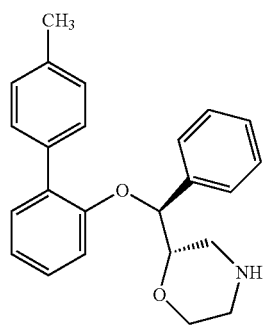

(S)-2-[(S)-(4'-Methyl-biphenyl-2-yloxy)-phenyl-methyl]-morpholine was synthesized according to General Procedures A and B and was isolated as an oil. MS (APCI): 360 [M+H]⁺.

Example 83

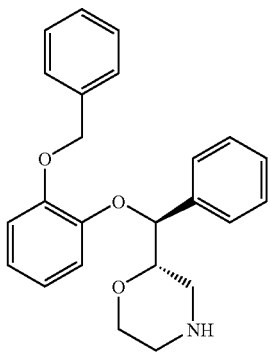

(S)-2-[(S)-(2-Benzyloxy-phenoxy)-phenyl-methyl]-morpholine was synthesized according to General Procedure A and was isolated as an oil. MS (APCI): 376 [M+H]⁺.

Example 84

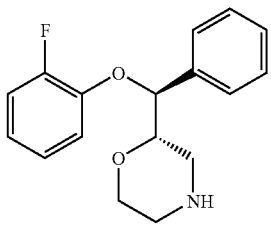

(S)-2-[(S)-(2-Fluoro-phenoxy)-phenyl-methyl]-morpholine was synthesized according to General Procedure A and was isolated as an oil. MS (APCI): 288 [M+H]⁺.

Example 85

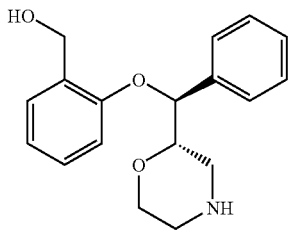

(2S,3S)-[2-(Morpholin-2-yl-phenyl-methoxy)-phenyl]-methanol was synthesized according to General Procedures A and F and was isolated a pale yellow oil. MS (APCI): 300 [M+H]⁺.

Example 86

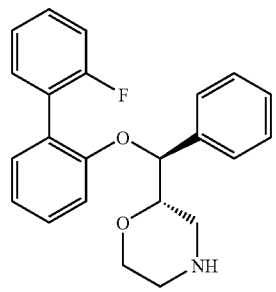

(S)-2-[(S)-(2'-Fluoro-biphenyl-2-yloxy)-phenyl-methyl]-morpholine was synthesized according to General Procedures A and B and was isolated as an oil. MS (APCI): 364 [M+H]⁺.

Example 87

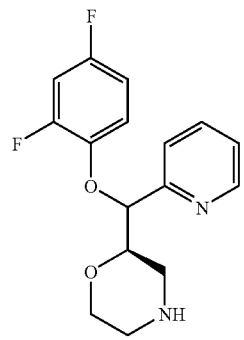

(2R,3R)-2-[(2,4-Difluoro-phenoxy)-pyridin-2-yl-methyl]-morpholine was synthesized according to General Procedure C and was isolated as a white solid. MS (APCI): 307 [M+H]⁺.

Example 88

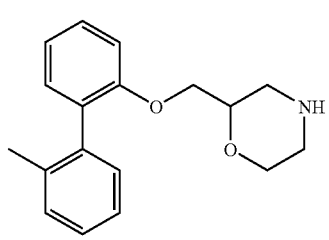

2-(2'-Methyl-biphenyl-2-yloxymethyl)-morpholine (racemic) was synthesized according to General Procedure D (biphenyl version) and was isolated as the hydrochloride salt. MS (APCI): 284 [M+H]+.

Example 89

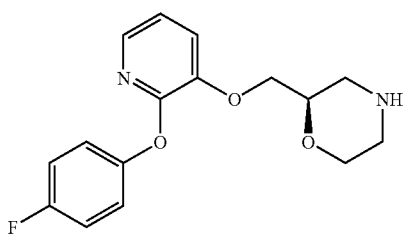

(2R)-2-[2-(4-Fluoro-phenoxy)-pyridin-3-yloxymethyl]-morpholine was synthesized according to General Procedure D and was isolated as the fumarate salt. MS (APCI): 305 [M+H]+.

Example 90

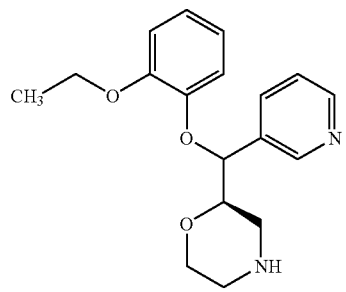

(2R)-2-[(R)-(2-Ethoxy-phenoxy)-pyridin-3-yl-methyl]-morpholine was synthesized according to General Procedure C and was isolated as a white foam. MS (APCI): 315 [M+H]+.

Example 91

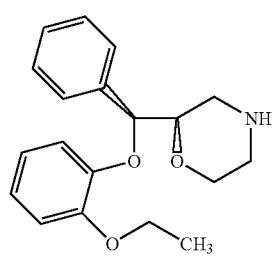

(R)-2-[(S)-(2-Ethoxy-phenoxy)-phenyl-methyl]-morpholine was prepared according to General Procedure C and was isolated as an foam. MS (APCI): 314 [M+H]+.

Example 92

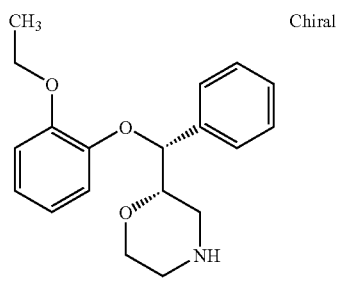

(S)-2-[(R)-(2-Ethoxy-phenoxy)-phenyl-methyl]-morpholine was prepared according to General Procedure C and was isolated as an foam. MS (APCI): 314 [M+H]+.

Example 93

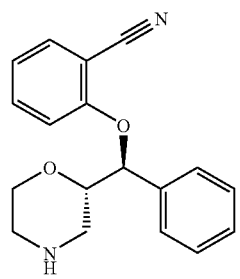

2-[(S)-(2S)-morpholin-2-yl(phenyl)methoxy]benzonitrile was synthesized according to General Procedure C and was isolated as a white solid. MS (APCI): 294 [M+H]+.

Example 94

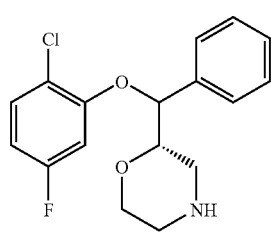

(2S)-2-[(2-chloro-5-fluorophenoxy)(phenyl)methyl]morpholine was prepared according to General Procedure C and was isolated as the fumarate salt. MS (APCI): 321 [M+H]⁺.

Example 95

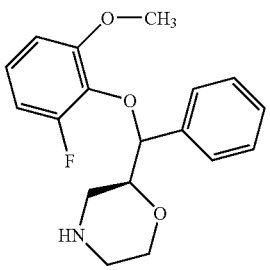

(2S)-2-[(2-fluoro-6-methoxyphenoxy)(phenyl)methyl]morpholine was prepared according to General Procedure C and was isolated as the fumarate salt. MS (APCI): 317 [M+H]⁺.

Example 96

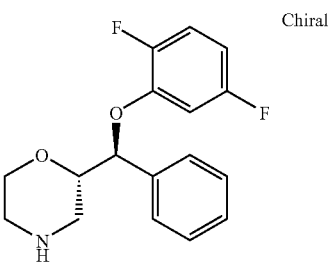

(2S)-2-[(S)-(2,5-difluorophenoxy)(phenyl)methyl]morpholine was prepared according to General Procedure C and was isolated as the fumarate salt. MS (APCI): 305 [M+H]⁺.

Example 97

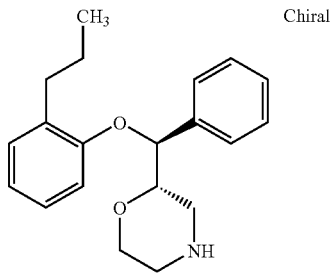

(2S)-2-[(S)-phenyl(2-propylphenoxy)methyl]morpholine was prepared according to General Procedure A and was isolated as the fumarate salt. MS (APCI): 311 [M+H]⁺.

Example 98

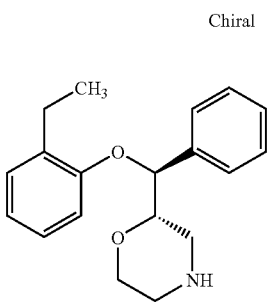

(2S)-2-[(S)-(2-ethylphenoxy)(phenyl)methyl]morpholine was prepared according to General Procedure A and was isolated as the fumarate salt. MS (APCI): 297 [M+H]⁺.

Example 99

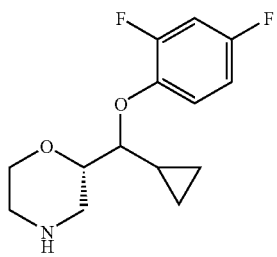

(2S)-2-[cyclopropyl(2,4-difluorophenoxy)methyl]morpholine was prepared according to General Procedure C and was isolated a gum (mixture of diastereoisomers). MS (APCI): 269 [M+H]⁺.

Example 100

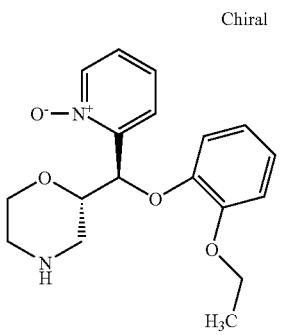

(2S)-2-[(S)-(2-ethoxyphenoxy)(1-oxidopyridin-2-yl)methyl]morpholine was prepared according to General Procedure C with the following additional step: The starting amine was dissolved in DCM along with MTO and aq H₂O₂ was added. This was stirred at r.t. for 79 hours and was quenched by cautious addition (vigorous gas evolution, exotheric, use a very small amount of MnO$_2$) of MnO$_2$ and this bubbling mixture was vigorously stirred for 3 hours until gas evolution ceased. The phases were separated and the aq. phase extracted with CH$_2$Cl$_2$ (2×). The combined organic phases were concentrated to afford clean product. MS (APCI): 331 [M+H]$^+$.

Example 101

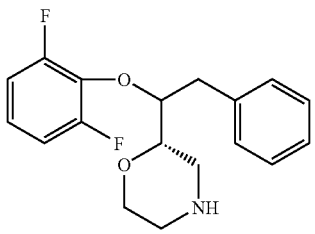

(2S)-2-[1-(2,6-difluorophenoxy)-2-phenylethyl]morpholine was prepared according to General Procedure E and was isolated a gum (mixture of diastereoisomers). MS (APCI): 319 [M+H]$^+$.

Example 102

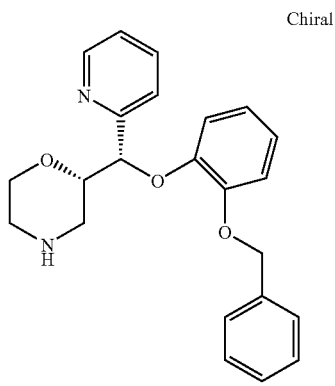

(2S)-2-[(S)-[2-(benzyloxy)phenoxy](pyridin-2-yl)methyl]morpholine was prepared according to General Procedure C and was isolated as the fumarate salt. MS (APCI): 376 [M+H]$^+$.

Example 103

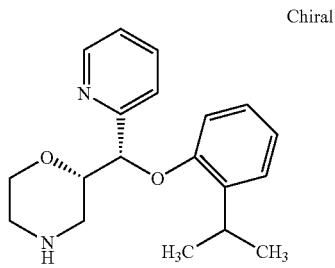

(2S)-2-[(S)-(2-isopropylphenoxy)(pyridin-2-yl)methyl]morpholine was prepared according to General Procedure E and was isolated as the fumarate salt. MS (APCI): 312 [M+H]$^+$.

Example 104

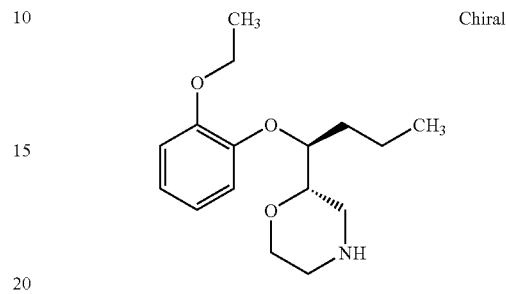

(2S)-2-[(1S)-1-(2-ethoxyphenoxy)butyl]morpholine was prepared according to General Procedure E and was isolated as the fumarate salt (mixture of diastereoisomers). MS (APCI): 279 [M+H]$^+$.

Example 105

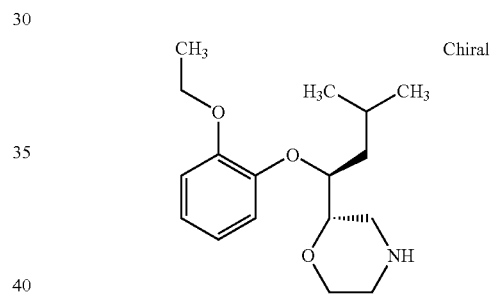

(2S)-2-[(1S)-1-(2-ethoxyphenoxy)-3-methylbutyl]morpholine was prepared according to General Procedure C and was isolated as the fumarate salt (mixture of diastereoisomers). MS (APCI): 293 [M+H]$^+$.

Example 106

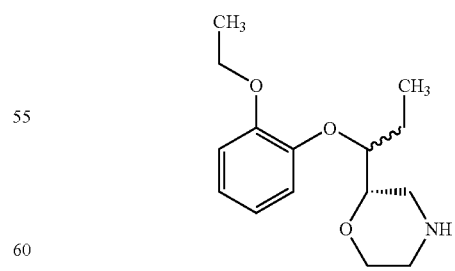

(2S)-2-[(S)-(2,3-difluorophenoxy)(3-fluorophenyl)methyl]morpholine and (2S)-2-[(R)-(2,3-difluorophenoxy)(3-fluorophenyl)methyl]morpholine were prepared according to General Procedure C and was isolated as a mixture of diastereoisomers. MS (APCI): 266 [M+H]$^+$.

Example 107

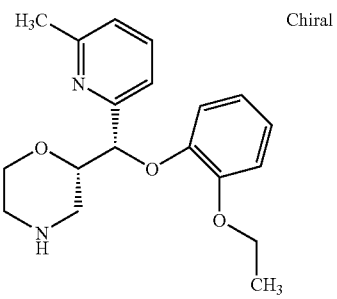

(2S)-2-[(S)-(2-ethoxyphenoxy)(6-methylpyridin-2-yl)methyl]morpholine was prepared according to General Procedure E and was isolated as the fumarate salt. MS (APCI): 328 [M+H]+.

Example 108

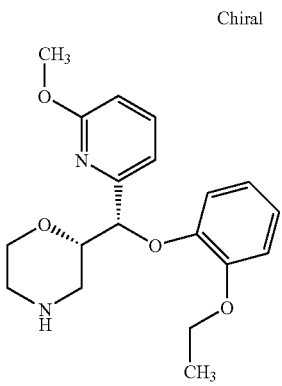

(2S)-2-[(S)-(2-ethoxyphenoxy)(6-methoxypyridin-2-yl)methyl]morpholine was prepared according to General Procedure E and was isolated as the fumarate salt. MS (APCI): 344 [M+H]+.

Example 109

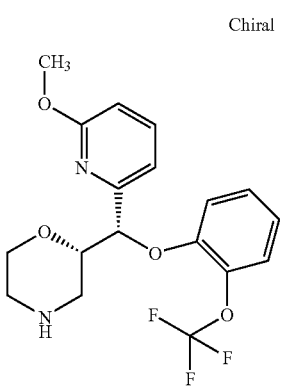

(2S)-2-{(S)-(6-methoxypyridin-2-yl)[2-(trifluoromethoxy)phenoxy]methyl}morpholine was prepared according to General Procedure E and was isolated as the fumarate salt. MS (APCI): 384 [M+H]+.

Example 110

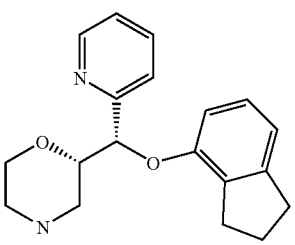

(2S)-2-[(S)-(2,3-dihydro-1H-inden-4-yloxy)(pyridin-2-yl)methyl]morpholine was prepared according to General Procedure E and was isolated as the succinate salt. MS (APCI): 311 [M+H]+.

Example 111

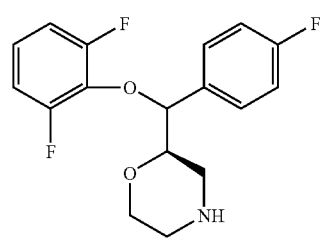

(2R)-2-[(2,6-difluorophenoxy)(4-fluorophenyl)methyl]morpholine was synthesized according to General Procedure C and was isolated as a white solid. MS (APCI): 323 [M+H]+.

Example 112

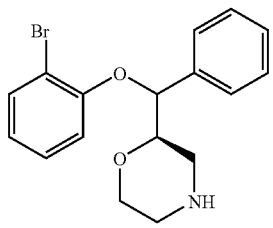

(2R)-2-[(2-bromophenoxy)(phenyl)methyl]morpholine was synthesized according to General Procedure C and was isolated as a white solid. MS (APCI): 349 [M+H]+.

Example 113

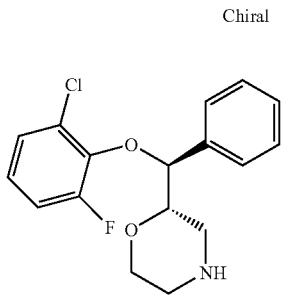

(2S)-2-[(S)-(2-chloro-6-fluorophenoxy)(phenyl)methyl]morpholine was synthesized according to General Procedure C and was isolated as a white solid. MS (APCI): 322 [M+H]+.

Example 114

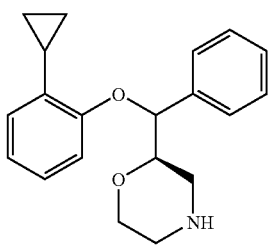

(2R)-2-[(2-cyclopropylphenoxy)(phenyl)methyl]morpholine was synthesized according to General Procedure E and was isolated as a white solid. MS (APCI): 310 [M+H]+.

Example 115

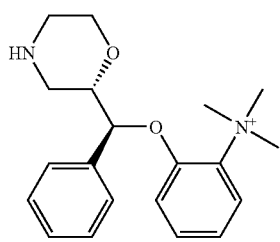

N,N,N-trimethyl-2-[(S)-(2S)-morpholin-2-yl(phenyl)methoxy]benzenaminium was synthesized according to General Procedure A and was isolated as a white solid. MS (APCI): 328 [M+H]+.

Example 116

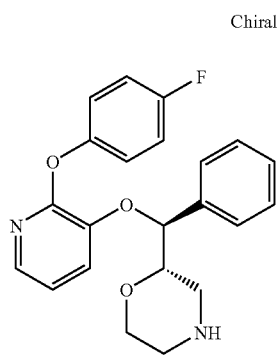

(2S)-2-[(S)-{[2-(4-fluorophenoxy)pyridin-3-yl]oxy}(phenyl)methyl]morpholine was synthesized according to General Procedure A and was isolated as a white solid. MS (APCI): 381 [M+H]+.

Example 117

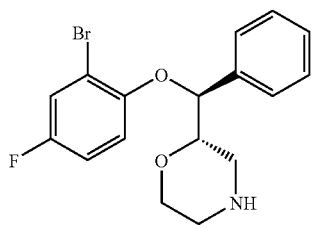

(2S)-2-[(S)-(2-bromo-4-fluorophenoxy)(phenyl)methyl]morpholine was synthesized according to General Procedure A and was isolated as a white solid. MS (APCI): 367 [M+H]+.

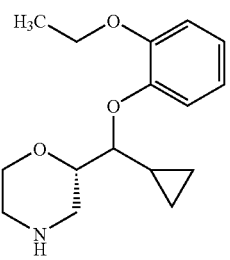

Example 118

(2S)-2-[cyclopropyl(2-ethoxyphenoxy)methyl]morpholine was synthesized according to General Procedure C and was isolated as a white solid. MS (APCI): 278 [M+H]+.

Example 119

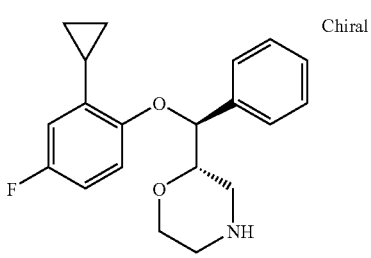

(2S)-2-[(S)-(2-cyclopropyl-4-fluorophenoxy)(phenyl)methyl]morpholine was synthesized according to General Procedures A and B and was isolated as a white solid. MS (APCI): 328 [M+H]⁺.

Example 120

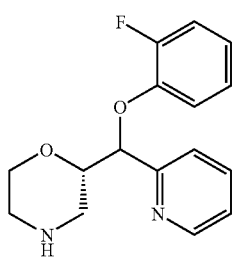

(2S)-2-[(S)-[2-fluorophenoxy)](pyridin-2-yl)methyl]morpholine was synthesized according to General Procedure C and was isolated as a white solid. MS (APCI): 289 [M+H]⁺.

Example 121

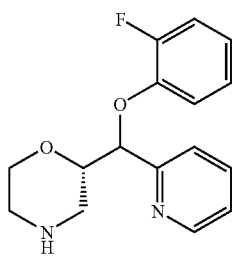

(2S)-2-[(R)-[2-fluorophenoxy)](pyridin-2-yl)methyl]morpholine was synthesized according to General Procedure C and was isolated as a white solid. MS (APCI): 289 [M+H]⁺.

Example 122

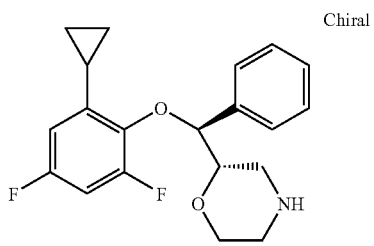

(2S)-2-[(S)-(2-cyclopropyl-4,6-difluorophenoxy)(phenyl)methyl]morpholine was synthesized according to General Procedures A and B and was isolated as a white solid. MS (APCI): 346 [M+H]⁺.

Example 123

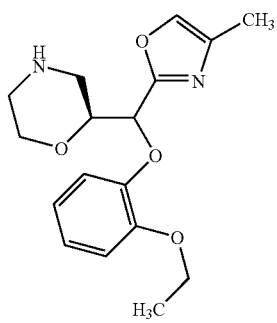

(2S)-2-[(2-ethoxyphenoxy)(4-methyl-1,3-oxazol-2-yl)methyl]morpholine was synthesized according to General Procedure E and was isolated as a white solid. MS (APCI): 319 [M+H]⁺.

Example 124

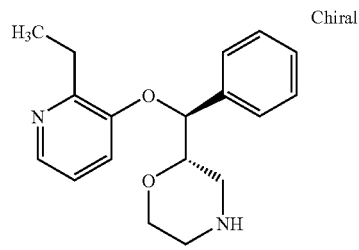

(2S)-2-[(S)-[(2-ethylpyridin-3-yl)oxy](phenyl)methyl]morpholine was synthesized according to General Procedure A and was isolated as a white solid. MS (APCI): 299 [M+H]⁺.

Example 125

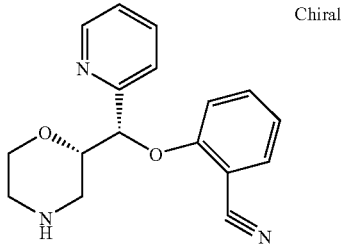

2-[(S)-(2S)-morpholin-2-yl(pyridin-2-yl)methoxy]benzonitrile was synthesized according to General Procedure C and was isolated as a white solid. MS (APCI): 296 [M+H]⁺.

Example 126

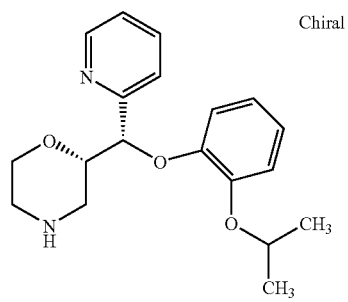

(2S)-2-[(S)-(2-isopropoxyphenoxy)(pyridin-2-yl)methyl]morpholine was synthesized according to General Procedure E and was isolated as a white solid. MS (APCI): 329 [M+H]⁺.

Example 127

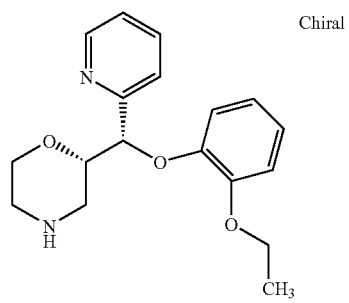

(2S)-2-[(S)-(2-propylphenoxy)(pyridin-2-yl)methyl]morpholine was synthesized according to General Procedure E and was isolated as a white solid. MS (APCI): 313 [M+H]⁺.

Example 128

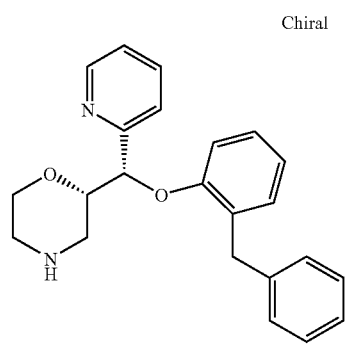

(2S)-2-[(S)-(2-benzylphenoxy)(pyridin-2-yl)methyl]morpholine was synthesized according to General Procedure E and was isolated as a white solid. MS (APCI): 361 [M+H]⁺.

Example 129

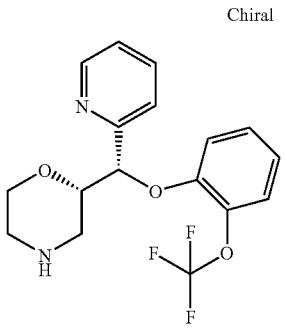

(2S)-2-{(S)-pyridin-2-yl[2-(trifluoromethoxy)phenoxy]methyl}morpholine was synthesized according to General Procedure E and was isolated as a white solid. MS (APCI): 355 [M+H]⁺.

Example 130

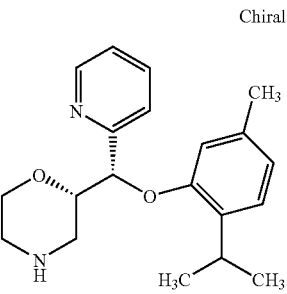

(2S)-2-[(S)-(2-isopropyl-5-methylphenoxy)(pyridin-2-yl)methyl]morpholine was synthesized according to General Procedure E and was isolated as a white solid. MS (APCI): 327 [M+H]⁺.

Example 131

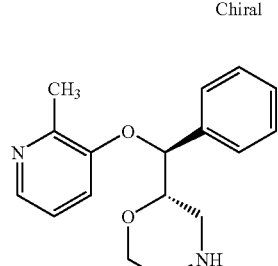

(2S)-2-[(S)-[(2-methylpyridin-3-yl)oxy](phenyl)methyl]morpholine was synthesized according to General Procedure A and was isolated as a white solid. MS (APCI): 285 [M+H]⁺.

Example 132

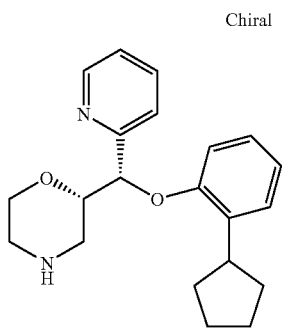

(2S)-2-[(S)-(2-cyclopentylphenoxy)(pyridin-2-yl)methyl]morpholine was synthesized according to General Procedure E and was isolated as a white solid. MS (APCI): 339 [M+H]⁺.

Example 133

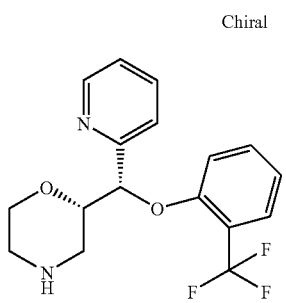

(2S)-2-{(S)-pyridin-2-yl[2-(trifluoromethyl)phenoxy]methyl}morpholine was synthesized according to General Procedure E and was isolated as a white solid. MS (APCI): 339 [M+H]⁺.

Example 134

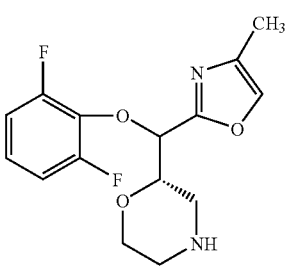

(2S)-2-[(2,6-difluorophenoxy)(4-methyl-1,3-oxazol-2-yl)methyl]morpholine was synthesized according to General Procedure E and was isolated as a the fumarate salt (mixture of diastereoisomers). MS (APCI): 311 [M+H]⁺.

Example 135

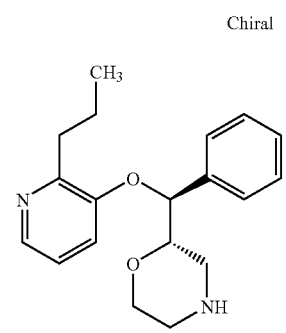

(2S)-2-{(S)-phenyl[(2-propylpyridin-3-yl)oxy]methyl}morpholine was synthesized according to General Procedure A and was isolated as a white solid. MS (APCI): 313 [M+H]⁺.

Example 136

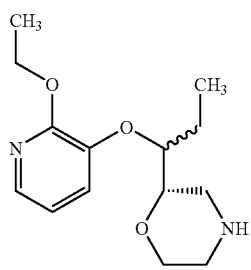

(2S)-2-{1-[(2-ethoxypyridin-3-yl)oxy]propyl}morpholine was synthesized according to General Procedure C and was isolated as a gummy oil containing a mixture of diastereoisomers. MS (APCI): 267 [M+H]⁺.

Example 137

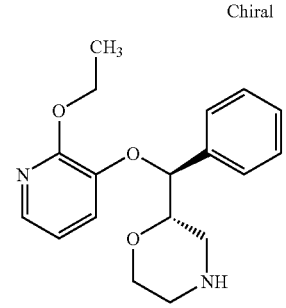

(2S)-2-[(S)-[(2-ethoxypyridin-3-yl)oxy](phenyl)methyl]morpholine was synthesized according to General Procedure A and was isolated as a white solid. MS (APCI): 315 [M+H]⁺.

Example 138

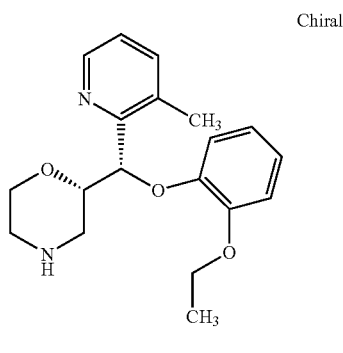

(2S)-2-[(S)-(2-ethoxyphenoxy)(3-methylpyridin-2-yl)methyl]morpholine was synthesized according to General Procedure E and was isolated as a white solid. MS (APCI): 329 [M+H]⁺.

Example 139

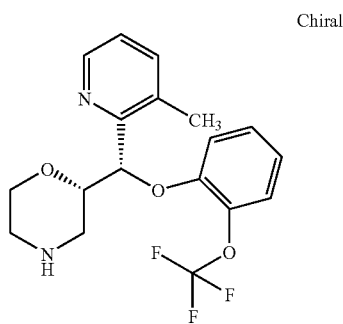

(2S)-2-{(S)-(3-methylpyridin-2-yl)[2-(trifluoromethoxy)phenoxy]methyl}morpholine was synthesized according to General Procedure E and was isolated as a white solid. MS (APCI): 369 [M+H]⁺.

Example 140

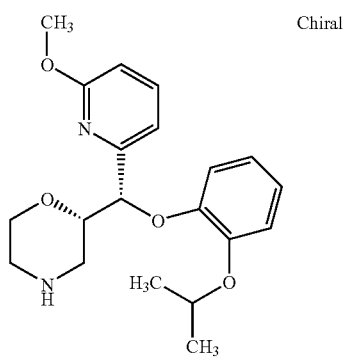

(2S)-2-[(S)-(2-isopropoxyphenoxy)(6-methoxypyridin-2-yl)methyl]morpholine was synthesized according to General Procedure E and was isolated as a white solid. MS (APCI): 359 [M+H]⁺.

Example 141

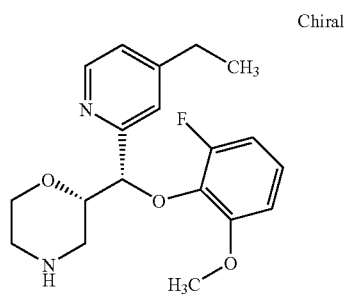

(2S)-2-[(S)-(4-ethylpyridin-2-yl) (2-fluoro-6-methoxyphenoxy)methyl]morpholine was synthesized according to General Procedure E and was isolated as a white solid. MS (APCI): 347 [M+H]⁺.

Example 142

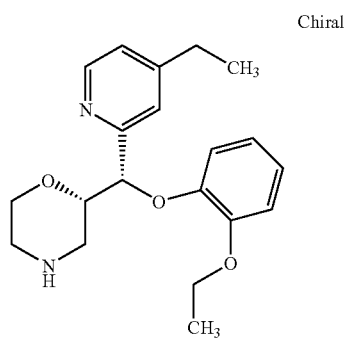

(2S)-2-[(S)-(2-ethoxyphenoxy)(4-ethylpyridin-2-yl)methyl]morpholine was synthesized according to General Procedure E and was isolated as a white solid. MS (APCI): 343 [M+H]⁺.

Example 143

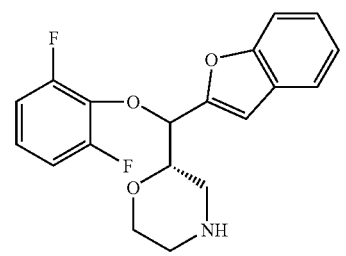

(2S)-2-[1-benzofuran-2-yl(2,6-difluorophenoxy)methyl]morpholine was synthesized according to General Procedure C and was isolated as a white solid containing a mixture of diastereoisomers. MS (APCI): 346 [M+H]⁺.

Example 144

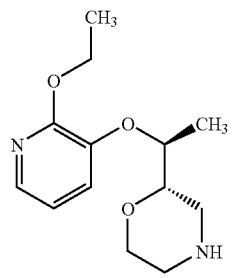

(2S)-2-{(1S)-1-[(2-ethoxypyridin-3-yl)oxy]ethyl}morpholine was synthesized according to General Procedure C and was isolated as a white solid. MS (APCI): 253 [M+H]⁺.

Example 145

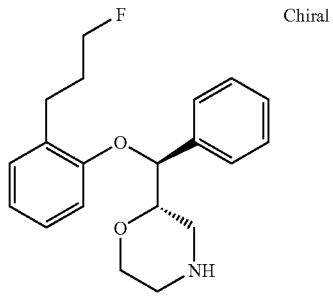

(2S)-2-[(S)-[2-(3-fluoropropyl)phenoxy](phenyl)methyl]morpholine was synthesized according to General Procedure A and was isolated as a white solid. MS (APCI): 330 [M+H]⁺.

Example 146

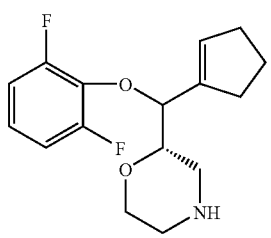

(2S)-2-[(S)-cyclopent-1-en-1-yl(2,6-difluorophenoxy)methyl]morpholine was synthesized according to General Procedure C and was isolated as a white solid containing a mixture of diastereoisomers. MS (APCI): 296 [M+H]⁺.

Example 147

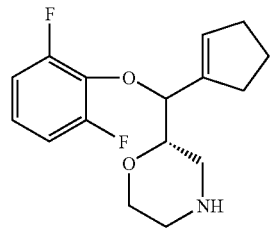

(2S)-2-[(R)-cyclopent-1-en-1-yl(2,6-difluorophenoxy)methyl]morpholine was synthesized according to General Procedure C and was isolated as a white solid. MS (APCI): 296 [M+H]⁺.

Example 148

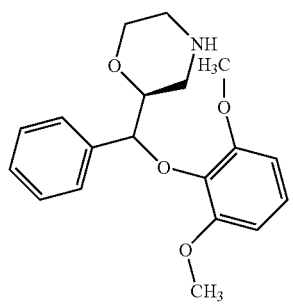

(2S)-2-[(2,6-dimethoxyphenoxy)(phenyl)methyl]morpholine was synthesized according to General Procedure C and was isolated as a white solid. MS (APCI): 330 [M+H]⁺.

Example 149

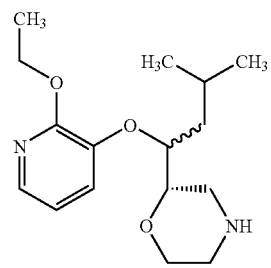

(2S)-2-{1-[(2-ethoxypyridin-3-yl)oxy]-3-methylbutyl}morpholine was synthesized according to General Procedure C and was isolated as a white solid. MS (APCI): 295 [M+H]⁺.

Example 150

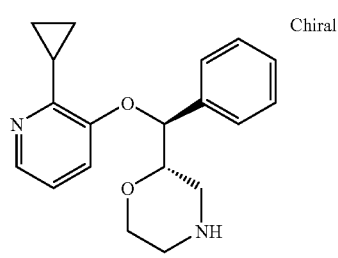

(2S)-2-[(S)-[(2-cyclopropylpyridin-3-yl)oxy](phenyl)methyl]morpholine was synthesized according to General Procedures A and B and was isolated as a white solid. MS (APCI): 311 [M+H]⁺.

Example 151

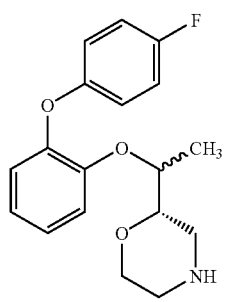

(2S)-2-{1-[2-(4-fluorophenoxy)phenoxy]ethyl}morpholine was synthesized according to General Procedure C and was isolated as a white solid. MS (APCI): 318 [M+H]⁺.

Example 152

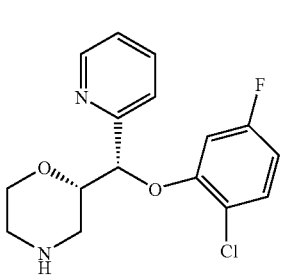

(2S)-2-[(S)-(2-chloro-5-fluorophenoxy)(pyridin-2-yl)methyl]morpholine was synthesized according to General Procedure E and was isolated as a white solid. MS (APCI): 324 [M+H]⁺.

Example 153

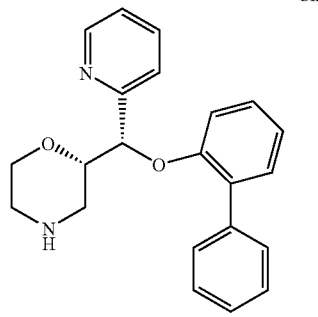

(2S)-2-[(S)-(biphenyl-2-yloxy)(pyridin-2-yl)methyl]morpholine was synthesized according to General Procedure E and was isolated as a white solid. MS (APCI): 347 [M+H]⁺.

Example 154

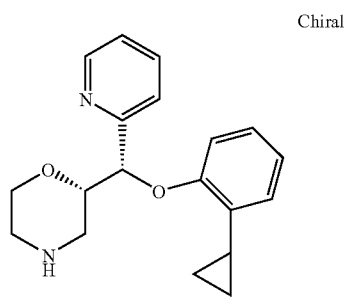

(2S)-2-[(S)-(2-cyclopropylphenoxy)(pyridin-2-yl)methyl]morpholine was synthesized according to General Procedure E and was isolated as a white solid. MS (APCI): 311 [M+H]⁺.

Example 155

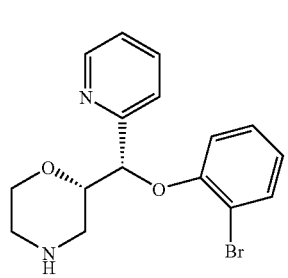

113

(2S)-2-[(S)-(2-bromophenoxy)(pyridin-2-yl)methyl]morpholine was synthesized according to General Procedure E and was isolated as a white solid. MS (APCI): 350 [M+H]⁺.

Example 156

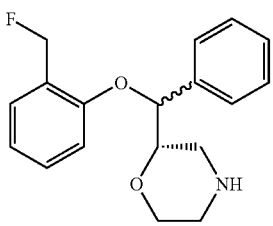

(2S)-2-[[2-(fluoromethyl)phenoxy](phenyl)methyl]morpholine was synthesized according to General Procedure A and was isolated as a white solid. MS (APCI): 302 [M+H]⁺.

Example 157

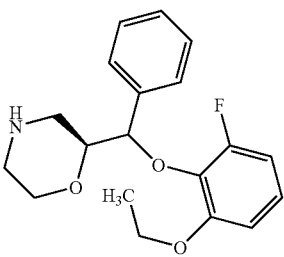

(2S)-2-[(2-ethoxy-6-fluorophenoxy)(phenyl)methyl]morpholine was synthesized according to General Procedure E and was isolated as a white solid. MS (APCI): 332 [M+H]⁺.

Example 158

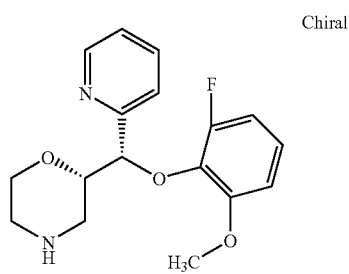

114

(2S)-2-[(S)-(2-fluoro-6-methoxyphenoxy)(pyridin-2-yl)methyl]morpholine was synthesized according to General Procedure E and was isolated as a white solid. MS (APCI): 319 [M+H]⁺.

Example 159

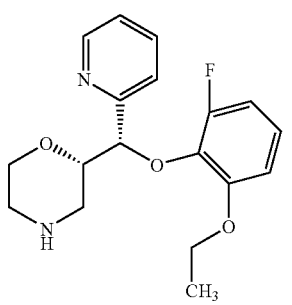

(2S)-2-[(S)-(2-ethoxy-6-fluorophenoxy)(pyridin-2-yl)methyl]morpholine was synthesized according to General Procedure E and was isolated as a white solid. MS (APCI): 333 [M+H]⁺.

Example 160

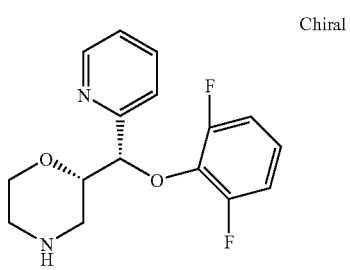

(2S)-2-[(S)-(2,6-difluorophenoxy)(pyridin-2-yl)methyl]morpholine was synthesized according to General Procedure E and was isolated as a white solid. MS (APCI): 307 [M+H]⁺.

Example 161

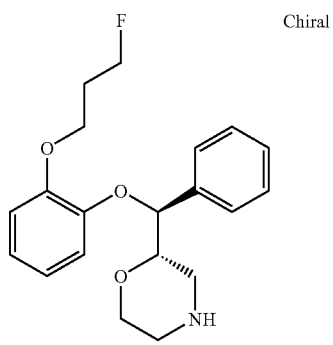

(2S)-2-[(S)-[2-(3-fluoropropoxy)phenoxy](phenyl)methyl]morpholine was synthesized according to General Procedure A and was isolated as a white solid. MS (APCI): 346 [M+H]$^+$.

Example 162

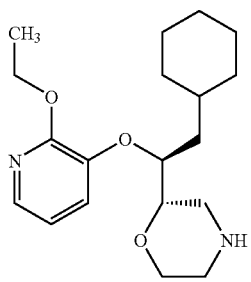

(2S)-2-{(1S)-2-cyclohexyl-1-[(2-ethoxypyridin-3-yl)oxy]ethyl}morpholine was synthesized according to General Procedure C and was isolated as a white solid. MS (APCI): 335 [M+H]$^+$.

Example 163

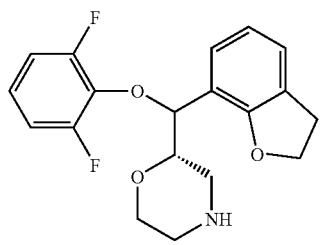

(2S)-2-[(2,6-difluorophenoxy)(2,3-dihydro-1-benzofuran-7-yl)methyl]morpholine was synthesized according to General Procedure E and was isolated as a white solid. MS (APCI): 348 [M+H]$^+$.

Example 164

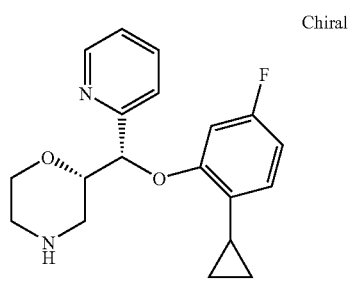

(2S)-2-[(S)-(2-cyclopropyl-5-fluorophenoxy)(pyridin-2-yl)methyl]morpholine was synthesized according to General Procedures E and B and was isolated as a white solid. MS (APCI): 329 [M+H]$^+$.

Example 165

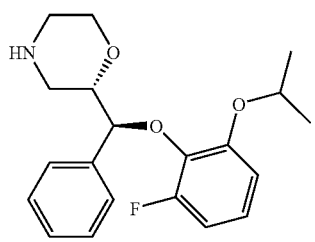

(2S)-2-[(S)-(2-fluoro-6-isopropoxyphenoxy)(phenyl)methyl]morpholine was synthesized according to General Procedure A and was isolated as a white solid. MS (APCI): 346 [M+H]$^+$.

Example 166

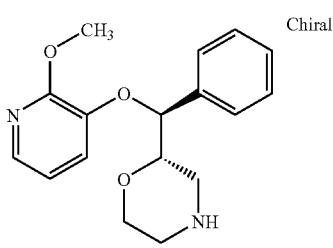

(2S)-2-[(S)-[(2-methoxypyridin-3-yl)oxy](phenyl)methyl]morpholine was synthesized according to General Procedure A and was isolated as a white solid. MS (APCI): 301 [M+H]$^+$.

Example 167

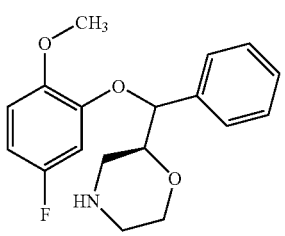

117

(2S)-2-[(5-fluoro-2-methoxyphenoxy)(phenyl)methyl]morpholine was synthesized according to General Procedure C and was isolated as a white solid. MS (APCI): 318 [M+H]+.

Example 168

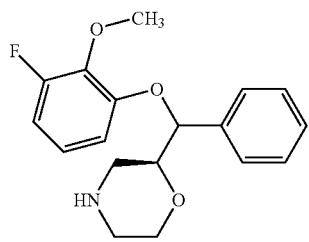

(2S)-2-[(3-fluoro-2-methoxyphenoxy)(phenyl)methyl]morpholine was synthesized according to General Procedure C and was isolated as a white solid. MS (APCI): 318 [M+H]+.

Example 169

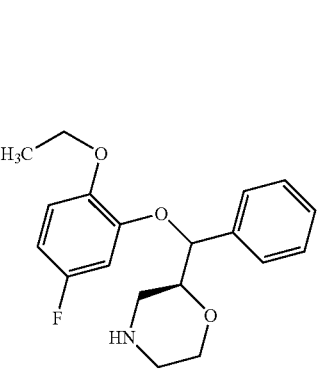

(2S)-2-[(2-ethoxy-5-fluorophenoxy)(phenyl)methyl]morpholine was synthesized according to General Procedure C and was isolated as a white solid. MS (APCI): 332 [M+H]+.

Example 170

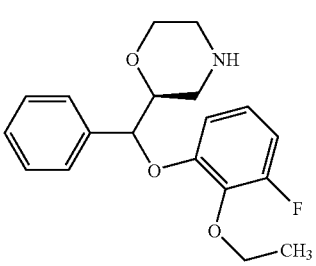

118

(2S)-2-[(2-ethoxy-3-fluorophenoxy)(phenyl)methyl]morpholine was synthesized according to General Procedure C and was isolated as a white solid. MS (APCI): 332 [M+H]+.

Example 171

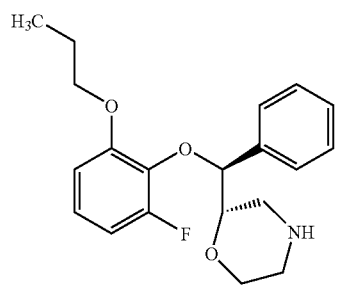

(2S)-2-[(S)-(2-fluoro-6-propoxyphenoxy)(phenyl)methyl]morpholine was synthesized according to General Procedure A and was isolated as a white solid. MS (APCI): 346 [M+H]+.

Example 172

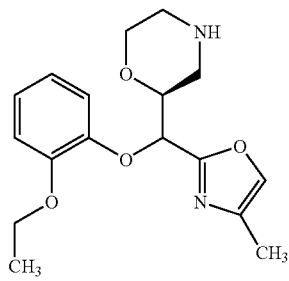

(2S)-2-[(2-ethoxyphenoxy)(4-methyl-1,3-oxazol-2-yl)methyl]morpholine was synthesized according to General Procedure E and was isolated as a white solid. MS (APCI): 319 [M+H]+.

Example 173

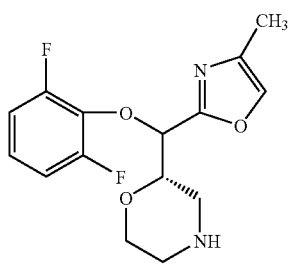

(2S)-2-[(2,6-difluorophenoxy)(4-methyl-1,3-oxazol-2-yl)methyl]morpholine was synthesized according to General Procedure E and was isolated as a white solid. MS (APCI): 311 [M+H]+.

Example 174

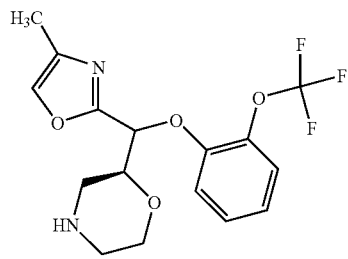

(2S)-2-{(4-methyl-1,3-oxazol-2-yl)[2-(trifluoromethoxy)phenoxy]methyl}morpholine was synthesized according to General Procedure E and was isolated as a white solid. MS (APCI): 359 [M+H]+.

Example 175

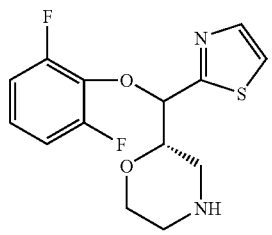

(2S)-2-[(2,6-difluorophenoxy)(1,3-thiazol-2-yl)methyl]morpholine was synthesized according to General Procedure E and was isolated as a white solid. MS (APCI): 313 [M+H]+.

Example 176

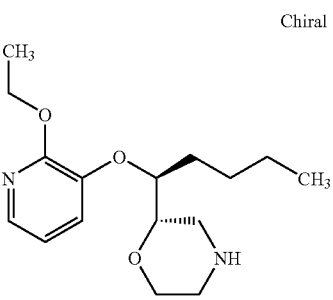

(2S)-2-{(1S)-1-[(2-ethoxypyridin-3-yl)oxy]pentyl}morpholine was synthesized according to General Procedure C and was isolated as a white solid. MS (APCI): 295 [M+H]+.

Example 177

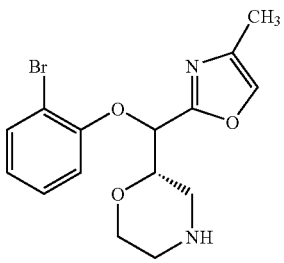

(2S)-2-[(2-bromophenoxy)(4-methyl-1,3-oxazol-2-yl)methyl]morpholine was synthesized according to General Procedure E and was isolated as a white solid. MS (APCI): 354 [M+H]+.

Example 178

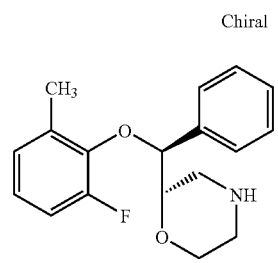

(2S)-2-[(S)-(2-fluoro-6-methylphenoxy)(phenyl)methyl]morpholine was synthesized according to General Procedure A and was isolated as a white solid. MS (APCI): 302 [M+H]+.

Example 179

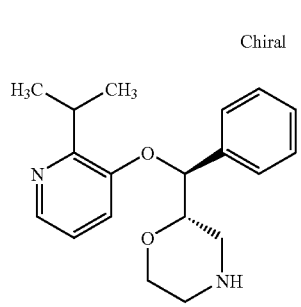

(2S)-2-[(S)-[(2-isopropylpyridin-3-yl)oxy](phenyl)methyl]morpholine was synthesized according to General Procedure A and was isolated as a white solid. MS (APCI): 313 [M+H]⁺.

Example 180

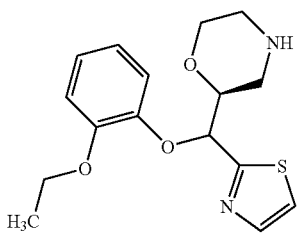

(2S)-2-[(2-ethoxyphenoxy)(1,3-thiazol-2-yl)methyl]morpholine was synthesized according to General Procedure E and was isolated as a white solid. MS (APCI): 321 [M+H]⁺.

Example 181

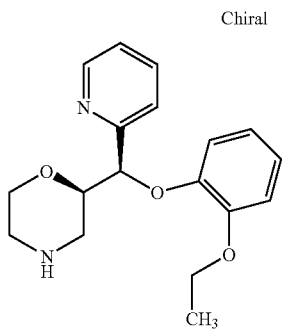

(2R)-2-[(R)-(2-ethoxyphenoxy)(pyridin-2-yl)methyl]morpholine was synthesized from the R morpholine alcohol according to General Procedure E and was isolated as a white solid. MS (APCI): 315 [M+H]⁺.

Example 182

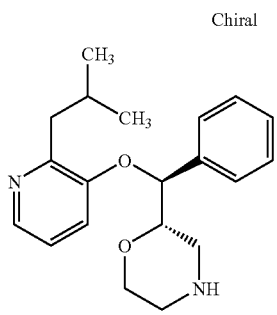

(2S)-2-[(S)-[(2-isobutylpyridin-3-yl)oxy](phenyl)methyl]morpholine was synthesized according to General Procedure A and was isolated as a white solid. MS (APCI): 327 [M+H]⁺.

Example 183

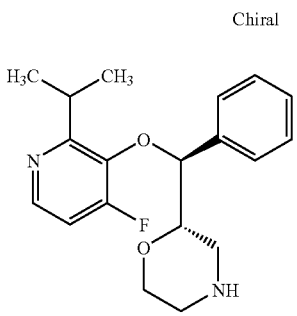

(2S)-2-[(S)-(2-fluoro-6-isopropylphenoxy)(phenyl)methyl]morpholine was synthesized according to General Procedure A and was isolated as a white solid. MS (APCI): 330 [M+H]⁺.

Example 184

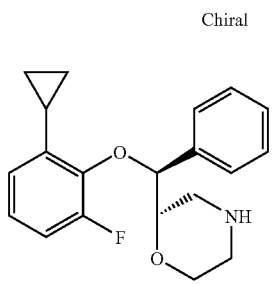

(2S)-2-[(S)-(2-cyclopropyl-6-fluorophenoxy)(phenyl)methyl]morpholine was synthesized according to General Procedure A and was isolated as a white solid. MS (APCI): 328 [M+H]⁺.

Example 185

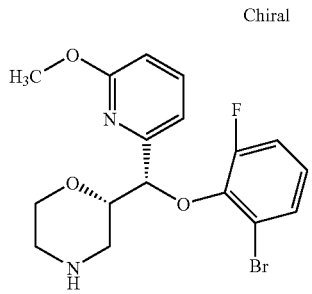

(2S)-2-[(S)-(2-bromo-6-fluorophenoxy)(6-methoxypyridin-2-yl)methyl]morpholine was synthesized according to General Procedure E and was isolated as a white solid. MS (APCI): 398 [M+H]$^+$.

Example 186

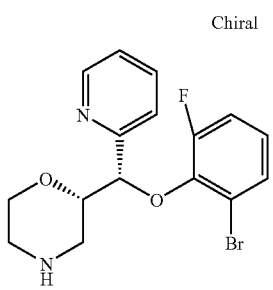

(2S)-2-[(S)-(2-bromo-6-fluorophenoxy)(pyridin-2-yl)methyl]morpholine was synthesized according to General Procedure E and was isolated as a white solid. MS (APCI): 368 [M+H]$^+$.

Example 187

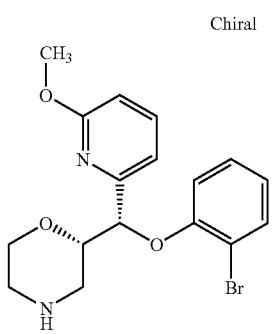

(2S)-2-[(S)-(2-bromophenoxy)(6-methoxypyridin-2-yl)methyl]morpholine was synthesized according to General Procedure E and was isolated as a white solid. MS (APCI): 380 [M+H]$^+$.

Example 188

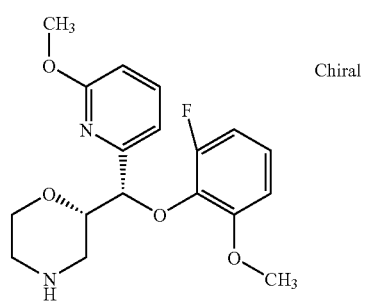

(2S)-2-[(S)-(2-fluoro-6-methoxyphenoxy)(6-methoxypyridin-2-yl)methyl]morpholine was synthesized according to General Procedure E and was isolated as a white solid. MS (APCI): 349 [M+H]$^+$.

Example 189

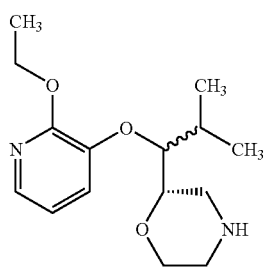

(2S)-2-{1-[(2-ethoxypyridin-3-yl)oxy]-2-methylpropyl}morpholine was synthesized according to General Procedure C and was isolated as a white solid. MS (APCI): 281 [M+H]$^+$.

Example 190

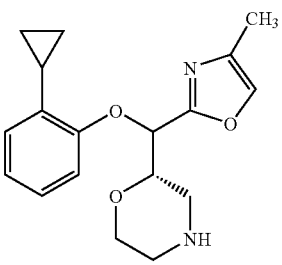

(2S)-2-[(2-cyclopropylphenoxy)(4-methyl-1,3-oxazol-2-yl)methyl]morpholine was synthesized according to General Procedure E and was isolated as a white solid. MS (APCI): 315 [M+H]$^+$.

Example 191

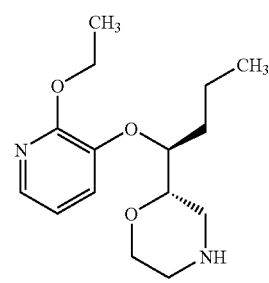

(2S)-2-{(1S)-1-[(2-ethoxypyridin-3-yl)oxy]butyl}morpholine was synthesized according to General Procedure C and was isolated as a white solid. MS (APCI): 281 [M+H]⁺.

Example 192

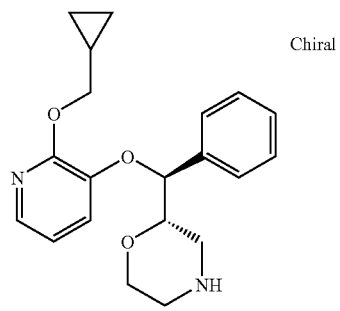

(2S)-2-[(S)-{[2-(cyclopropylmethoxy)pyridin-3-yl]oxy}(phenyl)methyl]morpholine was synthesized according to General Procedure A and was isolated as a white solid. MS (APCI): 341 [M+H]⁺.

Example 193

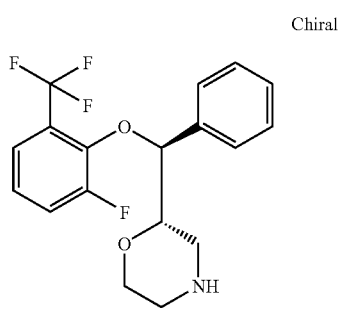

(2S)-2-[(S)-[2-fluoro-6-(trifluoromethyl)phenoxy](phenyl)methyl]morpholine was synthesized according to General Procedure A and was isolated as a white solid. MS (APCI): 356 [M+H]⁺.

Example 194

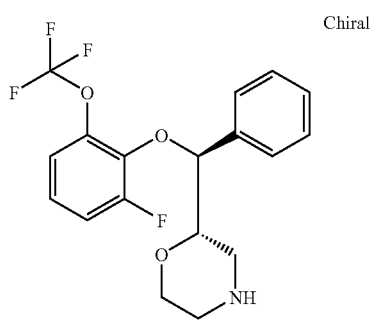

(2S)-2-[(S)-[2-fluoro-6-(trifluoromethoxy)phenoxy](phenyl)methyl]morpholine was synthesized according to General Procedure A and was isolated as a white solid. MS (APCI): 372 [M+H]⁺.

Example 195

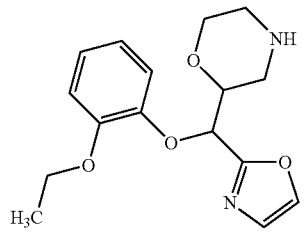

(S)-2-[(2-ethoxyphenoxy)(1,3-oxazol-2-yl)methyl]morpholine was synthesized according to General Procedure E and was isolated as a white solid containing a mixture of diastereoisomers. MS (APCI): 305 [M+H]⁺.

Example 196

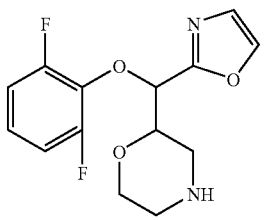

(S)-2-[(2,6-difluorophenoxy)(1,3-oxazol-2-yl)methyl]morpholine was synthesized according to General Procedure E and was isolated as a white solid containing a mixture of diastereoisomers. MS (APCI): 297 [M+H]⁺.

Example 197

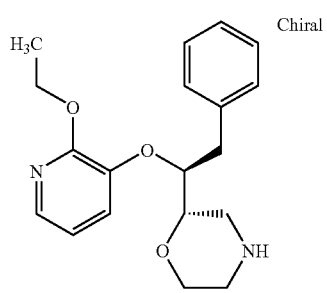

(2S)-2-{(1S)-1-[(2-ethoxypyridin-3-yl)oxy]-2-phenylethyl}morpholine was synthesized according to General Procedure E and was isolated as a white solid. MS (APCI): 329 [M+H]+.

Example 198

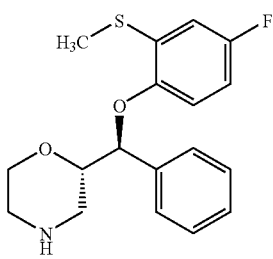

(2S)-2-[(S)-[4-fluoro-2-(methylthio)phenoxy](phenyl)methyl]morpholine was prepared according to General Procedure E and was isolated as the fumarate salt. MS (APCI): 335 [M+H]+.

Example 199

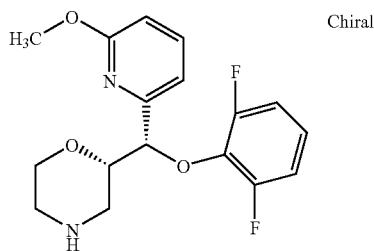

(2S)-2-[(S)-(2,6-difluorophenoxy)(6-methoxypyridin-2-yl)methyl]morpholine was prepared according to General Procedure E and was isolated as the fumarate salt. MS (APCI): 337 [M+H]+.

Example 200

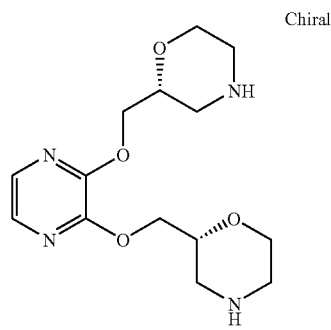

(2R,2'R)-2,2'-[pyrazine-2,3-diylbis(oxymethylene)]dimorpholine was prepared by using General Procedure D starting from 2,3-dichloropyrazine and was isolated as the hydrochloride salt MS (APCI): 311 [M+H]+.

Example 201

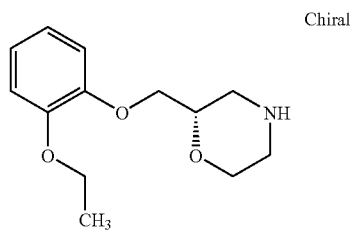

(S)-2-[2-Ethoxy-pyridin-3-yloxymethyl]-morpholine was synthesized via General Procedure D and was isolated as a gummy oil. MS (APCI): 238 [M+H]+.

Example 202

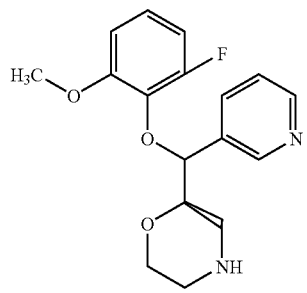

(2R)-2-[(2-fluoro-6-methoxyphenoxy)(pyridin-3-yl)methyl]morpholine was prepared by using General Procedure C starting from 3-bromopyridine and 2-fluoro-6-methoxyphenol and was isolated as a gummy solid containing a mixture of diastereoisomers. MS (APCI): 319 [M+H]+.

Pharmaceutical Composition Examples

In the following Examples, the term 'active compound' or 'active ingredient' refers to a compound according to the present invention above or in a suitable combination with another active agent for example an A2D ligand, an SRI an atypical antipsychotic, etc., and/or a pharmaceutically acceptable salt or solvate, according to the present invention.

(i) Tablet Compositions

The following compositions A and B can be prepared by wet granulation of ingredients (a) to (c) and (a) to (d) with a solution of povidone, followed by addition of the magnesium stearate and compression.

| Composition A | mg/tablet | mg/tablet |
|---|---|---|
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
| | 500 | 300 |

| Composition B | | mg/tablet | mg/tablet |
|---|---|---|---|
| (a) | Active ingredient | 250 | 250 |
| (b) | Lactose | 150 | 150 |
| (c) | Avicel PH 101 | 60 | 26 |
| (d) | Sodium Starch Glycollate | 20 | 12 |
| (e) | Povidone B.P. | 15 | 9 |
| (f) | Magnesium Stearate | 5 | 3 |
| | | 500 | 300 |

| Composition C | mg/tablet |
|---|---|
| Active ingredient | 100 |
| Lactose | 200 |
| Starch | 50 |
| Povidone | 5 |
| Magnesium Stearate | 4 |
| | 359 |

The following compositions D and E can be prepared by direct compression of the admixed ingredients. The lactose used in formulation E is of the direct compression type.

| Composition D | mg/tablet |
|---|---|
| Active ingredient | 250 |
| Magnesium Stearate | 4 |
| Pregelatinised Starch NF15 | 146 |
| | 400 |

| Composition E | mg/tablet |
|---|---|
| Active ingredient | 250 |
| Magnesium Stearate | 5 |
| Lactose | 145 |
| Avicel | 100 |
| | 500 |

| Composition F (Controlled release composition) | | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P.C. | 28 |
| (e) | Magnesium Stearate | 7 |
| | | 700 |

The composition can be prepared by wet granulation of ingredients (a) to (c) with a solution of povidone, followed by addition of the magnesium stearate and compression.

Composition G (Enteric-coated Tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated Controlled Release Tablet)

Enteric-coated tablets of Composition F can be prepared by coating the tablets with 50 mg/tablet of an enteric polymer such as cellulose acetate phthalate, polyvinylacetate phthalate, hydroxypropylmethyl- cellulose phthalate, or anionic polymers of methacrylic acid and methacrylic acid methyl ester (Eudgragit L). Except for Eudgragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule Compositions

Composition A

Capsules can be prepared by admixing the ingredients of Composition D above and filling two-part hard gelatin capsules with the resulting mixture. Composition B (infra) may be prepared in a similar manner.

| Composition B | | mg/capsule |
|---|---|---|
| (a) | Active ingredient | 250 |
| (b) | Lactose B.P. | 143 |
| (c) | Sodium Starch Glycollate | 25 |
| (d) | Magnesium Stearate | 2 |
| | | 420 |

| Composition C | | mg/capsule |
|---|---|---|
| (a) | Active ingredient | 250 |
| (b) | Macrogol 4000 BP | 350 |
| | | 600 |

Capsules can be prepared by melting the Macrogol 4000 BP, dispersing the active ingredient in the melt and filling two-part hard gelatin capsules therewith.

| Composition D | mg/capsule |
|---|---|
| Active ingredient | 250 |
| Lecithin | 100 |
| Arachis Oil | 100 |
| | 450 |

Capsules can be prepared by dispersing the active ingredient in the lecithin and arachis oil and filling soft, elastic gelatin capsules with the dispersion.

| Composition E (Controlled release capsule) | | mg/capsule |
|---|---|---|
| (a) | Active ingredient | 250 |
| (b) | Microcrystalline Cellulose | 125 |
| (c) | Lactose BP | 125 |
| (d) | Ethyl Cellulose | 13 |
| | | 513 |

The controlled release capsule formulation can be prepared by extruding mixed ingredients (a) to (c) using an extruder, then spheronising and drying the extrudate. The dried pellets are coated with a release controlling membrane (d) and filled into two-part, hard gelatin capsules.

| Composition F (Enteric capsule) | mg/capsule |
|---|---|
| (a) Active ingredient | 250 |
| (b) Microcrystalline Cellulose | 125 |
| (c) Lactose BP | 125 |
| (d) Cellulose Acetate Phthalate | 50 |
| (e) Diethyl Phthalate | 5 |
| | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated Controlled Release Capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) or a plasticizer to prevent membrane cracking during application or on storage. Suitable plasticizers include diethyl phthalate, tributyl citrate and triacetin.

(iii) Intravenous Injection Composition

| Active ingredient | 0.200 g |
|---|---|
| Sterile, pyrogen-free phosphate buffer (pH 9.0) to | 10 ml |

The active ingredient is dissolved in most of the phosphate buffer at 35-40° C., then made up to volume and filtered through a sterile micropore filter into sterile 10 ml glass vials (Type 1) which are sealed with sterile closures and overseals.

(iv) Intramuscular Injection Composition

| Active ingredient | 0.20 g |
|---|---|
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

(v) Syrup Composition

| Active ingredient | 0.25 g |
|---|---|
| Sorbitol Solution | 1.50 g |
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

(vi) Suppository Composition

| | mg/suppository |
|---|---|
| Active ingredient | 250 |
| Hard Fat, BP (Witepsol H15 - Dynamit NoBel) | 1770 |
| | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38-40° C., 2.02 g aliquots of the mixture are filled into suitable plastic moulds and the suppositories allowed to cool to room temperature.

(vii) Pessary Composition

| | mg/pessary |
|---|---|
| Active ingredient | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

(viii) Transdermal Composition

| Active ingredient | 200 mg |
|---|---|
| Alcohol USP | 0.1 ml |
| Hydroxyethyl cellulose | |

The active ingredient and alcohol USP are gelled with hydroxyethyl cellulose and packed in a transdermal device with a surface area of 10 cm².

All references cited herein are incorporated by reference in their entirety and for all purposes.

What is claimed is:

1. A compound of Formula III:

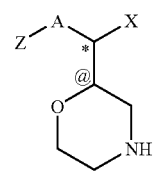

III and pharmaceutically and/or veterinarily acceptable salts thereof, wherein:

A is O;

Z is pyridyl substituted with one of halo, phenyl, —O-phenyl, —O—$(C_1$-$C_6)$alkyl-, $(C_1$-$C_6)$alkyl, or cyclopropyl wherein said phenyl can be optionally substituted by halo or $(C_1$-$C_6)$alkyl phenyl, X is phenyl, methyl, ethyl, i-propyl, n-propyl-, and —$CH_2$-cyclohexyl;

* denotes a first chiral center; and

@ denotes a second chiral center.

2. A compound selected from the following compounds and their pharmaceutically acceptable salts:

2-[(1-Oxy-pyridin-2-yloxy)-phenyl-methyl]-morpholine;
2-{[2-(4-Fluoro-phenyl)-pyridin-3-yloxy]-phenyl-methyl}-morpholine;
2-[Phenyl-(pyridin-3-yloxy)-methyl]-morpholine;
2-[(2-Bromo-pyridin-3-yloxy)-phenyl-methyl]-morpholine;
2-[Phenyl-(2-p-tolyl-pyridin-3-yloxy)-methyl]-morpholine;
2-{[2-4-Fluoro-phenoxy)-pyridin-3-yloxy]-phenyl-methyl}-morpholine;
2-[{[2-(4-fluorophenoxy)pyridin-3-yl]oxy}(phenyl)methyl]morpholine;
2-[[(2-ethylpyridin-3-yl)oxy](phenyl)methyl]morpholine;
2-[[(2-methylpyridin-3-yl)oxy](phenyl)methyl]morpholine;
2-{phenyl[(2-propylpyridin-3-yl)oxy]methyl}morpholine;
2-{1-[(2-ethoxypyridin-3-yl)oxy]propyl}morpholine;
2-[[(2-ethoxypyridin-3-yl)oxy](phenyl)methyl]morpholine;
2-{1-[(2-ethoxypyridin-3-yl)oxy]ethyl}morpholine;
2-{1-[(2-ethoxypyridin-3-yl)oxy]-3-methylbutyl}morpholine;
2-[[(2-cyclopropylpyridin-3-yl)oxy](phenyl)methyl]morpholine;
2-{2-cyclohexyl-1-[(2-ethoxypyridin-3-yl)oxy]ethyl}morpholine;
2-[[(2-methoxypyridin-3-yl)oxy](phenyl)methyl]morpholine;
2-{1-[(2-ethoxypyridin-3-yl)oxy]pentyl}morpholine;
2-[[(2-isopropylpyridin-3-yl)oxy](phenyl)methyl]morpholine;
2-[[(2-isobutylpyridin-3-yl)oxy](phenyl)methyl]morpholine;
2-{1-[(2-ethoxypyridin-3-yl)oxy]-2-methylpropyl}morpholine;
2-{1-[(2-ethoxypyridin-3-yl)oxy]butyl}morpholine;
2-[{[2-(cyclopropylmethoxy)pyridin-3-yl]oxy}(phenyl)methyl]morpholine;
2-{1-[2-ethoxypyridin-3-yl)oxy]-2-phenylethyl}morpholine; and
enantiomers and diastereomers of the preceding compounds.

3. A compound selected from the following compounds and their pharmaceutically acceptable salts:

(S)-2-[((S)-1-Oxy-pyridin-2-yloxy)-phenyl-methyl]-morpholine;
(S)-2-{(S)-[2-(4-Fluoro-phenyl)-pyridin-3-yloxy]-phenyl-methyl}-morpholine;
(S)-2-[(S)-Phenyl-(pyridin-3-yloxy)-methyl]-morpholine;
(S)-2-[(S)-(2-Bromo-pyridin-3-yloxy)-phenyl-methyl]-morpholine;
(S)-2-[(S)-Phenyl-(2-p-tolyl-pyridin-3-yloxy)-methyl]-morpholine;
(S)-2-{(S)-[2-(4-Fluoro-phenoxy)-pyridin-3-yloxy]-phenyl-methyl}-morpholine;
(2S)-2-[(S)-{[2-(4-fluorophenoxy)pyridin-3-yl]oxy}(phenyl)methyl]morpholine;
(2S)-2-[(S)-[(2-ethylpyridin-3-yl)oxy](phenyl)methyl]morpholine;
(2S)-2-[(S)-[(2-methylpyridin-3-yl)oxy](phenyl)methyl]morpholine;
(2S)-2-{(S)-phenyl[(2-propylpyridin-3-yl)oxy]methyl}morpholine;
(2S)-2-{1-[(2-ethoxypyridin-3-yl)oxy]propyl}morpholine;
(2S)-2-[(S)-[(2-ethoxypyridin-3-yl)oxy](phenyl)methyl]morpholine;
(2S)-2-{(1S)-1-[(2-ethoxypyridin-3-yl)oxy]ethyl}morpholine;
(2S)-2-{1-[(2-ethoxypyridin-3-yl)oxy]-3-methylbutyl}morpholine;
(2S)-2-[(S)-[(2-cyclopropylpyridin-3-yl)oxy](phenyl)methyl]morpholine;
(2S)-2-{(1S)-2-cyclohexyl-1-[(2-ethoxypyridin-3-yl)oxy]ethyl}morpholine;
(2S)-2-[(S)-[(2-methoxypyridin-3-yl)oxy](phenyl)methyl]morpholine;
(2S)-2-{(1S)-1-[(2-ethoxypyridin-3-yl)oxy]pentyl}morpholine;
(2S)-2-[(S)-[(2-isopropylpyridin-3-yl)oxy](phenyl)methyl]morpholine;
(2S)-2-[(S)[(2-isobutylpyridin-3-yl)oxy](phenyl)methyl]morpholine;
(2S)-2-{1-[(2-ethoxypyridin-3-yl)oxy]-2-methylpropyl}morpholine;
(2S)-2-{(1S)-1-[(2-ethoxypyridin-3-yl)oxy]butyl}morpholine;
(2S)-2-[(S)-{[2-(cyclopropylmethoxy)pyridin-3-yl]oxy}(phenyl)methyl]morpholine;
(2S)-2-{(1S)-1-[(2-ethoxypyridin-3-yl)oxy]-2-phenylethyl}morpholine; and
enantiomers and diastereomers of the preceding compounds.

4. A pharmaceutical composition comprising a compound or a pharmaceutically acceptable salt thereof as defined in claim 1 and a pharmaceutically acceptable carrier.

5. A compound according to claim 1, and pharmaceutically and/or veterinarily acceptable salts thereof, wherein Z is pyridyl substituted with $C_1$-$C_6$ alkoxy and —O-aryl.

6. A compound according to claim 5, and pharmaceutically and/or veterinarily acceptable salts thereof, wherein Z is pyridyl substituted with $C_1$-$C_6$ alkoxy.

7. A compound according to claim 5, and pharmaceutically and/or veterinarily acceptable salts thereof, wherein Z is pyridyl substituted with —O-aryl substituents.

8. The compound (2S)-2-{1-[(2-ethoxypyridin-3-yl)oxy]-3-methylbutyl}morpholine or a pharmaceutically acceptable salt thereof.

9. The compound (S)-2-[(S)-Phenyl-(pyridin-3-yloxy)-methyl]-morpholine or a pharmaceutically acceptable salt thereof.

10. The compound (2S)-2-{(1S)-1-[(2-ethoxypyridin-3-yl)oxy]-2-phenylethyl}morpholine or a pharmaceutically acceptable salt thereof.

* * * * *